(12) United States Patent
Howie et al.

(10) Patent No.: US 12,310,709 B2
(45) Date of Patent: *May 27, 2025

(54) COMPUTATION OF PARAMETERS OF A BODY USING AN ELECTRIC FIELD

(71) Applicant: Life Detection Technologies, Inc., Sunnyvale, CA (US)

(72) Inventors: Eric Carlin Howie, Henderson, NV (US); Mark Bradford Flowers, Los Gatos, CA (US); Tandhoni Srinivasa Rao, Charlestown, MA (US); Orville Rey Rule, III, Los Altos Hills, CA (US); Darpan Dinesh Damani, Milpitas, CA (US); Guy McIlroy, Los Gatos, CA (US); John Robert Haggis, San Jose, CA (US); John Bertram Langley, II, Half Moon Bay, CA (US); Steven Sven Fastert, Chelmsford, MA (US); William Frederick Ellersick, Hampton, NH (US); Dwight David Birdsall, Fort Collins, CO (US)

(73) Assignee: Life Detection Technologies, Inc., Sunnyvale, CA (US)

( * ) Notice: Subject to any disclaimer, the term of this patent is extended or adjusted under 35 U.S.C. 154(b) by 163 days.

This patent is subject to a terminal disclaimer.

(21) Appl. No.: 17/930,243

(22) Filed: Sep. 7, 2022

(65) Prior Publication Data

US 2023/0000380 A1 Jan. 5, 2023

Related U.S. Application Data

(63) Continuation-in-part of application No. 17/546,679, filed on Dec. 9, 2021, now Pat. No. 11,684,283,
(Continued)

(51) Int. Cl.
*G01R 29/12* (2006.01)
*A61B 5/00* (2006.01)
(Continued)

(52) U.S. Cl.
CPC .............. *A61B 5/05* (2013.01); *A61B 5/7278* (2013.01); *A61B 5/742* (2013.01);
(Continued)

(58) Field of Classification Search
CPC ...... G01R 29/08; G01R 29/0814; A61B 5/05; A61B 5/725; A61B 5/742; A61B 5/746;
(Continued)

(56) References Cited

U.S. PATENT DOCUMENTS

| 4,182,315 A | 1/1980 | Vas et al. |
| 4,532,501 A | 7/1985 | Hoffman |

(Continued)

FOREIGN PATENT DOCUMENTS

| CN | 1424577 A | 6/2003 |
| CN | 1630822 A | 6/2005 |

(Continued)

OTHER PUBLICATIONS

Declaration of Non-Establishment of International Search Report and Written Opinion received for PCT Application No. PCT/US2022/080854, mailed on May 16, 2023, 9 pages.

(Continued)

*Primary Examiner* — Thang X Le
(74) *Attorney, Agent, or Firm* — Weaver IP L.L.C.

(57) ABSTRACT

In some embodiments, an electric field generator includes a differential oscillator that oscillates at a nominal frequency. The electric field generator is connected to a differential antenna that radiates an electric field. A differential detector measures a frequency of the generated electric field as the electric field interacts with a body (such as a human body)
(Continued)

in a reactive near-field region of the electric field. For each of one or more internal components of the body, a computation unit determines a respective periodic behavior in the measured frequency indicative of movement of the internal component. The computation unit also computes, for each of the one or more internal components of the body, a respective rate of movement (such as a heart rate or a respiration rate) of the internal component according to the respective periodic behavior in the measured frequency.

31 Claims, 18 Drawing Sheets

Related U.S. Application Data which is a continuation of application No. 16/824,182, filed on Mar. 19, 2020, now Pat. No. 11,253,163, which is a continuation of application No. 16/139,993, filed on Sep. 24, 2018, now Pat. No. 10,631,752, which is a continuation-in-part of application No. 15/418,328, filed on Jan. 27, 2017, now Pat. No. 10,080,507, application No. 17/930,243 is a continuation-in-part of application No. 16/890,970, filed on Jun. 2, 2020, now Pat. No. 11,464,452.

(60) Provisional application No. 62/287,598, filed on Jan. 27, 2016, provisional application No. 62/856,564, filed on Jun. 3, 2019, provisional application No. 63/286,305, filed on Dec. 6, 2021, provisional application No. 63/329,709, filed on Apr. 11, 2022, provisional application No. 63/345,581, filed on May 25, 2022.

(51) Int. Cl.
*A61B 5/05* (2021.01)
*G01R 29/08* (2006.01)
*A61B 5/024* (2006.01)
*A61B 5/08* (2006.01)
*A61B 5/11* (2006.01)
*A61B 5/113* (2006.01)

(52) U.S. Cl.
CPC .......... *G01R 29/0814* (2013.01); *A61B 5/024* (2013.01); *A61B 5/0816* (2013.01); *A61B 5/1102* (2013.01); *A61B 5/113* (2013.01); *A61B 5/7225* (2013.01); *A61B 5/725* (2013.01)

(58) Field of Classification Search
CPC . A61B 5/7203; A61B 5/0402; A61B 5/04018; G01N 27/22; G08B 21/02; G08B 21/0211
See application file for complete search history.

(56) References Cited

U.S. PATENT DOCUMENTS

| | | |
|---|---|---|
| 4,788,869 A | 12/1988 | Li |
| 4,958,638 A | 9/1990 | Sharpe et al. |
| 5,434,887 A | 7/1995 | Osaka |
| 5,724,990 A | 3/1998 | Ogino |
| 5,902,255 A | 5/1999 | Ogino |
| 6,020,784 A | 2/2000 | Fujii |
| 6,161,070 A * | 12/2000 | Jinno ............... B60R 21/01532 701/45 |
| 6,297,738 B1 | 10/2001 | Newham |
| 6,339,623 B1 | 1/2002 | Iwamatsu |
| 6,356,746 B1 | 3/2002 | Katayama |
| 6,679,830 B2 | 1/2004 | Kolarovic et al. |
| 6,686,800 B2 | 2/2004 | Krupka |
| 6,778,090 B2 | 8/2004 | Newham |
| 7,109,726 B2 | 9/2006 | van Berkel |
| 7,173,525 B2 | 2/2007 | Albert |
| 7,242,728 B2 | 7/2007 | Kanazawa |
| 7,331,071 B1 | 2/2008 | Cherubini et al. |
| 7,383,071 B1 | 6/2008 | Russell et al. |
| 7,445,605 B2 | 11/2008 | Overall et al. |
| 7,652,581 B2 | 1/2010 | Gentry et al. |
| 7,836,529 B2 | 11/2010 | Cherubini et al. |
| 7,885,700 B2 | 2/2011 | Clark et al. |
| 7,887,708 B2 | 2/2011 | Chew |
| 7,952,425 B2 | 5/2011 | Zhang et al. |
| 8,057,388 B1 | 11/2011 | Russell et al. |
| 8,274,386 B1 | 9/2012 | Dea et al. |
| 8,604,772 B2 | 12/2013 | Berkcan et al. |
| 8,672,842 B2 | 3/2014 | Kenalty et al. |
| 8,842,010 B2 | 9/2014 | Cehelnik |
| 8,994,536 B2 | 3/2015 | Margon |
| 9,035,778 B2 | 5/2015 | Howie et al. |
| 9,060,745 B2 | 6/2015 | Su et al. |
| 9,204,802 B2 | 12/2015 | Feldman et al. |
| 9,285,889 B2 | 3/2016 | Bateman et al. |
| 9,549,682 B2 * | 1/2017 | Howie .................. G01N 27/22 |
| 9,603,542 B2 * | 3/2017 | Veen ...................... A61B 5/302 |
| 9,662,505 B2 | 5/2017 | Kibler et al. |
| 9,685,996 B1 | 6/2017 | Thoen |
| 9,921,706 B2 | 3/2018 | Kim et al. |
| 10,080,507 B2 | 9/2018 | Langley, II et al. |
| 10,631,752 B2 | 4/2020 | Langley, II et al. |
| 11,026,593 B2 | 6/2021 | Langley, II et al. |
| 11,253,163 B2 | 2/2022 | Langley, II et al. |
| 11,464,452 B2 | 10/2022 | Haggis et al. |
| 11,523,745 B2 | 12/2022 | Langley, II et al. |
| 11,684,283 B2 | 6/2023 | Langley, II et al. |
| 2002/0013538 A1 | 1/2002 | Teller |
| 2002/0032016 A1 | 3/2002 | Ji |
| 2002/0070866 A1 | 6/2002 | Newham |
| 2003/0021078 A1 | 1/2003 | van Berkel |
| 2004/0100376 A1 | 5/2004 | Lye et al. |
| 2004/0181703 A1 | 9/2004 | Lilja et al. |
| 2004/0201384 A1 | 10/2004 | Berkel |
| 2004/0250192 A1 | 12/2004 | Kanazawa |
| 2004/0260346 A1 | 12/2004 | Overall et al. |
| 2005/0104670 A1 | 5/2005 | Naviasky et al. |
| 2005/0190068 A1 | 9/2005 | Gentry et al. |
| 2005/0273218 A1 | 12/2005 | Breed et al. |
| 2006/0154642 A1 | 7/2006 | Scannell, Jr. |
| 2006/0158173 A1 | 7/2006 | Takiguchi |
| 2006/0261818 A1 | 11/2006 | Zank et al. |
| 2007/0055123 A1 | 3/2007 | Takiguchi |
| 2007/0139049 A1 | 6/2007 | Van Berkel |
| 2007/0285296 A1 | 12/2007 | Bilhan |
| 2008/0007445 A1 | 1/2008 | Leach, Jr. et al. |
| 2008/0074307 A1 | 3/2008 | Boric-Lubecke et al. |
| 2008/0136226 A1 | 6/2008 | Cherubini et al. |
| 2008/0259043 A1 | 10/2008 | Buil et al. |
| 2009/0048500 A1 | 2/2009 | Corn |
| 2009/0079550 A1 | 3/2009 | Makinen et al. |
| 2009/0240160 A1 | 9/2009 | Thompson et al. |
| 2009/0318779 A1 | 12/2009 | Tran |
| 2010/0060350 A1 | 3/2010 | Zhang et al. |
| 2010/0152600 A1 | 6/2010 | Droitcour et al. |
| 2010/0201355 A1 | 8/2010 | Yamaguchi et al. |
| 2010/0231234 A1 | 9/2010 | Tateishi et al. |
| 2011/0001622 A1 | 1/2011 | Gentry et al. |
| 2011/0308015 A1 | 12/2011 | Newham |
| 2012/0053424 A1 | 3/2012 | Kenalty et al. |
| 2013/0267791 A1 | 10/2013 | Halperin et al. |
| 2013/0285672 A1 | 10/2013 | Russell et al. |
| 2014/0055269 A1 | 2/2014 | Howie et al. |
| 2014/0059778 A1 | 3/2014 | Jalbert |
| 2014/0140444 A1 | 5/2014 | Onishi et al. |
| 2014/0222110 A1 | 8/2014 | Kibler et al. |
| 2015/0031964 A1 | 1/2015 | Bly et al. |
| 2015/0057557 A1 | 2/2015 | Howie et al. |
| 2015/0065841 A1* | 3/2015 | Lee ...................... A61B 5/4869 600/388 |
| 2015/0157269 A1 | 6/2015 | Lisogurski et al. |
| 2015/0212027 A1 | 7/2015 | Dhurjaty |
| 2015/0276976 A1 | 10/2015 | Holenarsipur et al. |

(56) References Cited

U.S. PATENT DOCUMENTS

| | | | |
|---|---|---|---|
| 2015/0317002 A1 | 11/2015 | King-Smith et al. | |
| 2016/0137148 A1* | 5/2016 | Breed | H03K 17/955 |
| | | | 280/771 |
| 2016/0148034 A1 | 5/2016 | Kremin et al. | |
| 2016/0179243 A1 | 6/2016 | Schwartz | |
| 2016/0187277 A1 | 6/2016 | Potyrailo et al. | |
| 2016/0187450 A1 | 6/2016 | Heim et al. | |
| 2017/0209065 A1 | 7/2017 | Langley, II et al. | |
| 2017/0363458 A1 | 12/2017 | Mitani | |
| 2018/0092557 A1 | 4/2018 | Bickford et al. | |
| 2018/0210582 A1 | 7/2018 | Kim et al. | |
| 2018/0368724 A1 | 12/2018 | Langley, II et al. | |
| 2019/0021647 A1* | 1/2019 | Zheng | A61B 5/7225 |
| 2019/0029556 A1 | 1/2019 | Langley, II et al. | |
| 2019/0298208 A1 | 10/2019 | Weinstein et al. | |
| 2020/0163569 A1 | 5/2020 | Schwartz et al. | |
| 2020/0214587 A1 | 7/2020 | Langley, II et al. | |
| 2020/0214621 A1 | 7/2020 | Keroles et al. | |
| 2020/0375542 A1 | 12/2020 | Haggis et al. | |
| 2021/0228103 A1 | 7/2021 | Richter et al. | |
| 2021/0356500 A1 | 11/2021 | Jankowski | |
| 2022/0095943 A1 | 3/2022 | Langley, II et al. | |
| 2022/0183581 A1 | 6/2022 | Kleijnen et al. | |
| 2022/0202397 A1 | 6/2022 | Greenwood et al. | |
| 2022/0409082 A1 | 12/2022 | Howie et al. | |
| 2023/0000381 A1 | 1/2023 | Howie et al. | |
| 2023/0115139 A1 | 4/2023 | Langley, II et al. | |

FOREIGN PATENT DOCUMENTS

| | | |
|---|---|---|
| CN | 101277645 A | 10/2008 |
| CN | 104644143 A | 5/2015 |
| CN | 108601531 A | 9/2018 |
| EP | 2093588 A1 | 8/2009 |
| EP | 2702973 A1 | 3/2014 |
| EP | 2886051 A1 | 6/2015 |
| EP | 3415090 A1 | 12/2018 |
| EP | 3407778 B1 | 1/2021 |
| EP | 3856013 A1 | 8/2021 |
| EP | 4444168 A1 | 10/2024 |
| FR | 2923150 A1 | 5/2009 |
| GB | 2062239 A | 5/1981 |
| JP | S60-142274 A | 7/1985 |
| JP | H07-288551 A | 10/1995 |
| JP | 2002-164398 A | 6/2002 |
| JP | 2006-506621 A | 2/2006 |
| JP | 2008-541826 A | 11/2008 |
| JP | 2010-504155 A | 2/2010 |
| JP | 2010-537767 A | 12/2010 |
| JP | 2011-145214 A | 7/2011 |
| JP | 2011-519288 A | 7/2011 |
| JP | 2012-073251 A | 4/2012 |
| JP | 2012-239748 A | 12/2012 |
| JP | 2014-210137 A | 11/2014 |
| JP | 2015-091358 A | 5/2015 |
| JP | 2015-205045 A | 11/2015 |
| JP | 2016-020815 A | 2/2016 |
| JP | 2016-506524 A | 3/2016 |
| JP | 2019-505767 A | 2/2019 |
| JP | 2019-509473 A | 4/2019 |
| JP | 7217470 B2 | 2/2023 |
| JP | 7385187 B2 | 11/2023 |
| JP | 7468837 B2 | 4/2024 |
| WO | 03/048789 A2 | 6/2003 |
| WO | 2005/079530 A2 | 9/2005 |
| WO | 2015/174879 A1 | 11/2015 |
| WO | 2017/132514 A1 | 8/2017 |
| WO | 2018/137977 A1 | 8/2018 |
| WO | 2018/202486 A1 | 8/2018 |
| WO | 2019/060250 A1 | 3/2019 |
| WO | 2020/068571 A1 | 4/2020 |
| WO | 2021/090954 A1 | 5/2021 |
| WO | 2023/107864 A1 | 6/2023 |
| WO | 2023/107865 A1 | 6/2023 |
| WO | 2023/107866 A2 | 6/2023 |

OTHER PUBLICATIONS

International Search Report and Written Opinion received for PCT Application No. PCT/US2022/080850, mailed on Feb. 24, 2023, 12 pages.
International Search Report and Written Opinion received for PCT Application No. PCT/US2022/080852, mailed on Mar. 17, 2023, 12 pages.
Office Action received for Canada Patent Application No. 3012319, mailed on Feb. 14, 2023, 3 pages.
Office Action received for Japanese Patent Application No. 2021-540782, mailed on Apr. 18, 2023, 6 pages (4 pages of English Translation and 2 pages of Official Copy).
Office Action received for Japanese Patent Application No. 2022-011295, mailed on Mar. 7, 2023, 9 pages (6 pages of English Translation and 3 pages of Official Copy).
Notice of Decision to Grant received for Japanese Patent Application No. 2021-540782, mailed on Oct. 3, 2023, 4 pages (3 pages of English Translation and 1 page of Official Copy).
Office Action received for Canada Patent Application No. 3012319, mailed on Nov. 21, 2023, 4 pages.
Notice of Decision to Grant Received for Japanese Patent Application No. 2022-011295, mailed on Feb. 27, 2024, 1 page (Official Copy only).
Extended European Search Report received for European Patent Application No. 19866310.6, mailed on Jun. 10, 2022, 8 pages.
Extended European Search Report received for European Patent Application No. 17744973.3 dated Aug. 21, 2019, 8 pages.
Heartfelt tm Infant Vitals & Video Monitoring System, [online] (c) 2012 PREE Corporation, [retrieved on Sep. 20, 2012], Retrieved from the Internet: <URL:http://www.technophysics.com/technology/heartfelt_baby_monitor>, 2012, 4 pages.
International Search Report and Written Opinion for International Patent Application No. PCT/US2017/015345, dated Apr. 17, 2017, 10 pages.
International Search Report received in related PCT Application No. PCT/US19/52076 dated Dec. 13, 2019, 10 pages.
Non-Contact Monitor for Infants at Risk, SBIR/STTR.Award. [online] [retrieved on Sep. 20, 2012]. Retrieved from Internet: <URL:http://www.sbir.gov/sbirsearch/detail/156740>, 2 pages.
Office Action received in related Chinese Application No. 201780008413.6 dated Nov. 3, 2020, 13 pages.
Office Action received in related Japanese Patent Application No. 2018-539839 dated Oct. 13, 2020, 8 pages.
PREE Corporation's Heartfelt Infant Vitals and Video Monitoring System is Now in Pre-Sales, PREE Corporation Press Release, [online] [retrieved Sep. 20, 2012]. Retrieved from the Internet: <URL:http://www.businesswire.com/news/home/20120215006285/en/PREE-Corporations-Heartfelt-Infant-Vitals-Video-Monitoring>, Feb. 15, 2012, 1 page.
Standards for assessing, measuring and monitoring vital signs in infants, children and young people, (c) 2011 Royal College of Nursing, [online] [retrieved Sep. 20, 2012]. Retrieved from the Internet: <URL: http://www.rcn.org.uk/_data/assets/pdf_file/0004/114484/003196.pdf>, 2011, 16 pages.
TDC7200: Time-to-digital converter for time-of-flight (ToF) application for LIDAR and ultrasonic, Retrieved from the Internet URL: https://www.ti.com/product/TDC7200, published Jan. 8, 2015.
Beardsmore-Rust, S.T. , "Remote applications of electric potential sensors in electrically unshielded environments", PhD. Thesis, University of Sussex. [online]. [retrieved on Sep. 20, 2012]. Retrieved from the Internet: <URL:http://sro.sussex.ac.uk/2407/1/Beardsmore-Rust%2C_Sam.pdf>, Apr. 2010, 185 pages.
Buckley, P., "Plessey EPIC sensor makes a heart monitor in a wristwatch", [online]. EE Times Europe. [retrieved on Sep. 20, 2012]. Retrieved from the Internet: <URL:http://www.eetimes.com/electronics-news/4372353/Plessey-reveals-EPIC-sensor-technology-to-create-a-heart-monitor-in-a-wristwatch>, May 6, 2012, 2 pages.

(56) References Cited

OTHER PUBLICATIONS

Connor, S., "EPIC—Introducing Plessey's multi award winning EPIC Sensor and its many applications", [online]. [retrieved Sep. 20, 2012]. Retrieved from the Internet: <URL:http://www.plesseysemiconductors.com/products/epic/technical/>, 2012, 5 pages.

Connor et al., "EPIC: A New Epoch in Electric Potential Sensing", [online]. [retrieved on Sep. 20, 2012]. Retrieved from the Internet: <URL:http://www.sensorsmag.com/sensors/electric-magnetic/epic-a-new-epoch-electric-potential-sensing-8961>, Sep. 1, 2011, 4 pages.

Ekström et al., "Critical review of non-invasive respiratory monitoring in medical care", Medical & Biological Engineering & Computing, Aug. 2003, pp. 377-383.

Gabriel et al., "The dielectric properties of biological tissues: III. Parametric models for the dielectric spectrum of tissues", Physics in Medicine & Biology, vol. 41, 1996, pp. 2271-2293.

German-Sallo, Z., "Applications of Wavelet Analysis in ECG Signal Processing", PhD. Thesis, Technical University of Cluj-Napoca, 2005, 11 pages.

German-Sallo, Z., "Processing of ECG Signals Using Wavelet Analysis", Acta Electrotechnica, vol. 46(3), 2005, pp. 135-140.

Guha et al., "An 8 GHz CMOS Near Field Bio-sensor Array for Imaging Spatial Permittivity Distribution of Biomaterials", IEEE MTT-S International Microwave Symposium (IMS2014), 2014, pp. 1-4.

Hui et al., "Monitoring vital signs over multiplexed radio by near-field coherent sensing", Nature Electronics, vol. 1, Jan. 2018, pp. 74-78.

Kapusta et al., "Sampling Circuits That Break the kT/C Thermal Noise Limit", IEEE Journal of Solid-State Circuits, vol. 49, No. 8, Aug. 2014, 8 pages.

Malik et al., "Respiration Monitoring Using a Flexible Paper-based Capacitive Sensor", 2018 IEEE, 2018, pp. 1-4.

Nikolopoulos et al., "Auto Reconfigurable Patch Antenna for Biomedical Single Channel Multi-Frequency Microwave Radiometry Applications", Progress In Electromagnetics Research C, vol. 49, 2014, pp. 19-29.

Saritha et al., "ECG Signal Analysis Using Wavelet Transforms", Bulg. J. Phys., 35, 2008, pp. 68-77.

Teichmann et al., "A Bendable and Wearable Cardiorespiratory Monitoring Device Fusing Two Noncontact Sensor Principles", IEEE Journal of Biomedical and Health Informatics, vol. 19, No. 3, May 2015, pp. 784-793.

Teichmann et al., "Noncontact Monitoring of Cardiorespiratory Activity by Electromagnetic Coupling", IEEE Transactions on Biomedical Engineering, vol. 60, No. 8, Aug. 2013, pp. 2142-2152.

Venkataramanan, M., "Biosensor can monitor your heartbeat from a distance", [online]. (c) Copyright Reed Business Information Ltd. [retrieved on Sep. 20, 2012]. Retrieved from the Internet: <URL: http://www.newscientist.com/blogs/onepercent/2011/11/sensor-monitors-your-heartbeat.html>, Nov. 16, 2011, 6 pages.

Yan et al., "Verification of a non-contact vital sign monitoring system using an infant simulator", Con. Proc. IEEE Eng. Med. Biol. Soc. 2009, (Abstract Only), [online]. [retrieved on Sep. 20, 2012]. Retrieved from the Internet: <URL: http://www.ncbi.nlm.nih.gov/pubmed>, 2009, 1 page.

Yan et al., "Verification of a Non-Contact Vital Sign Monitoring System Using an Infant Simulator", Con. Proc. IEEE Eng. Med. Biol. Soc., 31st Annual International Conference of the IEEE EMBS, (Minneapolis, MN, Sep. 2-6, 2009, 2009, pp. 4836-4839.

U.S. Appl. No. 16/139,993, filed Sep. 24, 2018, Langley, II et al.

Office Action received for Korean Patent Application No. 10-2018-7024350, mailed on Aug. 26, 2024, 11 pages (5 pages of English Translation and 6 pages of Official Copy).

Office Action received for Korean Patent Application No. 10-2021-7012074, mailed on Mar. 26, 2025, 11 pages (5 pages of English Translation and 6 pages of Official Language Copy).

U.S. Appl. No. 17/546,679, filed Dec. 9, 2021, Langley, II et al.
U.S. Appl. No. 16/824,182, filed Mar. 19, 2020, Langley, II et al.
U.S. Appl. No. 16/139,933, filed Sep. 9, 2018, Langley, II et al.
U.S. Appl. No. 15/418,328, filed Jan. 27, 2017, Langley, II et al.
U.S. Appl. No. 16/890,970, filed Jun. 2, 2020, Haggis et al.
U.S. Appl. No. 17/930,247, filed Sep. 7, 2022, Howie, et al.
U.S. Appl. No. 17/930,253, filed Sep. 7, 2022, Howie, et al.

* cited by examiner

COMPUTATION OF PARAMETERS OF A BODY USING AN ELECTRIC FIELD

CROSS REFERENCE TO RELATED APPLICATIONS

This application is a continuation-in-part of U.S. patent application Ser. No. 17/546,679, filed Dec. 9, 2021, which is a continuation application of U.S. patent application Ser. No. 16/824,182, filed Mar. 19, 2020, now U.S. Pat. No. 11,253,163, which is a continuation application of U.S. patent application Ser. No. 16/139,993, filed Sep. 24, 2018, now U.S. Pat. No. 10,631,752, which is a continuation-in-part application of U.S. patent application Ser. No. 15/418,328, filed Jan. 27, 2017, now U.S. Pat. No. 10,080,507, which claims the benefit of U.S. Provisional Patent Application No. 62/287,598, filed on Jan. 27, 2016. This application is also a continuation-in-part of U.S. patent application Ser. No. 16/890,970, filed Jun. 2, 2020, which claims the benefit of U.S. Provisional Patent Application No. 62/856,564, filed Jun. 3, 2019. This application also claims the benefit of U.S. Provisional Patent Application No. 63/286,305, filed Dec. 6, 2021, U.S. Provisional Patent Application No. 63/329,709, filed Apr. 11, 2022, and U.S. Provisional Patent Application No. 63/345,581, filed May 25, 2022.

This application incorporates by reference herein for all purposes the following applications in their entireties as though fully disclosed herein, all commonly owned with the instant application not later than the effective filing date of the instant application: U.S. Provisional Patent Application No. 61/693,194, filed Aug. 24, 2012; U.S. patent application Ser. No. 13/841,959, filed Mar. 15, 2013, now U.S. Pat. No. 9,035,778; U.S. patent application Ser. No. 14/528,812, filed Oct. 30, 2014, now U.S. Pat. No. 9,549,682; U.S. Provisional Patent Application No. 62/287,598, filed on Jan. 27, 2016; U.S. patent application Ser. No. 15/418,328, filed on Jan. 27, 2017, now U.S. patent Ser. No. 10/080,507; U.S. patent application Ser. No. 16/139,993, filed on Sep. 24, 2018, now U.S. patent Ser. No. 10/631,752; U.S. patent application Ser. No. 16/824,182, filed on Mar. 19, 2020; U.S. patent application Ser. No. 16/058,821, filed on Aug. 8, 2018, now U.S. patent Ser. No. 11/026,593; U.S. patent application Ser. No. 17/316,131, filed on May 10, 2021; U.S. Provisional Patent Application No. 62/856,564, filed on Jun. 3, 2019; U.S. patent application Ser. No. 16/890,970, filed on Jun. 2, 2020; U.S. Provisional Patent Application No. 63/286,305, filed Dec. 6, 2021; U.S. Provisional Patent Application No. 63/329,709 filed Apr. 11, 2022; and U.S. Provisional Patent Application No. 63/345,581 filed May 25, 2022.

BACKGROUND

Field

Advancements in computations of parameters of a body, such as computation of physiological parameters of a human body, are desired to provide improvements in factors such as one or more of compliance, accuracy, reliability, and usability for nighttime, resting rates of the parameters.

Related Art

Unless expressly identified as being publicly or well known, any mention in the present disclosure of techniques and concepts, including for context, definitions, or comparison purposes, should not be construed as an admission that such techniques and concepts are previously publicly known or otherwise part of the prior art. References cited in the present disclosure (if any), including patents, patent applications, and publications, are hereby incorporated by reference in their entireties, whether specifically incorporated or not, for all purposes.

SUMMARY

Embodiments described herein are implementable in numerous ways, e.g., as a process, an article of manufacture, an apparatus, a system, a composition of matter, and a computer readable medium such as a computer readable storage medium (e.g., media in an optical and/or magnetic mass storage device such as a disk, an integrated circuit having non-volatile storage such as flash storage), or a computer network in which program instructions are sent over optical or electronic communication links. The Detailed Description provides an exposition of one or more embodiments that enable improvements in factors such as one or more of accuracy, compliance, cost, profitability, performance, efficiency, and/or utility of use in the field identified above. The Detailed Description includes an Introduction to facilitate understanding of the remainder of the Detailed Description. The Introduction includes Example Embodiments of one or more of systems, methods, articles of manufacture, and computer readable media in accordance with concepts described in the present disclosure. As is discussed in more detail in the Detailed Description, embodiments described herein encompass numerous possible modifications and variations.

BRIEF DESCRIPTION OF DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1:
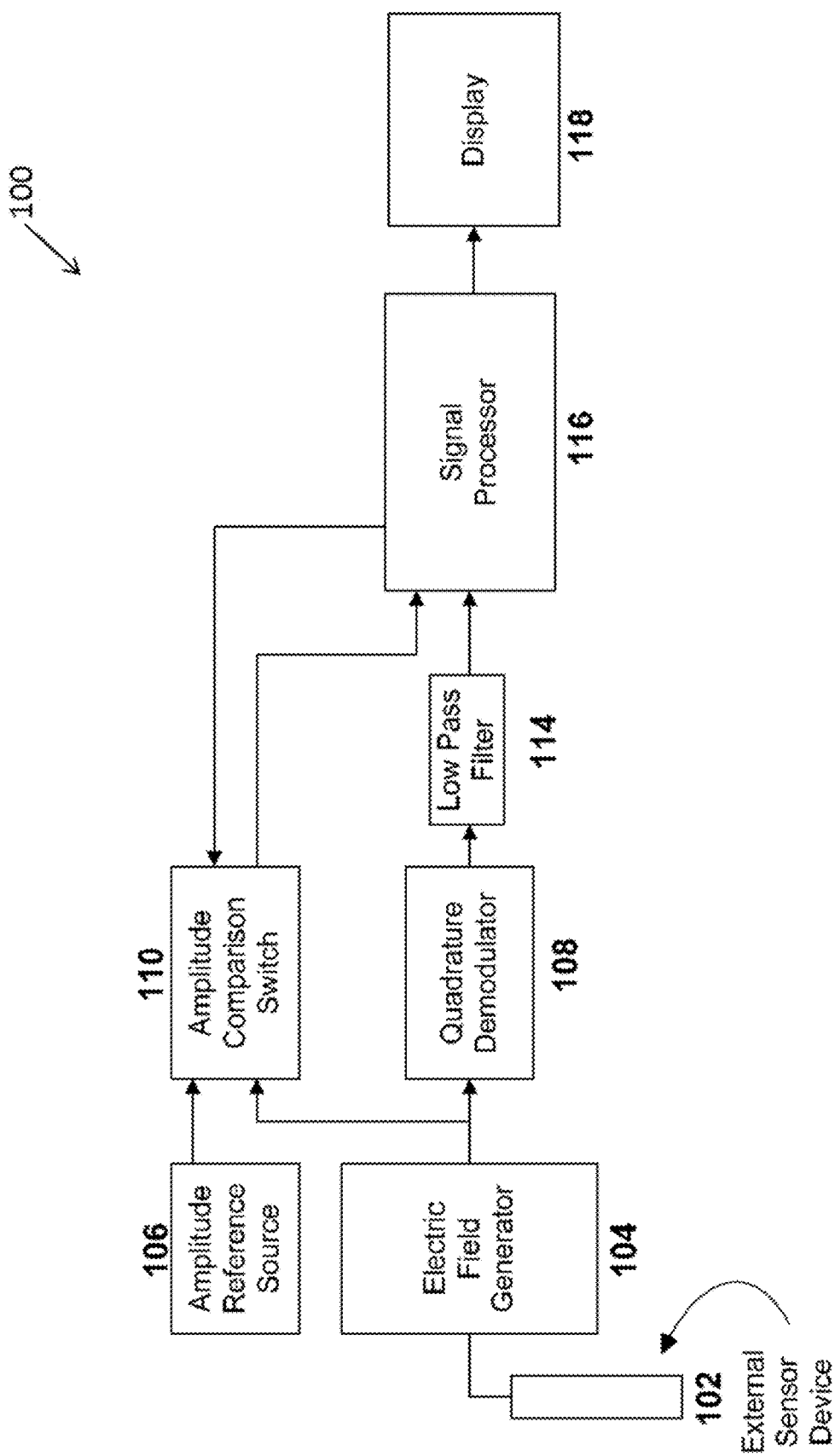
FIG. 1 illustrates an example of selected details of a system for detecting and analyzing changes in a body according to certain embodiments.

A detailed description of one or more embodiments is provided below along with accompanying figures illustrating selected details of the various embodiments. The embodiments in the present disclosure are understood to be examples, the implementations described are expressly not limited to or by any or all of the embodiments in the present disclosure, and the embodiments encompass numerous combinations, alternatives, modifications, and equivalents. To avoid monotony in the exposition, a variety of word labels (such as: first, last, certain, various, further, given, other, particular, select, some, specific, and notable) may be applied to separate sets of embodiments; as used in the present disclosure such labels are expressly not meant to convey quality, or any form of preference or prejudice, but merely to conveniently distinguish among the separate sets. The order of some operations of disclosed processes is alterable within the scope of the embodiments described herein. Wherever multiple embodiments serve to describe variations in process, system, and/or program instruction features, other embodiments are contemplated that, in accordance with a predetermined or a dynamically determined criterion, perform static and/or dynamic selection of one of multiple modes of operation corresponding respectively to one or more of the multiple embodiments. Numerous specific details are set forth in the following description to provide a thorough understanding of the techniques described herein. In various embodiments, different numerical values may be used. The details are provided for the purpose of example and the embodiments may be practiced without some or all of the details. For the purpose of clarity, technical material that is known in the technical fields related to the embodiments has not been described in detail so that the present disclosure is not unnecessarily obscured.

Introduction

This introduction is included only to facilitate the more rapid understanding of the Detailed Description; the introduction is not intended to limit the concepts presented in this disclosure (including explicit examples, if any), as the paragraphs of any introduction are necessarily an abridged view of the entire subject and are not meant to be an exhaustive or restrictive description. For example, the introduction that follows provides overview information limited by space and organization to only certain embodiments. There are many other embodiments and variations thereof, including those to which claims will ultimately be drawn, discussed throughout the balance of the specification.

Many electrical circuits contain antennas and/or antenna-like structures that have the potential to intentionally or unintentionally radiate electric fields (electromagnetic energy) into the environment and/or to couple ambient environmental electromagnetic energy into the electrical circuit. When a body, such as a human body, is in close proximity to such an electrical circuit and close enough to the antennas and/or antenna-like structures, the presence of the body has the potential to influence the nature of the radiated electric field and/or to couple with the electrical circuit. The influence and/or coupling is strongest in what is known as the "reactive near-field" region, in contrast with the "far field" region where the body is only influenced by the radiative effects of the electric field but does not substantially couple with the electrical circuit. In the reactive near-field region, the influence and/or coupling can affect the frequency and/or the amplitude of the electric field generated by the electrical circuit. An example of the reactive near-field is holding a hand near a radio or TV antenna (e.g., rabbit ears)—the coupling of the body into the antenna circuitry changes the capacitance (and/or other parameters) of the circuit demodulating the received antenna signal, and thereby changes the reception.

As a rule of thumb, for electrically-short antennas (antennas whose electrical length is less than one half the wavelength of the frequency being radiated), the reactive near-field is the region near the antenna within $1/(2*\pi)$ of the wavelength of the signal being radiated. For example, at 10 MHz the wavelength is roughly 30 meters, and the reactive near-field is within roughly 4.75 meters of the antenna, and at 30 MHz the wavelength is roughly 10 meters and the reactive near-field is within roughly 1.6 meters of the antenna. The coupling effects are stronger the closer the body is to the antenna, and the coupling effects do not entirely disappear at distances greater than $1/(2*\pi)$ of the wavelength.

The effects of the body on the electric field can be quantitatively approximated by adding to a model of the electrical circuit (including any associated antennas) a model representing an equivalent circuit of the body. In the case of a human body, one example equivalent circuit model comprises time-varying reactive and dissipative impedance components that represent (a) the physiology of the human body, e.g., organs (including muscles, arteries, veins, etc.), other tissues (such as connective, fat and skin tissues), and liquids (such as blood), and (b) the physiological processes associated with a living organism, e.g., respiration, blood circulation, and peristalsis. The values of the time-varying reactive and dissipative impedance components and how they change due to physiological processes are a complex function of multiple factors including the frequency or frequencies being radiated, the type and/or nature of the antennas and/or antenna-like structures (e.g., an actual antenna vs. an unintentional radiator), the dynamic nature of the coupling between the electrical circuit and the human body (e.g., depending on distance and/or orientation of the human body), and the actual physiological parameters of the human body itself (e.g., respiration rate, heart rate, mass, and body mass index (BMI)).

The frequency of the electric field has multiple effects. First, the frequency of the electric field affects how deeply into the body the electric field penetrates (i.e., whether components of the body closer to the surface of the body produce the majority of the effects). Very high (e.g., 10 GHz) frequencies (having very short wavelengths) generally only have effects at or near the surface of a body, while lower frequencies (e.g., 10 MHz with a 30 meter wavelength) penetrate much more deeply. Second, at least in the case of a human body, the electrical properties (e.g., permittivity and/or dissipation factor) of the components of the body (e.g., organs, other tissues, and liquids) are frequency-dependent in differing ways. For example, the variation of the electrical properties of organs with frequency is different from the variation of the electrical properties of tissues with frequency, and thus the effect of organs vs. tissues on the electric field varies with the frequency of the electric field.

In one existing technique, electric fields are used to observe a single organ of the body. In such a technique, small probes are placed very near the heart and are designed to observe that single organ. Such a technique is limited in its applicability and cannot, for example, be used to compute physiological parameters of multiple organs at the same time, or be used in a passive manner to observe physiological parameters of a sleeping human body that may move (e.g., change positions) relative to a stationary probe.

One area of applicability of a device that can compute physiological parameters is to determine nighttime resting respiration rate and/or heart rate. Changes in one or more of these nighttime resting rates over a period of days have been shown to be a good predictor of the onset of, for example, Chronic Obstructive Pulmonary Disease (COPD) exacerbations. Current products that attempt to compute these physiological parameters for a patient have one or more of the following problems:

Require activity of the patient to use (e.g., wear, charge, aim, etc.) the device, leading to a lack of 100% compliance (e.g., accurate computations every night).

Inaccurate computations, even if the patient being observed is relatively still.

Unable to operate through blankets, sheets, nighttime clothes, etc.

Not operable and/or accurate independent of movement of the patient and/or of the position of the patient on a bed (e.g., sleeping on the back, vs. on the side, vs. on the stomach).

Inability to discriminate events, such as the patient changing position (e.g., rolling over) or temporarily getting out of bed.

Inability to produce accurate results in the presence of other bodies, such as a human partner or a pet, in the same bed.

Subject to interference from environmental factors (e.g., a ceiling fan), causing inaccuracy and/or errors.

In various embodiments, the techniques described herein are able to overcome one or more of the above problems.

Overview

While the techniques described herein are sometimes explained using a human body comprising organs, other tissues, and liquids with different electrical properties as an example, the techniques are applicable to computation of parameters of other types of bodies, including other organic bodies (e.g., plants or animals) and inorganic bodies (e.g., mechanical or electrical devices).

In some embodiments, an electric field generator generates an electric field at a nominal frequency and/or with a nominal amplitude. In various embodiments, the nominal frequency is a predefined nominal frequency. In other embodiments, the nominal frequency is statically (e.g., at power-on in response to configuration information) and/or dynamically adjusted. In various embodiments, the nominal amplitude is a predefined nominal amplitude. In other embodiments, the nominal amplitude is statically and/or dynamically adjusted.

The electric field is radiated through an antenna, such as a two-wire antenna, and interacts with a body (such as a human body) in the reactive near-field region of the electric field. A detector observes the electric field as it varies (due to coupling of the body with the electric field generator) and measures the electric field's frequency and/or amplitude. From the frequency and/or the amplitude measurements, one or more parameters of the body are computed. In various embodiments and/or usage scenarios, a change in the frequency and/or the amplitude of the electric field is indicative of a parameter of the body. For example, an industrial application is able to use an electric field to measure the thickness of glass. In other embodiments and/or usage scenarios, the one or more parameters of the body (such as physiological parameters of the human body) are computed, such as by determining one or more respective periodicities (periodic behavior patterns) in the frequency and/or the amplitude measurements. A physiological parameter of the human body includes, for example, a rate of a physiological process (e.g., a respiration rate or a heart rate), a waveform indicating behavior of a physiological process (e.g., a respiratory waveform), a measurement of a part of the human body (e.g., a mass or a body mass index), etc. In further embodiments, the computed physiological parameters are tracked over time (e.g., over days, weeks, months, or years) to determine changes and/or trends.

While the electric field is generated at the nominal frequency, interactions of the body with the electric field generator, such as due to coupling in the reactive near-field region of the electric field, cause the frequency and/or the amplitude of the electric field measured by the detector to change. In other words, when a body is present in the reactive near-field region of an electric field, one or more properties of the generated electric field change (e.g., when compared to an electric field generated at the nominal frequency and/or at the nominal amplitude without a body present in the reactive near-field region) as a result of the coupling between the electric field and the body. In a first example, permittivity of the body changes the effective capacitance of a circuit used by the electric field generator due to the coupling, and thus affects the frequency. In a second example, the dissipation factor of the body changes the effective load resistance of a circuit used by the electric field generator due to the coupling, and thus affects the amplitude. Further, if the body as a whole, or internal portions of the body (e.g., organs, other tissues, or liquid in a human body) are in motion, the permittivity and/or dissipation factor change dynamically in response to the motion.

In some embodiments, two or more antennas are used to provide spatial and/or frequency diversity. In a first example, two antennas are used and the one of the two antennas which exhibits the strongest coupling of the body to the electric field generator is used for the computation of the one or more parameters of the body. In a second example, both antennas are used and their signals are combined (such as with respective weighting factors according to respective signal quality measures) so as to improve the computation of at least one of the one or more parameters of the body. In a third example, two or more antennas cover different regions of a bed in order to isolate the effects of two or more bodies on the bed and/or to provide sensing coverage over a larger portion of the bed. The two or more antennas are usable to improve the computation of the one or more parameters of one of the bodies on the bed, and/or to separately compute respective one or more parameters of each of the bodies on the bed.

In various embodiments, one or more techniques are used to improve the computation of the one or more parameters, such as controlling the electric field generator to adjust the frequency and/or the amplitude of the electric field. In a first example, adjusting the frequency of the electric field maintains the electric field at or near (e.g., within a few percent of) the nominal frequency. In a second example, adjusting the frequency of the electric field improves the quality measure (e.g., the signal-to-noise ratio) of the one or more parameters of the body (e.g., a degree to which the one or more parameters affect the frequency of the electric field). In a third example, adjusting the amplitude of the electric field compensates for effects of the body being too close to or too far from the antenna.

In some usage scenarios, movement of the body with respect to a stationary antenna radiating the electric field causes a disturbance in the electric field that creates inaccuracies in the computation of the one or more parameters. In a first example, movement of a human body (e.g., rolling over) perturbs the coupling of the human body to the electric field generator, creating inaccuracies in the computation of a physiological parameter of the human body. In a second example, a pet jumping onto a bed perturbs the coupling of a human body to the electric field generator, creating inaccuracies in the computation of a physiological parameter of the human body. In some embodiments, blanking techniques detect such disturbances and eliminate a portion of the frequency and/or the amplitude measurements of the electric field from consideration in the computation of the one or more parameters.

Body Parameter Computing Device (BPCD)

In some embodiments, a Body Parameter Computing Device (BPCD) is used to compute and store and/or communicate one or more parameters of one or more bodies being evaluated. The BPCD is a non-contact device that uses measurements of electric fields interacting with the one or more bodies to compute the one or more parameters of the one or more bodies. In some embodiments, the BPCD is a single device located at a single location. In other embodiments, the BPCD comprises multiple devices, such as front-end circuitry (e.g., analog front-end circuitry) and back-end circuitry (e.g., computation and/or processing circuitry), that are optionally and/or selectively co-located. In further embodiments, one or more portions of the BPCD (e.g., the computation and/or processing circuitry) resides in the "cloud" (e.g., on a server reachable over a network) and/or in multiple remote devices.

For a human body, the BPCD has applications to one or more of: computing physiological parameters (e.g., heart rate, respiration rate, lung expansion profile, mass, and/or BMI) of the human body; and using the computations of the physiological parameters to detect one or more symptoms and/or to predict one or more conditions and/or the onsets of those conditions. Examples of symptoms include congestion of the lungs, frequency of coughing, irregular heartbeat, a change in heart rate variability, edema, a change in an amount of blood flow to a specific organ, etc. Examples of conditions include Chronic Obstructive Pulmonary Disease (COPD) exacerbations, heart disease or other heart conditions (e.g., Congestive Heart Failure (CHF), myocardial infarction, myocarditis, etc.), aneurysms, pulmonary embolisms, hematomas, strokes, sepsis, renal disease or failure, infections (e.g., urinary tract infections, pneumonias, abscesses, etc.), tumors (including malignant cancers and benign tumors), healing of an injury (predicted from an increased amount of blood flow to a specific organ, and other illnesses and diseases.

Figure 4:
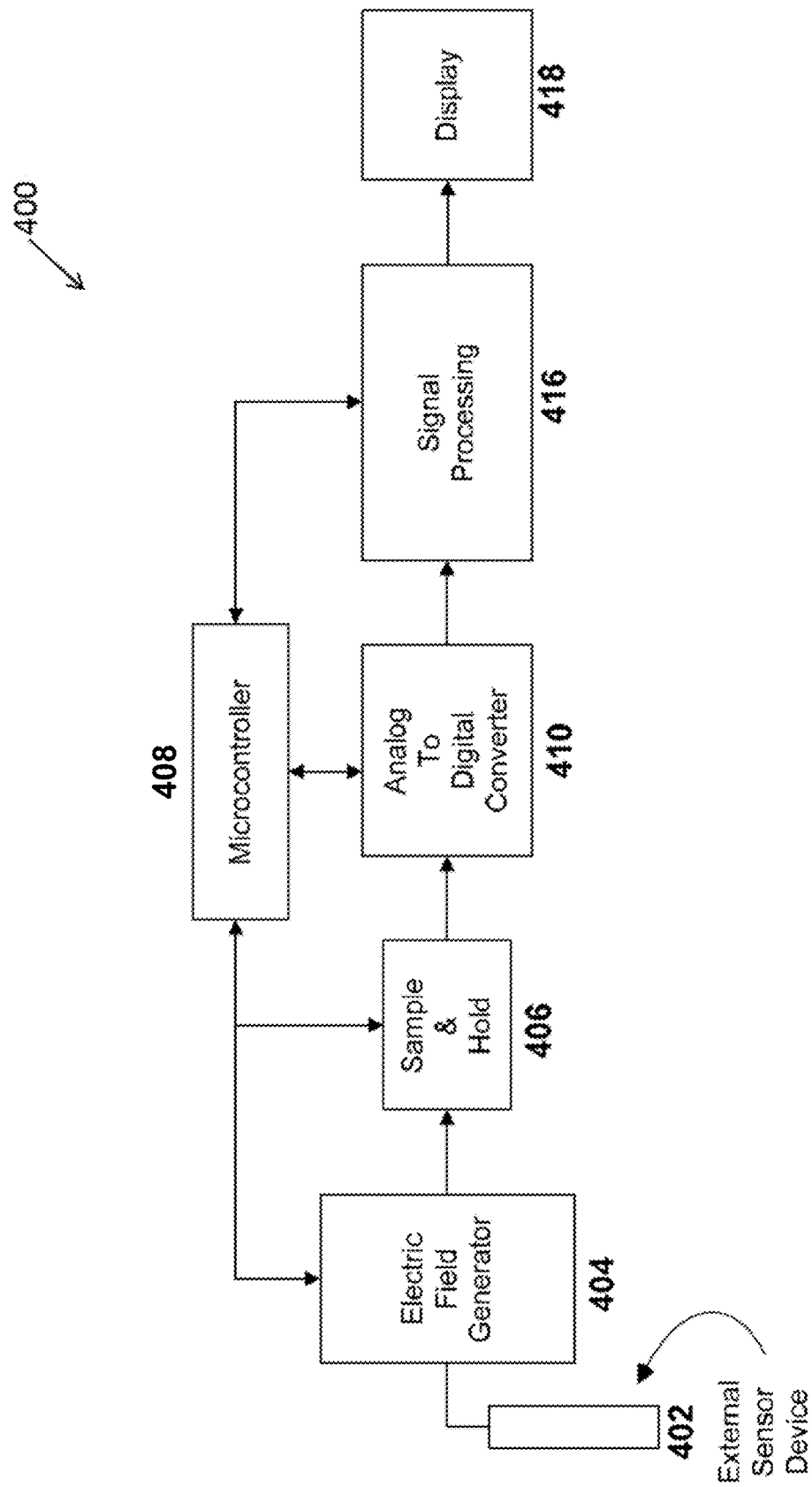
FIG. 4 illustrates an example of selected details of a system for detecting and analyzing changes in a body according to certain embodiments.
Figure 8:
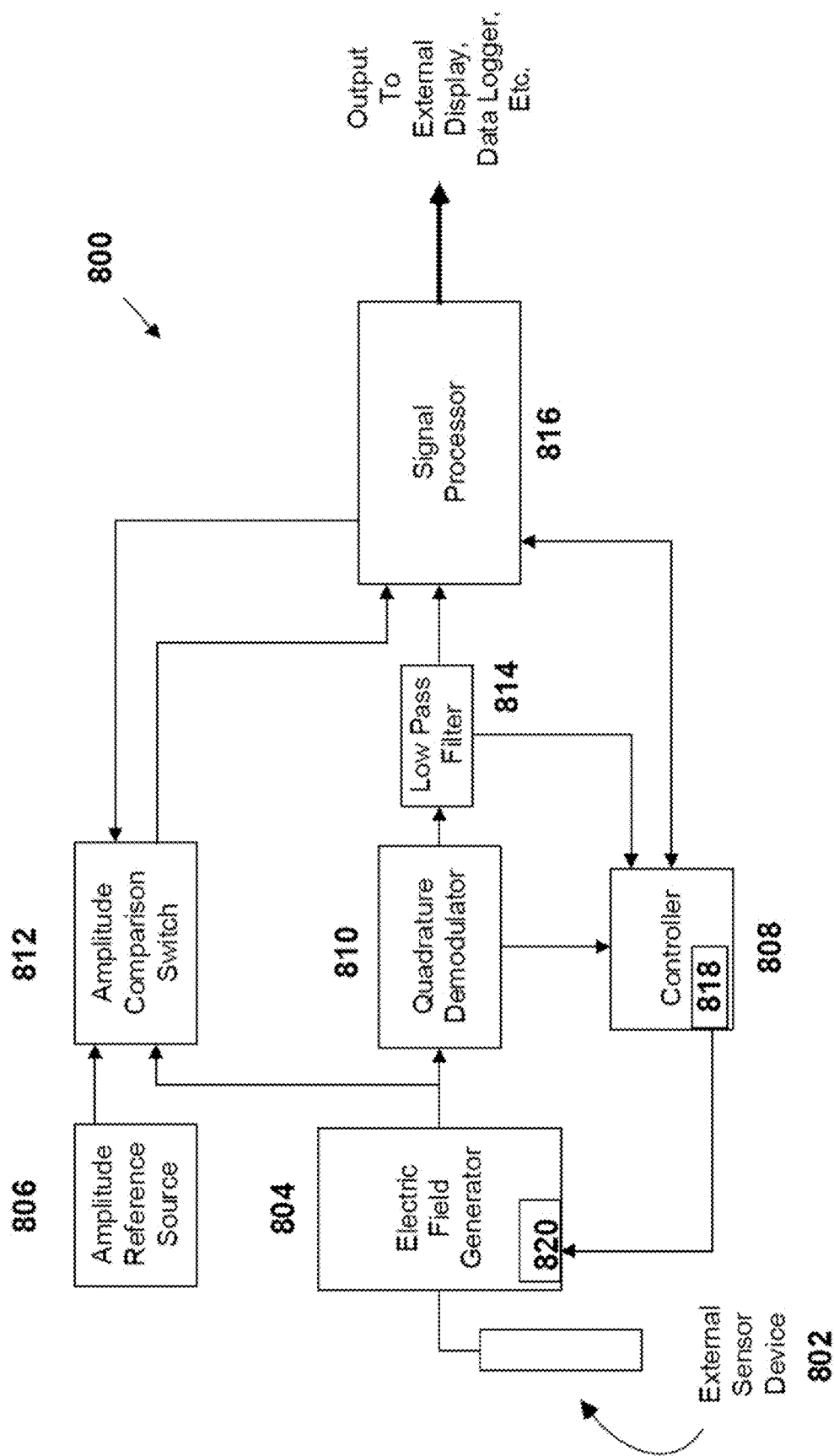
FIG. 8 illustrates an example of selected details of a system for detecting and analyzing changes in a body according to certain embodiments.
Figure 9:
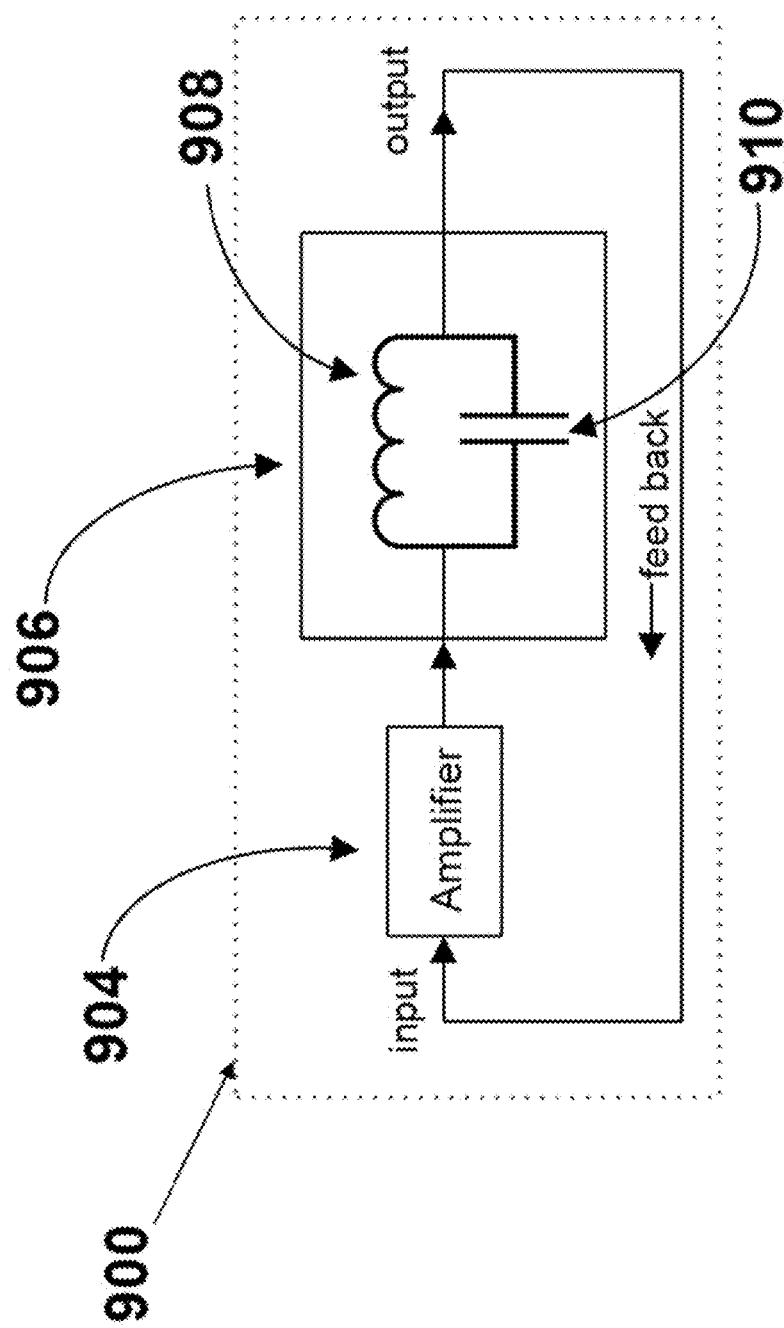
FIG. 9 illustrates an example of selected details of an inductor-capacitor (LC) tank oscillator according to certain embodiments.
Figure 11:
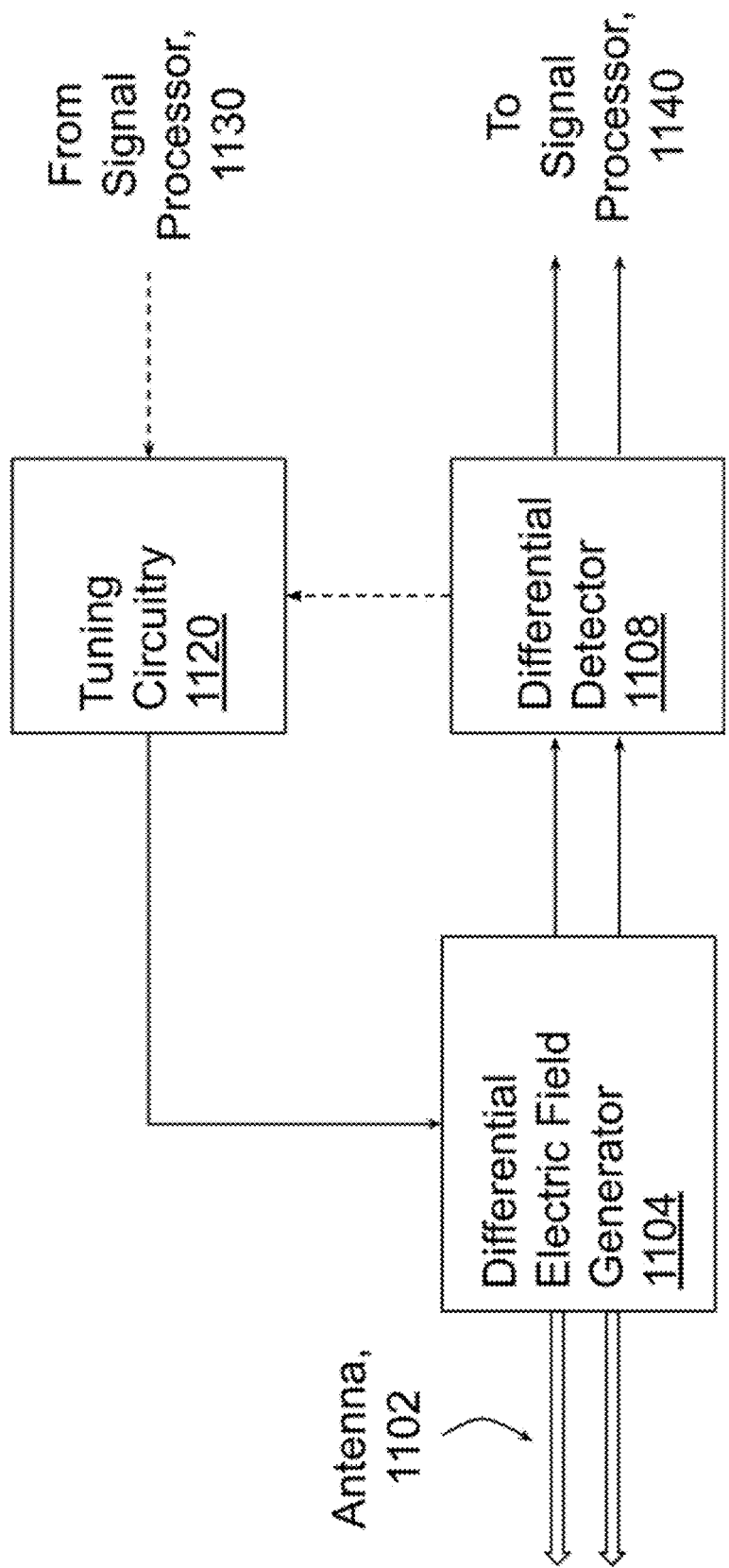
FIG. 11 illustrates an example of selected details of an embodiment of a portion of a system for detecting and analyzing changes in a body according to certain embodiments.

FIGS. 1, 4, 6, 7, 8, 9, 11, 12, and 16 illustrate examples of selected details of systems comprising a BPCD or portions of such systems. In various embodiments, the BPCD comprises one or more of:

One or more electric field generators to generate respective electric fields at respective nominal frequencies with respective nominal amplitudes. (For example, electric field generator 104 as illustrated in FIG. 1, electric field generator 404 as illustrated in FIG. 4, electric field generator 804 as illustrated in FIG. 8, or differential electric field generator 1104 as illustrated in FIG. 11. FIG. 9 illustrates a Colpitts oscillator 900 that is usable in an electric field generator.)

One or more antennas to radiate the respective electric fields. (For example, external sensor device 102 as illustrated in FIG. 1, external sensor device 402 as illustrated in FIG. 4, external sensor device 802 as illustrated in FIG. 8, or antenna 1102 as illustrated in FIG. 11.)

Figure 7:
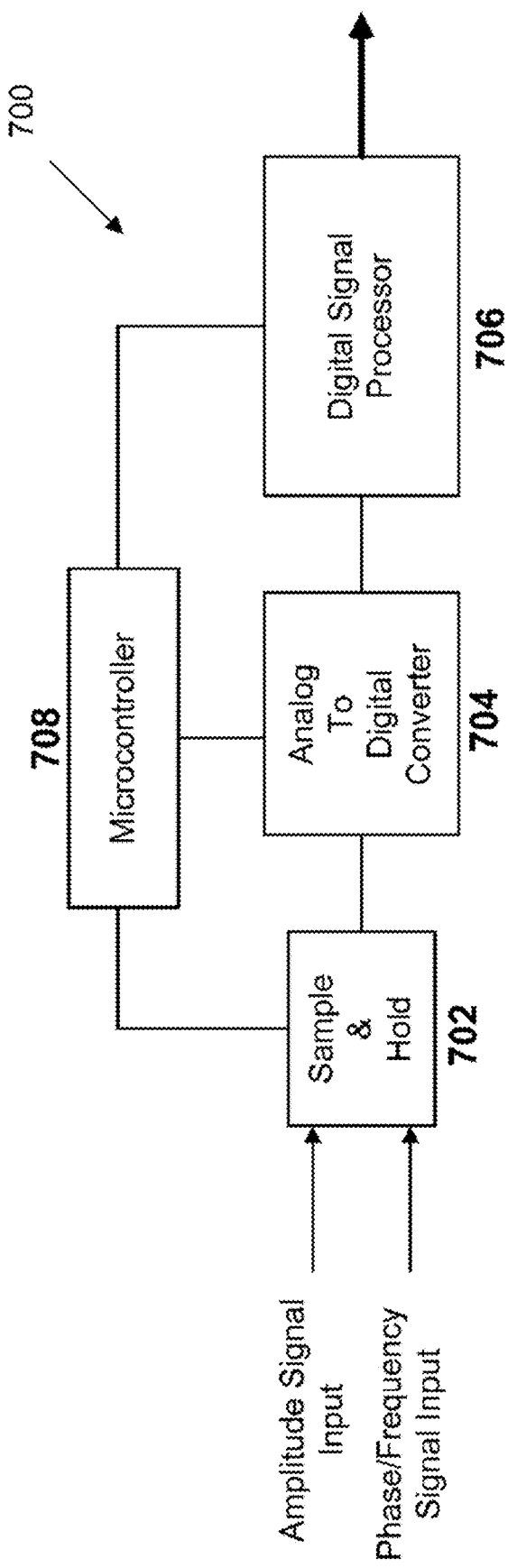
FIG. 7 illustrates an example of selected details of a signal processor according to certain embodiments.

One or more detectors to measure the frequency and/or the amplitude of the respective electric field as affected by coupling between the one or more bodies and the one or more electric field generators. (For example, amplitude comparison switch 110 and/or quadrature demodulator 108 optionally and/or selectively with low pass filter 114 as illustrated in FIG. 1, amplitude comparison switch 812 and/or quadrature demodulator 810 optionally and/or selectively with low pass filter 814 as illustrated in FIG. 8, sample-and-hold device 406 and ADC (analog-to-digital converter) 410 optionally and/or selectively with microcontroller 408 as illustrated in FIG. 4, sample-and-hold circuit 702 and ADC 704 optionally and/or selectively with microcontroller 708 as illustrated in FIG. 7, or differential detector 1108 as illustrated in FIG. 11.)

One or more computation units to process the detector measurements and compute the one or more parameters of the one or more bodies. (For example, signal processor 116 as illustrated in FIG. 1, digital signal processor 416 as illustrated in FIG. 4, digital signal processor 706 as illustrated in FIG. 7, or signal processor 816 as illustrated in FIG. 8.)

One or more tuners to adjust the respective frequencies and/or to maintain a target frequency (e.g., the nominal frequency) as the coupling between the one or more bodies and the one or more electric field generators varies. (For example, tuner 820 optionally and/or selectively with controller 808 and/or adjuster 818 as illustrated in FIG. 8, or tuning circuitry 1120 as illustrated in FIG. 11.)

One or more Automatic Gain Control (AGC) circuits to adjust the respective amplitudes. (For example, in various embodiments, an AGC is part of amplitude reference source 106 as illustrated in FIG. 1, and/or amplitude reference source 806 as illustrated in FIG. 8.)

Figure 12:
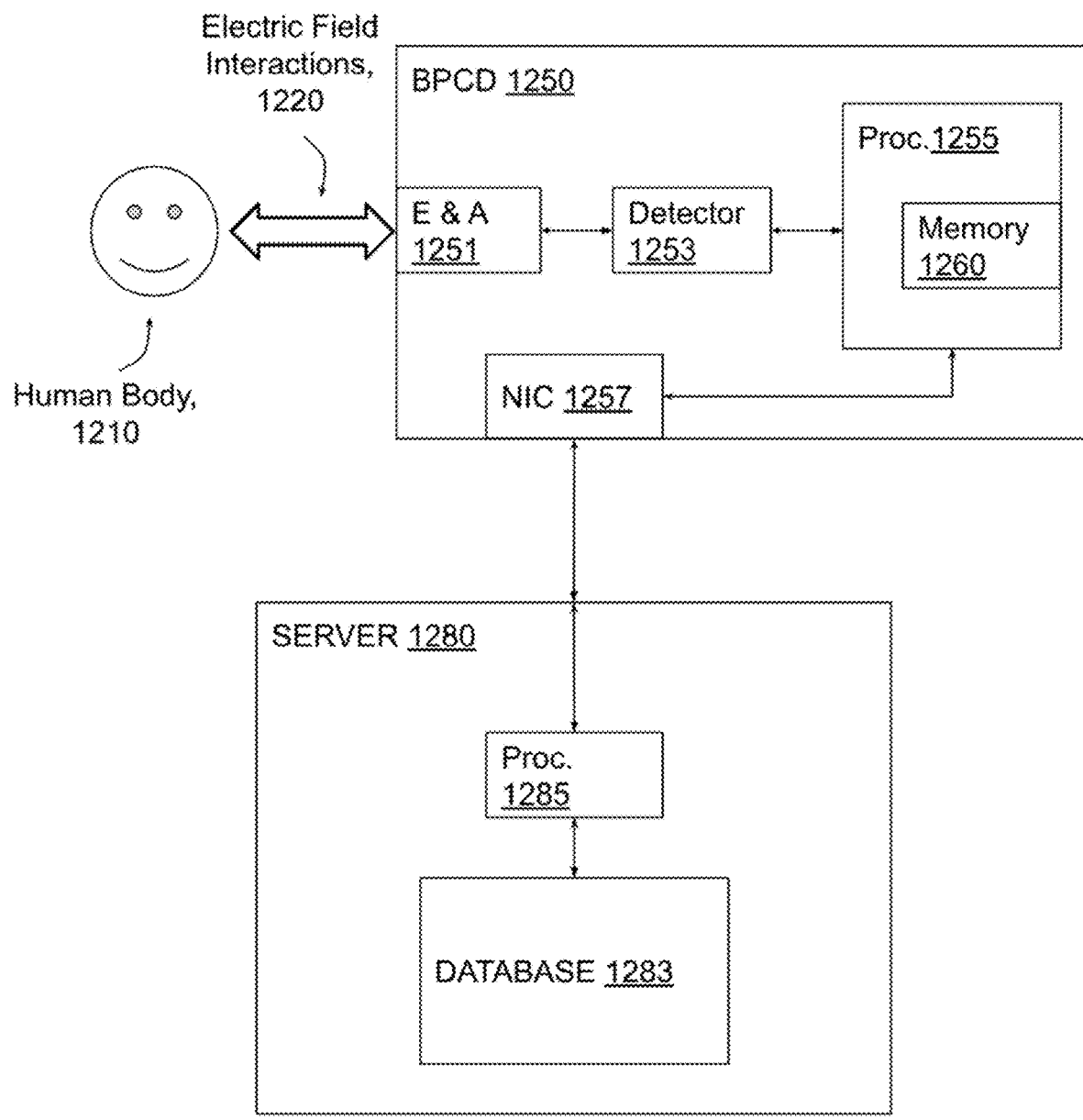
FIG. 12 illustrates an example of a system comprising a Body Parameter Computing Device (BPCD) and a server.
Figure 16:
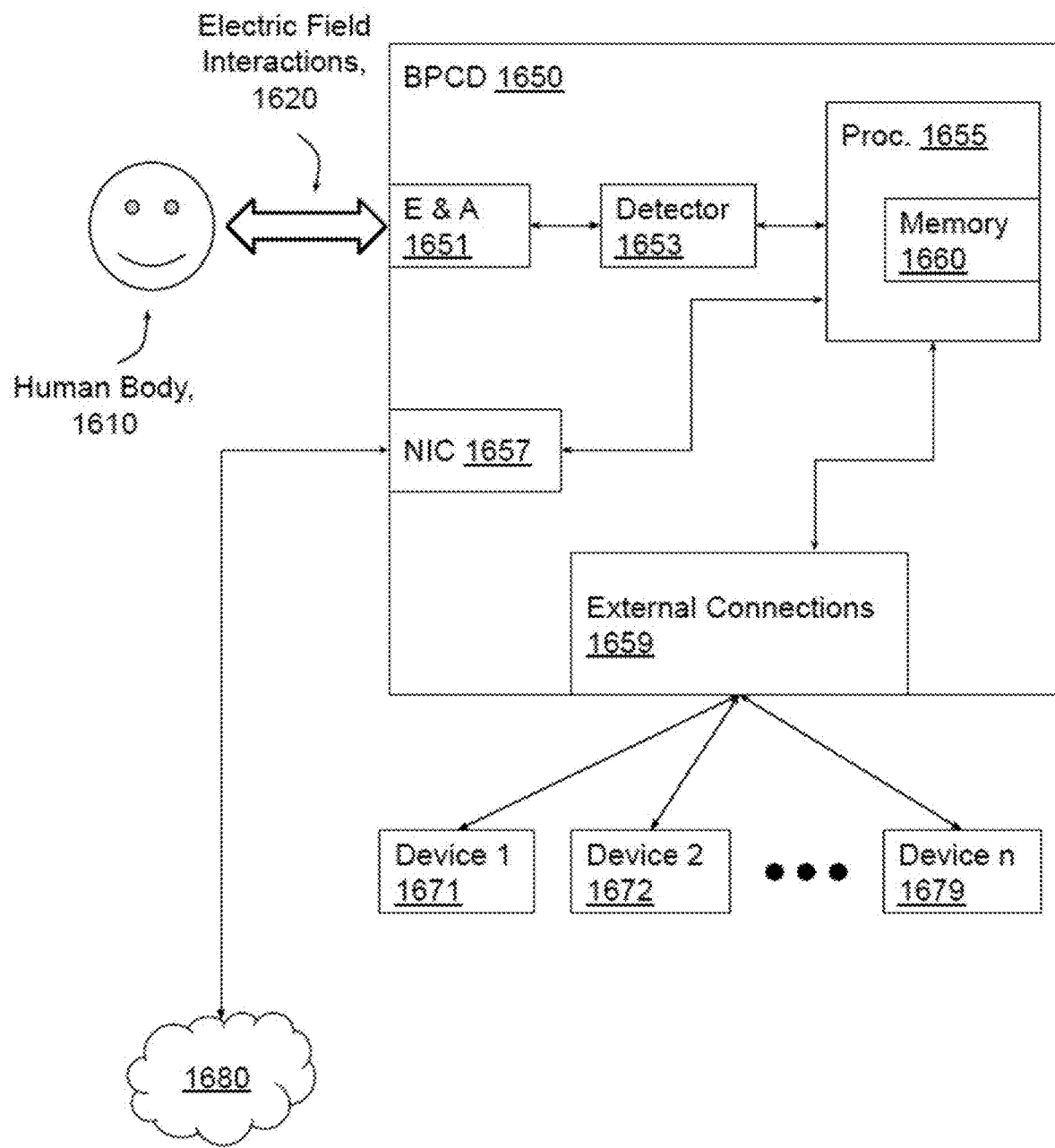
FIG. 16 illustrates an example of a system comprising a Body Parameter Computing Device (BPCD) acting as a hub for one or more other devices according to certain embodiments of the present disclosure.

Storage, such as volatile and/or non-volatile storage to store data, such as programs used by the one or more computation units, measurements produced by the one or more detectors, and the one or more parameters of the one or more bodies computed by the one or more computation units. (For example, memory 1260 as illustrated in FIG. 12, or memory 1660 as illustrated in FIG. 16.)

Display circuitry, such as a touchscreen. (For example, display 118 as illustrated in FIG. 1, or display 418 as illustrated in FIG. 4.)

Communication circuitry, such as network communication circuitry, to communicate results (such as the one or more parameters of the one or more bodies) and/or status, and for maintenance and diagnostics. (For example, Network Interface Card (NIC) 1257 as illustrated in FIG. 12, or Network Interface Card (NIC) 1657 as illustrated in FIG. 16.) (While the term "card" is used, there is no implication that the network interface has any particular physical implementation. For example, in some embodiments, the NIC is a Network Interface Chip.)

One or more external connections providing connectivity to other devices. (For example, external connections 1659 as illustrated in FIG. 16.)

The BPCD has many different applications, even in just the realm of measuring parameters of living bodies (e.g., for medical diagnostics, health evaluation, fitness, etc.). In a first example, the BPCD is able to compute the rates of movement of one or more organs of a living body, such as the heart rate and/or the respiration rate, by measuring the effects of the movement of the one or more organs on the electric field. Continuing the first example, measuring nighttime resting heart rate and/or respiration rate can be a predictor of a disease and/or onset of a condition related to a disease, such as COPD or CHF. In a second example, the BPCD is able to use measurements of nighttime heart rates, nighttime respiration rates, and nighttime movement to enable analysis of sleep stages. In a third example, the BPCD is able to compute the heart rate of a human body in a sitting position by, for example, measuring an effect of the femoral artery on the electric field. Continuing the third example, the heart rate measured in a sitting position has applications to driver alertness (where excessive upper body motion may be common), and to patients who are sitting up (rather than lying down) in a hospital bed. The effect of the femoral artery on the electric field is due, at least in part, to movement of the femoral artery including movement of blood (e.g., a pulse wave) in the femoral artery.

In various embodiments, a nighttime resting rate of a physiological parameter of a human body, such as a nighttime resting heart rate or a nighttime resting respiration rate, refers to one or more of: an average rate of the physiological parameter during periods in which the human body is at rest and/or asleep; an average rate of the physiological parameter during periods in which the human body is determined to be in a specific sleep state, such as a deep sleep state; a lowest point in the average rate of the physiological parameter during the nighttime, where averaging, such as rolling averaging, is performed over intervals such as one minute, three minutes, five minutes, or ten minutes; a series of average rates, such as rolling averages computed over an interval, of the physiological parameter during the nighttime; any other function indicating the nighttime behavior of the physiological parameter; and any combination of the foregoing. In further embodiments, the term "nighttime" does not exclusively refer to hours when the sun is down, but is intended to refer to periods of time during which the human body is in bed (or on some other structure) for any purpose, such as rest, sleep, observation, and/or any other state of reduced activity (e.g., coma). Accordingly, a "nighttime" resting rate includes any resting rate as described herein.

In some embodiments, a BPCD is operable to perform measurements more or less continuously (e.g., throughout a 24-hour day and/or for multiple days). In other embodiments, the BPCD is operable to perform measurements during certain hours of the day and/or based on a schedule (e.g., when a factory is operational, or when a human body is expected to be in bed). In further embodiments, the BPCD is operable to perform measurements when enabled, such as when turned on by a person, or when instructed to start taking measurements by a command sent over a network. In any one or more of these various embodiments, measurements of the frequency and/or of the amplitude of the electric field are gathered at a succession of time points during which the BPCD is operable to perform measurements (e.g., during a measuring period). In various embodiments, the frequency and/or amplitude of the electric field change over time due at least in part to interactions with a human body subject to the electric field (e.g., in the reactive near-field region of the electric field). In various embodiments, a computation unit computes, for any one or more internal components of the human body and using each of multiple computation points (e.g., corresponding to the measurement time points or corresponding to an averaging period or a sliding window duration) during the measuring period, a rate of movement of the internal component according to a respective periodic (including quasiperiodic) behavior in the measured frequency. In some embodiments, the rate of movement of any of the one or more internal components at the multiple computation points are used to predict a condition of the human body.

A granularity of the succession of time points is, according to various embodiments, anywhere from microseconds to hours, depending, for example, on the application of the BPCD. Further, while the succession of time points are monotonic in time, they are not necessarily evenly spaced. In a first example, there are "jumps" in time representing periods when the BPCD is not operable to perform measurements. In a second example, the granularity of the succession of time points is dynamically changed, such as when a period with a relatively low rate of change in the frequency and/or the amplitude is determined, or when measurements of the frequency and/or the amplitude are less critical to computing overall statistics. Continuing the second example, if the BPCD determines that a human body whose physiological parameters were being computed is no longer present in the electric field (such as by determining a change in the measured amplitude), a granularity of the succession of time points is decreased until the human body returns.

Physiological Parameters

In some embodiments, a BPCD, via measurements of an electric field interacting with a human body, is enabled to compute one or more physiological parameters of the human body. (The term "physiological parameters" is used to refer to any quantification of an activity or a state of the human body, including normal activities such as heart rate, abnormal activities such as coughing or sneezing, other bodily activities such as movement, and/or body states such as BMI or weight.) By analyzing the phase, frequency and/or amplitude of the electric field, the BPCD is able to determine periodic (including quasiperiodic) and/or non-periodic behaviors of the human body. Examples of periodic behavior include respiration (e.g., lung and/or chest movement), and heartbeats (e.g., heart and/or blood movement). Examples of non-periodic behavior include movement of a limb of the body or other motions of the human body (e.g., arm motion, rolling over, and/or getting out of a bed or chair), and non-periodic respiratory events (e.g., coughing, sneezing, and hiccupping). From the determination of the periodic and/or the non-periodic behavior, the BPCD is enabled to compute one or more physiological parameters of the human body, such as a heart rate, a respiration rate, frequency of coughing, and/or a number of occurrences (over an interval) of a type of movement (e.g., a number of occurrences of getting out of bed, or a number of occurrences of rolling over in bed).

In some embodiments, determining the periodic behavior includes determining a repeating pattern in the phase, frequency, and/or amplitude of the measurements of an electric field. In further embodiments, one or more overlapping repeated patterns are determined (e.g., one pattern for respiration and one pattern for heartbeats).

In some embodiments, determining the non-periodic behavior includes determining an abrupt change in measurements of the phase, frequency, and/or amplitude of the electric field, and/or determining a disruption in the periodic behavior. For example, a detector (e.g., a differential detector) measures an amplitude of an electric field generated by an electric field generator. According to the measured amplitude, a computation unit of the BPCD determines one or more non-periodic behaviors. In further embodiments, the BPCD is enabled to use the determination of the non-periodic behavior to improve accuracy of computation of the one or more physiological parameters of the human body, the detection of one or more symptoms of conditions of the human body, and/or the prediction of one or more conditions of the human body. In a first example, determining a non-periodic behavior such as a cough (determined, for example, as a particular respiratory waveform pattern) enables the BPCD to not consider a portion of the measurements (e.g., the non-periodic behaviors) of the electric field as suitable for some computations (e.g., for respiration rate or other periodic behaviors). In a second example, computing a rate of occurrence (over a measurement interval, such as a number of hours) of a non-periodic behavior such as a cough indicates an occurrence of a symptom of the human body (such as congestion of the lungs). In a third example, computing a rate of occurrence (over a measurement interval, such as a number of hours) of a non-periodic behavior such as a breathing disruption indicates a symptom of the human body, such as sleep apnea. In a fourth example, computing a number of occurrences (over a measurement interval, such as nighttime) of the human body leaving the vicinity of the electric field indicates a symptom of the human body, such as a frequency of a need to urinate. In a fifth example, determining a degree of absorption of the electric field by the human body (e.g., from the amplitude of the electric field) is indicative of weight of the human body. While the degree of absorption is also dependent on other factors, such as position of the human body relative to the electric field, as with nighttime resting heart rate, a nighttime resting degree of absorption is computable.

In some embodiments, computing the physiological parameter includes computing a function of the periodic and/or non-periodic behavior, such as an average (over some period of time, e.g., a specified number of seconds, minutes, hours, or days), a long-term average (e.g., an average, over a longer period, of averages over shorter periods, optionally with determined gaps for non-periodic behavior), or a standard deviation. In a first example, a BPCD computes a short-term average heart rate, such as by determining, over a first measurement interval (e.g., one minute), the number of peaks of the heartbeat effect observed in the measurements of the electric field. Continuing the first example, the BPCD computes a heart rate variability by determining durations of individual heartbeats, such as by determining, within a second measurement interval (e.g., five minutes, a day, a period of days, etc.), the time of occurrence of the peaks of the heartbeat effect and computing a standard deviation of the durations. Further in the first example, the BPCD computes a resting heart rate (such as a nighttime resting heart rate) by observing over a third measurement interval longer than the first measurement interval when the short-term average heart rate has reached a relative minimum value for a number of successive measurements. In a second example, the periodic behavior is a superposition of multiple sources, such as a heartbeat waveform and a respiration waveform. The BPCD is able to separate the sources (such as by frequency filtering) to compute a separate waveform for each of the sources, such as a respiration waveform and a heartbeat waveform.

In various embodiments, the BPCD is enabled to compute, as a function of a function of the periodic and/or non-periodic behavior, one or more physiological parameters of the human body, such as: heart rate, respiration rate; respiratory waveform (e.g., the amount and rate of chest inflation and deflation); weight gain (e.g., due to edema); sleep patterns (e.g., a duration of and/or a number of times the human body is in rapid eye movement (REM) sleep); frequency of coughing, sneezing, hiccupping, and/or other breathing disruptions; a frequency, duration and/or an amount of a type of movement (e.g., restlessness while sleeping, or a change in behavior getting into or out of bed); any other physiological parameter of the human body observable via measurements of the electric field; computation of any of the foregoing over respective one or more intervals; variability (e.g., standard deviation) and/or any other function of any of the foregoing; changes in any of the foregoing over a period of time (e.g., over days or weeks); and any combination of the foregoing. In some embodiments, the one or more physiological parameters of the human body are used to detect one or more symptoms of one or more conditions of the human body and/or predict one or more conditions the human body, such as a condition of having a disease, a symptom of the onset of disease, or a symptom of a disease.

In various embodiments, the BPCD is enabled to use machine learning models and/or neural networks (e.g., convolutional neural networks or recurrent neural networks) that are trained to classify the measurements of the phase, frequency, and/or amplitude of the electric field and/or statistically processed versions of the measurements of the phase, frequency, and/or amplitude of the electric field to determine any of the periodic and/or non-periodic behaviors, to compute any of the physiological parameters of the human body, to detect any of the symptoms, and/or to predict any of the conditions. In further embodiments, training the machine learning model and/or neural network uses a script executed by test subjects to produce measurements of the electric field containing the desired periodic and/or non-periodic behaviors at known times and/or for known durations.

In some embodiments, the BPCD is enabled to detect, from the one or more physiological parameters, one or more symptoms (of one or more conditions) of the human body, such as symptoms of one or more of: Chronic Obstructive Pulmonary Disease (COPD) exacerbations; Congestive Heart Failure (CHF); atrial fibrillation or other irregular heartbeat; breathing disorders (e.g., congestion or apnea); alertness (e.g., not falling asleep); edema; and symptoms of many other conditions. In further embodiments the BPCD is enabled, using the detected symptoms, to predict a condition (or the onset thereof) of the human body.

As one example of use of a BPCD, consider early detection of Chronic Obstructive Pulmonary Disease (COPD) exacerbations (worsening in airway function and respiratory symptoms over a period of days). There is no current "gold standard" for predicting COPD exacerbations, though a patient questionnaire—the COPD Assessment Test™ (CAT)—has been shown to have some predictive value. The CAT is filled out by patients daily; eight different questions are scored on a zero to five scale, and the overall score is indicative of the patient's quality of life. By observing increasing scores, the CAT has been shown to be able to predict COPD exacerbations relatively reliably up to five days in advance. (The same study that showed the relationship between CAT scores and COPD exacerbations also showed a stronger relationship between changes in nighttime resting heart rate and COPD exacerbations.) But the CAT has issues in its use as a COPD exacerbation predictor. First, it is subjective. Second, it requires full (e.g., 100%) patient compliance, which is difficult to achieve other than in specially arranged clinical trials. A BPCD is able to answer some of the same questions as the CAT (e.g., presence of cough, sleep patterns, and/or presence of phlegm through change in lung capacity), to compute physiological parameters (e.g., resting heart rate and/or resting respiration rate) repeatedly during a monitoring period (e.g., several days), and to do so with 100% compliance (assuming the patient simply sleeps in a bed where the BPCD is installed). Because of this, the BPCD is known to be at least as good a predictor of COPD exacerbations as the CAT based on use of heart rate alone as a predictor. By combining various physiological parameters of the human body, the BPCD is believed to be a better predictor of COPD exacerbations than the CAT. In particular, by monitoring (over a period of days) physiological parameters (e.g., at nighttime) and detecting changes thereof, such as changes in heart rate, changes in respiration rate, changes in respiratory waveform (including a rate and/or volume of respiration), frequency of cough, changes in nighttime movement (e.g., restlessness), changes in behavior in getting into or out of bed, and changes in sleep patterns (such as an amount and/or frequency of REM sleep), the BPCD is able to predict a condition of the human body (e.g., the onset of a COPD exacerbation) up to a week or more in advance of the exacerbation becoming critical. In various embodiments, changes in respiratory waveform over a period of days are used, in combination with other physiological parameters, to predict the onset of a COPD exacerbation. For example, increases in slope of the rise of the respiratory waveform (e.g., faster inhalation), decreases in slope of the fall of the respiratory waveform (e.g., slower exhalation), decreases in amplitude of the respiratory waveform, decreases in volume of respiration (the area under one cycle of the respiratory waveform), increased variability in respiration (e.g., more coughing, intermittent gasping for breath), and/or increases in a nighttime resting heart rate (e.g., by at least two standard deviations) are, alone or in combination, used as factors in predicting the onset of a COPD exacerbation.

Electric Field Generator

In some embodiments, an electric field generator generates an electric field at a nominal frequency and/or with a nominal amplitude, such as 26 MHz and 2.75 Volts, or 21 MHz and 1.0 Volts. The nominal frequency and the nominal amplitude are the frequency and amplitude generated by the electric field generator when there is no external coupling (e.g., due to objects and/or bodies in the reactive near-field region of the electric field). In some embodiments, the nominal frequency and/or the nominal amplitude are a design property of circuitry of the electric field generator. In various embodiments, the nominal frequency and/or the nominal amplitude are configured initially, such as at power-on of a BPCD containing the electric field generator. In further embodiments, the nominal frequency and/or the nominal amplitude are dynamically adjusted, such as by a tuner, as explained in more detail below.

In some embodiments, the electric field is generated using circuitry such as an inductor-capacitor oscillator, a tank oscillator, a resistor-capacitor oscillator, a resonator (such as a narrowband resonator), or any other type of oscillatory circuit configured to be responsive to reactive near-field coupling effects. In further embodiments, the electric field is generated by circuitry, such as phase-shift circuitry, connected to a fixed frequency circuit such as a crystal oscillator. In various embodiments, the electric field generator comprises a differential oscillatory circuit, such as a differential tank oscillator. In further embodiments using a differential oscillatory circuit, the differential oscillatory circuit radiates the electric field via a differential antenna (as illustrated by antenna 1102 in FIG. 11), enabling a use of differential detection circuitry (to measure frequency and/or amplitude of the electric field) so as to be far less sensitive to (e.g., to reject) common-mode noise (e.g., a person walking near the BPCD).

Using a frequency under 30 MHz advantageously avoids FCC regulations applicable to frequencies 30 MHz or higher, though the techniques described herein are usable over a wide range of frequencies, such as from under 5 MHz to over 100 MHz. In various embodiments, different nominal frequencies and/or different nominal amplitudes are used for different applications and/or usage scenarios. It is noted and understood that any specific values discussed herein (e.g., frequencies, amplitudes, etc.) are meant to be illustrative only. Other values, as will be appreciated by those skilled in the relevant arts, are also contemplated and encompassed within the scope of this disclosure.

Antenna

In some embodiments, the electric field is radiated through an antenna, such as a two-wire antenna, a monopole antenna, a dipole antenna, a differential antenna, an interdigitated antenna, any collection of one or more radiating elements, or any combination of the preceding. In various embodiments, any type of antenna that can radiate the electric field so as to couple electrical circuitry generating the electric field (e.g., an electric field generator) with a body (for which at least one parameter is to be computed) is usable. In further embodiments, the antenna is stationary relative to the body, such as by being attached to and/or as part of a bed (e.g., a bed frame, a mattress, etc.), a covering of the bed (e.g., a bed sheet, blanket, a pillow, a mattress topper, etc.), a chair, or any other item with which the body is in relatively close proximity (e.g., within the reactive near-field region of the electric field radiated by the antenna). In various examples, the antenna is positioned on the bed such that it is not in direct contact with a human body during operation of the BPCD. For example, the antenna is positioned underneath a bed covering. While example embodiments describe implementations with respect to a "bed," it is understood that this term is not intended to be limiting. Rather, a "bed" as that term is used herein includes any structure that is in relatively close proximity to a body and which is usable for sleeping, resting, observation, monitoring, etc. as described herein. Further, there is no implication in the use of the term "bed" that the body is lying down (e.g., prone or supine), and the techniques described herein are usable with the body in any position (e.g., sitting, standing, etc.).

In some embodiments, the antenna is a differential antenna (e.g., as compared to an antenna with one active lead and one ground lead, a differential antenna has in-phase and out-of-phase signals transmitted by separate antenna elements). For example, the antenna is connected to a differential electric field generator and/or to a differential detector. In various embodiments and/or usage scenarios, use of a differential antenna provides greater rejection of common mode noise. For example, when computing physiological parameters of a first human body, use of a differential antenna provides greater immunity to common-mode noise, and even a second human body further away from the antenna than the first human body affects signals from the antenna largely as common-mode noise.

In some embodiments, the antenna is considered to be a sensor, as it "senses" interactions of the body with the electric field. For example, additional embodiments described below with respect to a "sensor strap" are usable as an antenna. Such techniques are usable with and/or combinable with the techniques described herein. In various embodiments, a structure of the antenna is optimized for near-field coupling (vs. typical radio antennas, such as dipoles, which are optimized for far-field reception, or vs. coil antennas which are optimized for magnetic field coupling). In various embodiments, the antenna structure comprises a plurality of legs, with each leg having a plurality of traces. For example, a differential "2c3" antenna structure, as that term is used herein, has two parallel legs separated by a distance determined at least in part by the nominal frequency of the electric field generator and/or the desired penetration into the body. Each of the legs of the 2c3 antenna comprises multiple parallel traces (e.g., conductors), such as three traces for the 2c3 antenna, at a closer separation than the separation between the two legs. Wider separation between the legs provides a deeper penetration into a body adjacent to (e.g., lying on) the antenna, but with a lower average magnitude of the resulting electric field. Up to a point (e.g., until transmission power limits are reached), the lower average magnitude is able to be compensated by increasing a driving voltage of the electric field. In some embodiments and/or usage scenarios, the separation between the legs is between 1 and 20 inches, such as 3.5 inches or 12 inches, and the separation between the multiple parallel traces of each leg is between 0.1 and 0.5 inches, such as 0.25 inches.

In general, by varying one or more factors such as spacing of legs of an antenna, a number of parallel traces of each of the legs, a width and/or a length of each of the parallel traces, and/or a degree of interdigitation (if any), the antenna is optimizable for a depth of penetration into a body vs. a broader area of coverage with a shallower depth of penetration. In some embodiments, a length and/or a width of each of the legs and/or of each of the parallel traces of the legs differs. For example, adding additional parallel traces in a particular area increases coverage in that area.

In various embodiments, a length of the legs of a near-field-coupling optimized antenna is chosen to correspond to a width of a human body when lying supine. For example, a 19 inch length is sufficient for the supine width of approximately 95% of the human population. In general, shorter antenna lengths couple less to the human body (and thus have smaller coupling interactions), and longer antenna lengths potentially create additional dissipative loading (leading to increased dampening of the electric field) and/or have increased coupling with environmental factors not associated with the human body being observed. Other types of antennas, such as other configurations of interdigitated and/or differential antennas, are also contemplated.

Figure 17A:
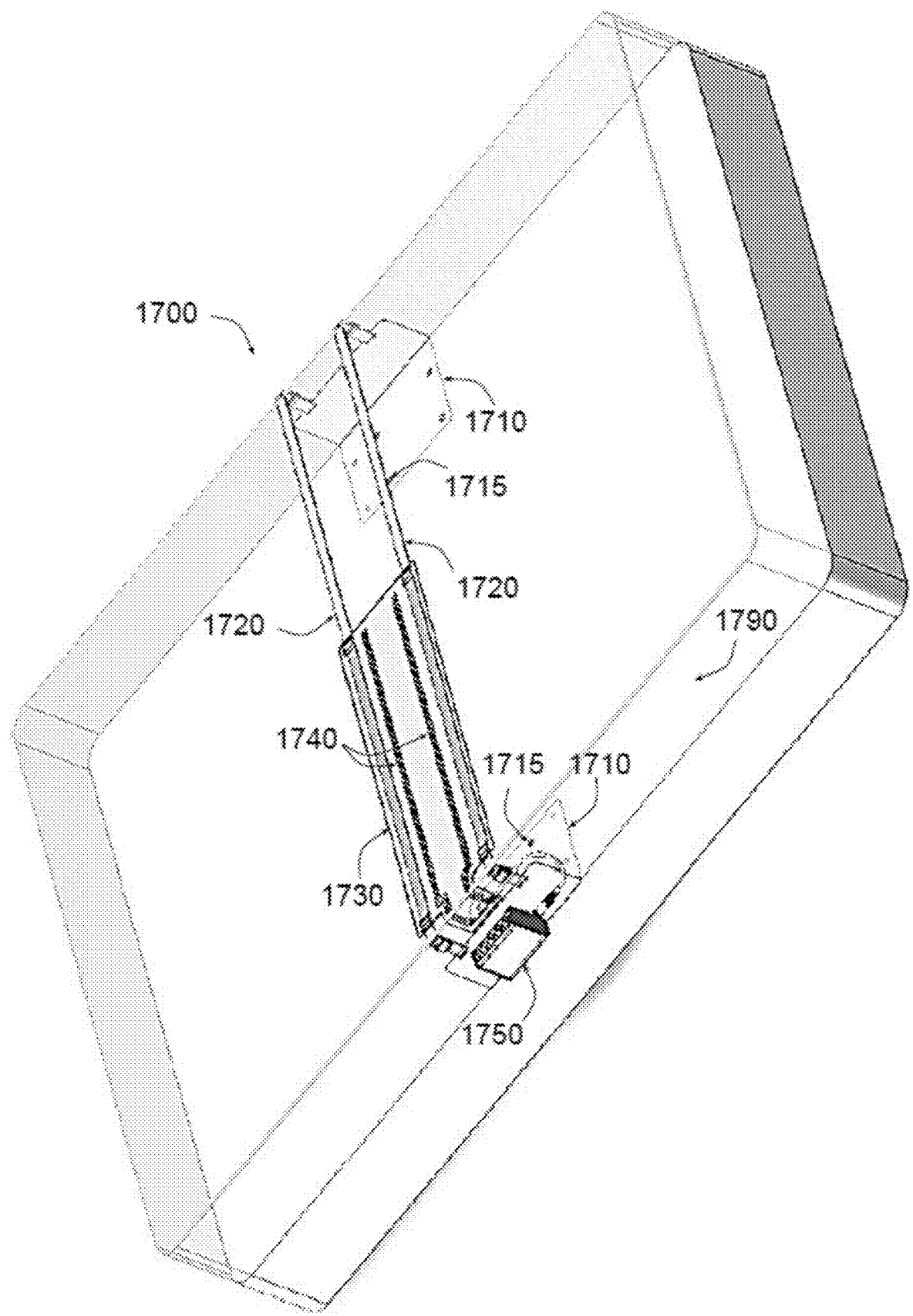
FIGS. 17A and 17B illustrate an example of a sensor strap system with a near-field-coupling-optimized antenna according to certain embodiments of the present disclosure.
Figure 17B:
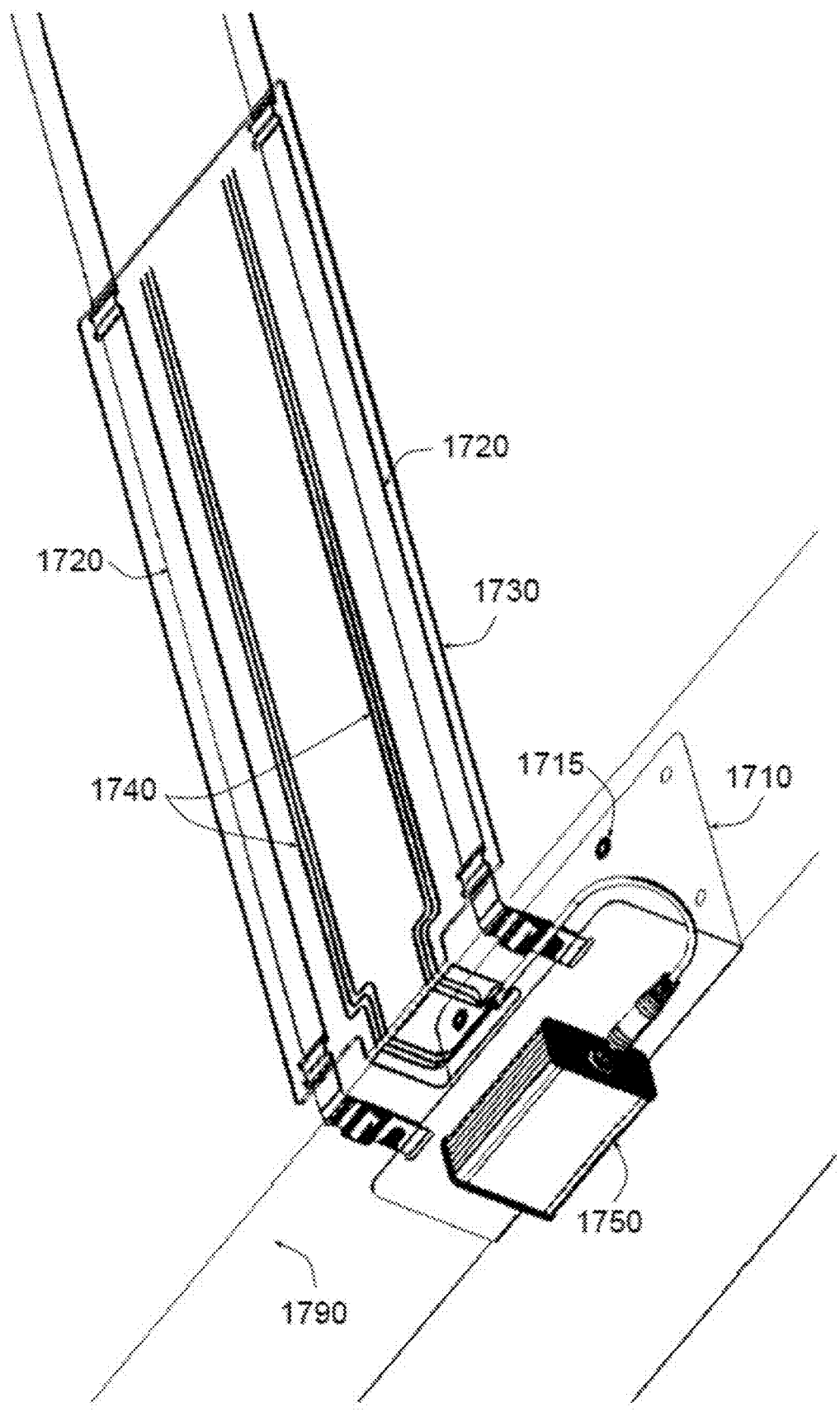

In some embodiments, a differential 2c3 or other antenna, such as a near-field-coupling-optimized antenna, is part of a sensor strap system attached to a bed 1700, as illustrated in FIGS. 17A (full view) and 17B (enlarged view). As illustrated in FIGS. 17A and 17B, two L-shaped brackets 1710 are placed under mattress 1790 of bed 1700 at a distance from a top of bed 1700 so as to position the sensor strap 1730 underneath a supine human body (not illustrated) in a position between the expected locations of the shoulders and hips of a torso of the body. Weight of mattress 1790 (and the human body), plus the wrap angle of the straps 1720 down the edge of mattress 1790, keep brackets 1710 from moving (e.g., pulling out from under the mattress) due to tension from straps 1720. Optionally, there are one or more anti-slip or slip resistant elements 1715 (e.g., high-friction rubber buttons or pads, adhesives, hook and loop fasteners, etc.) on one or more sides of a bottom leg of brackets 1710 to better grab an underside of mattress 1790 and/or the supporting structure of bed 1700 underneath the mattress. Control module 1750, connected to antenna 1740, contains for example, at least the analog electronics of a BPCD. Control module 1750 is connected to a source of power and/or to other portions of the BPCD via additional wiring (not illustrated).

In various embodiments, straps 1720 are nylon (or other polyamide or plastic) straps with buckles and/or clips (such as side-release buckles made by Fastex®) that enable adjustment of the strap tension, providing ease of adjustment at low cost. In various embodiments, a size of the sensor strap system is based on a size of the mattress on which it is to be used. In other embodiments, one set of adjustable straps covers all bed sizes, with any excess strap length tucked under the mattress on the far side from a control module 1750. In various embodiments, antenna 1740 is slidable across a width of mattress 1790 so as to be positioned at a center of the body's sleeping area (not necessarily adjacent to an edge of the mattress), and is held in place with, for example, three-leg strap buckles. In various embodiments, control module 1750 mounts directly to one of brackets 1710, and, in further embodiments, is rotatable 180 degrees for left-side or right-side mounting.

In some embodiments, sensor strap 1730 comprises antenna 1740 encased between sheets of a flexible material (e.g., plastic) and/or as part of a flexible circuit board. In further embodiments, the flexible material is a silicon-based elastomer such as polydimethylsiloxane (PDMS) and/or an FDA-approved material usable in hospital beds. According to various embodiments, antenna 1740 is one or more of: solid wire; stranded wire; copper, silver, gold, aluminum or other conductive metallic sheeting; copper, silver, gold, aluminum or other conductive metallic foil; any other suitable material for antenna construction; and any combination of the forgoing. In some embodiments and/or usage scenarios, antenna 1740 uses 24 AWG wire with 11/34 stranding.

In some embodiments, a connection between a portion of an antenna used for monitoring a body in an electric field radiated by the antenna and analog electronics that detect changes in the electric field is protected by guard traces, such as passive (e.g., grounded) or active (e.g., having signal content) guard traces. In various embodiments, an active guard trace uses a buffered and optionally and/or selectively (slightly) attenuated copy of a same signal being transmitted by the wire being protected. Whereas a ground shield introduces capacitance vs. the wire being protected, this type of active guard trace has minimal or no capacitive impact as there is no appreciable voltage differential (vs. the signal being guarded). In a first example, active wires in the antenna (e.g., two wires for a differential antenna) are protected within twinaxial cabling (having an outer ground). In a second example, active wires in a plated antenna are protected with shielding below and/or on the sides of traces comprising at least a portion of the antenna, and the shielding is active.

According to various embodiments, the antenna one or more of: has a preferred orientation that is, at least in part, along a major axis of the body; has a preferred orientation that is, at least in part, perpendicular to a major axis of the body; has a preferred orientation that is, at least in part, diagonal to a major axis of the body; has no preferred orientation with respect to the body; and/or encloses the body.

In some embodiments, two or more antennas are used. In further embodiments, each of the two or more antennas comprises one or more of the features and/or properties:
  connection to a respective electric field generator operating at a respective nominal frequency (e.g., a first antenna radiating at 25 MHz and a second antenna radiating at 27 MHz) and/or a respective nominal amplitude (e.g., a first antenna radiating at 2.5 Volts and a second antenna radiating at 3.0 Volts);
  connection to respective phase-shifting circuits having a common frequency source (e.g., a crystal oscillator);
  having a different physical dimension (e.g., a first antenna has an electrical length of 18 inches and a second antenna has an electrical length of 24 inches);
  having a different physical orientation (e.g., two antennas, one for the right side of a bed and one for the left side, or two antennas one oriented right-to-left on a bed and the other oriented top-to-bottom on the bed);
  having a different type (e.g., one monopole antenna and one dipole antenna);
  and any combination of the foregoing.

In various embodiments where two or more antennas are used, at least two of the two or more antennas are connected to a same electric field generator. In further embodiments, the at least two of the two or more antennas are connected to the same electric field generator via a switch and are used in a time-division-multiplexed (TDM) manner. In some other embodiments, multiple electrical field generators are present, with each one being connected to one or more antennas.

In some embodiments, in order to observe nighttime resting physiological parameters of a first human body on a bed with a second human body, an antenna is positioned in a portion of the bed where the first human body is present (e.g., sleeps). That is, if the first human body is present on the right side of the bed, the antenna is positioned so that it is on the right side of the bed and thus the first human body creates stronger coupling effects with the antenna than the second human body.

In some embodiments, in order to observe nighttime resting physiological parameters of a first human body on a bed with a second human body (or several other bodies), multiple antennas are used to differentiate two or more human bodies on the bed. In a first example, the electric field radiated from a first antenna on one side of the bed interacts more strongly with the first human body, and the electric field radiated from a second antenna on the other side of the bed interacts more strongly with the second human body. In various embodiments and/or usage scenarios, the electric field radiated by the first antenna and the electric field radiated by the second antenna are at different respective nominal frequencies and/or are radiated at different (e.g., non-overlapping) times. In further embodiments and/or usage scenarios, computation of one or more physiological parameters of the first human body are a function of the measurements of the frequency and/or the amplitude of the electric fields radiated by the first and the second antennas. For example, by computing one or more physiological parameters of the second human body using measures of the frequency and/or the amplitude of the electric field radiated by the second antenna, an effect of the second human body on the electric field radiated by the first antenna is determined and used to improve computation of one or more physiological parameters of the first human body using measurements of the frequency and/or the amplitude of the electric field radiated by the first antenna. For example, by determining the effects of the second body on the second electrical field, the accuracy of computing physiological parameters of the first human body is enhanced.

In various embodiments, two or more antennas are used to provide spatial and/or frequency diversity. Spatial diversity is provided, for example, by having each of the two or more antennas in a respective physical location and/or in a respective orientation and thus interacting more strongly with bodies at or near the respective physical location and/or better aligned with the respective orientation. The stronger interaction with a particular one of the antennas provides, for example, improved signal quality for measurement of a physiological parameter of one of the bodies. Frequency diversity is provided, for example, by having each of the two or more antennas radiate at a respective nominal frequency. In some of the various embodiments, measurements of the respective frequency and/or the respective amplitude radiated by each of the two or more antennas are used individually, such as for respective bodies interacting with electric fields radiated by each of the two or more antennas. In others of the various embodiments, measurements of the respective frequency and/or the respective amplitude radiated by each of the two or more antennas are combined, at least in part, to improve computation of one or more parameters of at least one body interacting with the electric field radiated by at least one of the two or more antennas. For example, computation of one or more parameters of a first body interacting with the electric field radiated by a first one of the two or more antennas is used to determine an effect of the first body on the electric field radiated by a second one of the two or more antennas and to improve computation of one or more parameters of a second body interacting with the electric field radiated by the second antenna. In some of the various embodiments, each of the two or more antennas is connected to a respective electric field generator. In others of the various embodiments, a single electric field generator is time-division multiplexed so that only one of the two or more antennas is used at a time.

In some embodiments, two or more antennas are used to provide separately optimized detection of respective periodic and/or non-periodic behaviors in the measured changes in the frequency and/or amplitude of the electric field. For example, a first antenna is optimized for greater depth of penetration into a human body (e.g., using wider spacing between legs of the antenna) and is better able to measure a respiration rate than a second antenna optimized for broader coverage at a shallower depth (e.g., using closer spacing between legs of the antenna and/or more elements in each of the legs of the antenna) used to measure heart rate (e.g., via blood flow and/or skin movement). In further embodiments, each of the two or more antennas is connected to a respective electric field generator operating at a respective nominal frequency and/or a respective nominal amplitude, where the respective nominal frequency and/or the respective nominal amplitude are selected to optimize for best detection of the respective periodic and/or non-periodic behavior.

According to various embodiments in which two or more antennas are used, the two or more antennas are one or more of: operated at a same nominal frequency and/or nominal amplitude; operated at different nominal frequencies and/or nominal amplitudes; operated at a same time; operated at different times, such as in a time-division multiplexed manner; operated synchronously (e.g., in a coordinated fashion); operated asynchronously (e.g., independently enabled and/or controlled); and any combination of the foregoing.

In some embodiments where two or more antennas are in use (e.g., at a same time), each of the two or more antennas radiates a respective electric field at a respective nominal frequency. In various embodiments, the respective nominal frequencies are selected such that one or more of: any beat frequencies have minimal or no impact on computations of one or more parameters of at least one body interacting with at least one of the respective electric fields; separation between a pair of the respective nominal frequencies is at least as large as expected changes in frequency due to interactions of one or more bodies with the respective electric fields; and any combination of the foregoing. In further embodiments, each of the two or more antennas is connected to a respective electric field generator (e.g., electric field generator 104 as illustrated in FIG. 1), and each of the respective electric field generators is connected to a respective detector (e.g., quadrature demodulator 108 as illustrated in FIG. 1).

In some embodiments, two or more antennas radiating respective electric fields at respective frequencies are used to compute respective physiological parameters of two or more organs of a human body. In other embodiments, one antenna is time-division multiplexed to radiate (in different time slots) two or more respective electric fields at respective frequencies to compute the respective physiological parameters of the two or more organs of the human body. In further of these embodiments, a first one of the respective frequencies is adjusted to improve a quality measure (e.g., a signal-to-noise ratio) for computation of the respective physiological parameters of a first one of the two or more organs, and a second one of the respective frequencies is adjusted to improve a quality measure for computation of the respective physiological parameters of a second one of the two or more organs.

Figure 6:
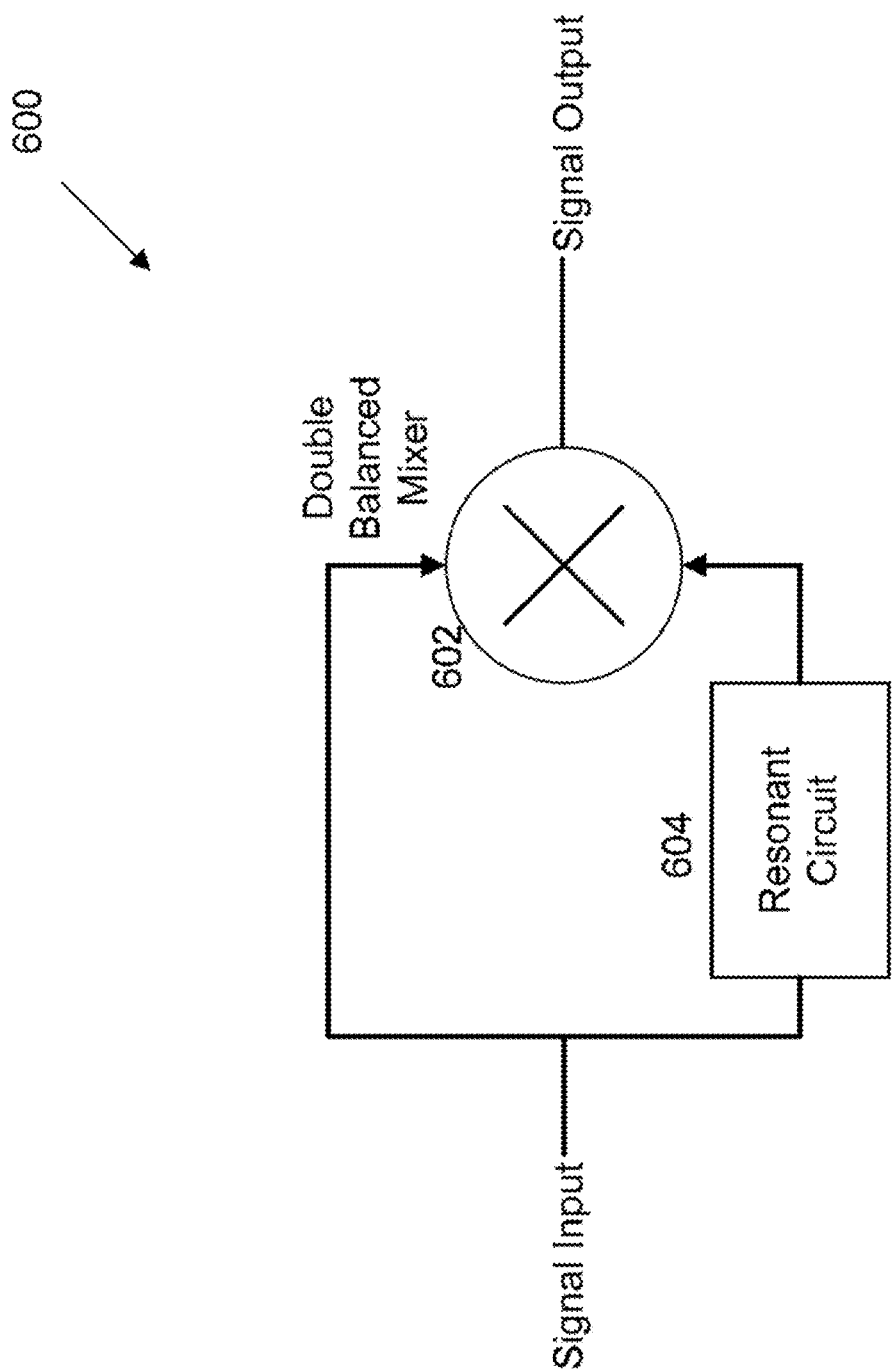
FIG. 6 illustrates an example of selected details of a quadrature demodulator according to certain embodiments.

In some embodiments where two or more antennas are in use (e.g., at a same time), each of the two or more antennas radiates a respective electric field at a same nominal frequency. In further embodiments, each of the two or more antennas is connected to a respective phase-shifting circuit (e.g., resonant circuit 604 as illustrated in FIG. 6). The respective phase-shifting circuit provides one input to a respective demodulator (e.g., mixer 602 as illustrated in FIG. 6), and there is a common oscillator providing a second input to all of the respective demodulators. Connecting each of the antennas to a separate isolated source (such as the output of the phase-shifting circuit) but operating all of the antennas at a same nominal frequency mitigates issues of interference and/or beat frequencies that are possible with antennas operating at different nominal frequencies.

While the examples described herein have generally used one or two antennas and/or one or two bodies, the techniques described herein are applicable to any number of antennas used to measure the parameters of any number of bodies.

Detector

In some embodiments, a detector measures the frequency and/or the amplitude of an electric field as it interacts with a body (e.g., a human body) in a reactive near-field region of the electric field. That is, the detector measures the frequency and/or the amplitude of the electric field as the electrical circuitry generating the electric field (e.g., an electric field generator) couples with the body. In some embodiments, the detector comprises a first detector to measure the frequency of the electric field and a second detector to measure the amplitude of the electric field. In other embodiments, a single detector is able to measure both the frequency and the amplitude of the electric field. In various embodiments, any number of detectors, each measuring the frequency and/or the amplitude of a respective electric field, are used.

While the description herein refers to "measurement of the frequency of the electric field" or "measurement of the amplitude of the electric field" using the singular noun "measurement" (or similar phrases with other forms of "measure"), this includes not just a single measurement, but a series of measurements computed over time. For example, to compute a physiological parameter of a human body such as a heart rate (in the range, for example, of between 20 and 200 beats per minute), the detector measurements of the frequency and/or of the amplitude are performed at a multiple (e.g., a fraction, one, or a number greater than one) of the rate of the parameter being measured, such as at least twice as fast, or up to hundreds or thousands of times as fast. Continuing the example, the detector measurement of the frequency of the electric field as used to compute a heart rate of a human body is performed, in some embodiments and/or usage scenarios, 1000 times per second, and in other embodiments and/or usage scenarios, 10000 times or more per second.

Figure 2:
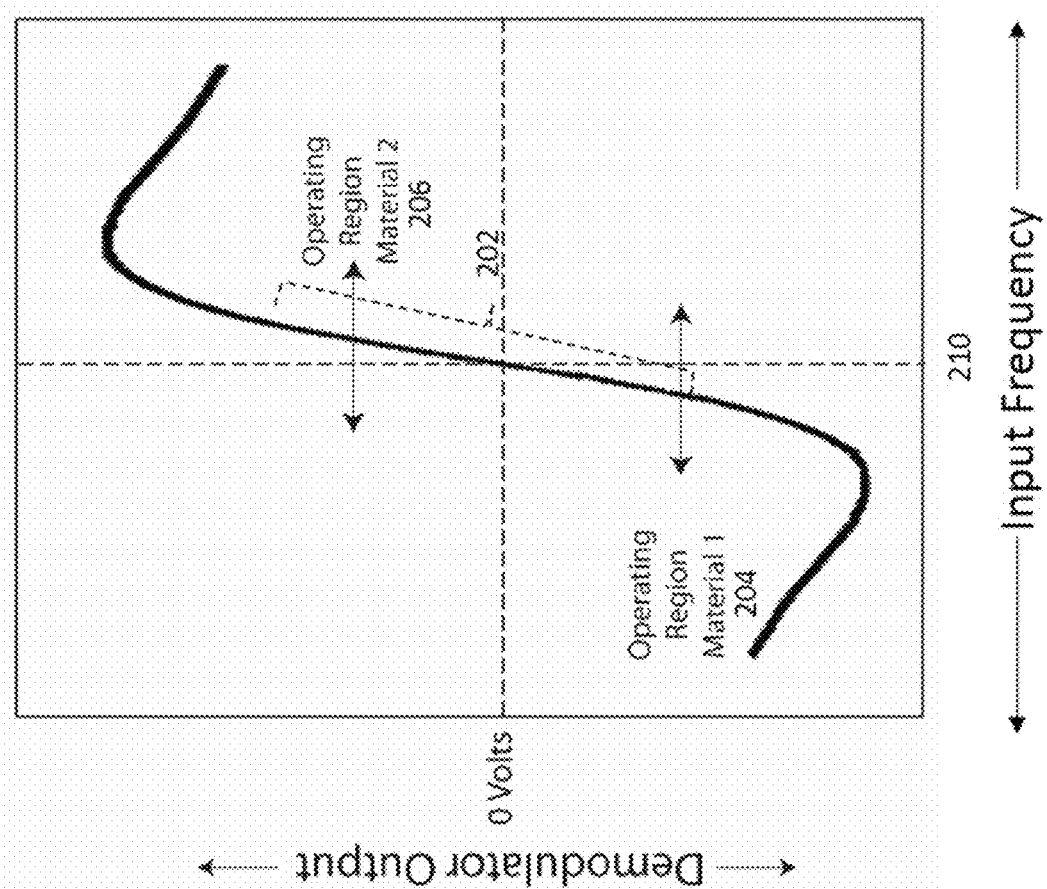
FIG. 2 illustrates an example of a transfer function of a quadrature demodulator according to certain embodiments.

A detector to measure the frequency of the electric field is any type of detector that measures any frequency associated with the electric field, such as a detector that directly measures a frequency of a signal, or a detector that measures the relative frequency of a signal as compared to a reference such as the nominal frequency (e.g., measuring changes in the frequency of the signal as compared to the nominal frequency). In a first example, such as illustrated in FIG. 1, the frequency changes due to coupling with the body are treated as a form of frequency modulation, and any suitable frequency demodulator (e.g., quadrature demodulator 108) or frequency detector (e.g., a phase-locked loop (PLL)) is usable to generate a waveform, such as a voltage waveform or a current waveform, corresponding to the frequency changes over time. For example, as illustrated in FIG. 2, frequencies less than the nominal frequency produce increasingly more negative voltages, and frequencies greater than the nominal frequency produce increasingly more positive voltages. In some embodiments, a voltage waveform thus generated is further processed by an analog-to-digital converter to produce a series of values corresponding to the waveform that are further processable, such as by a digital signal processor. In various embodiments, the analog-to-digital converter is a 12-bit, a 16-bit, a 20-bit, a 24-bit analog-to-digital converter, or any other suitable analog-to-digital converter. In a second example, such as illustrated in FIG. 4, a sample-and-hold device samples the electric field (as it interacts with the body in the electric field) at a specified sampling rate, and an analog-to-digital converter converts the output of the sample-and-hold device to a stream of digital information (corresponding to samples of the waveform of the electric field) that is further processable, such as by a digital signal processor. In a third example, a wideband analog-to-digital converter is able to measure the electric field directly at a high enough sampling rate to capture, with a sufficient quality measure (e.g., a signal-to-noise ratio), the changes in the frequency and/or the amplitude of the electric field due to interactions with the body in the electric field.

In some embodiments, for example as illustrated in FIG. 1 and FIG. 4, the detector is connected to the electric field generator and directly measures the frequency generated by the electric field generator as it changes due to interactions with one or more bodies in the electric field radiated by the antenna (e.g., external sensor device 102 or 402). There is no separate receiver (e.g., a separate antenna or a duplexer enabling a single antenna to both transmit and receive) to receive a signal (e.g., a reflected signal) from the generated electric field. In other words, the detector does not measure the frequency of the generated electric field by measuring a reflection or a reflected signal of the generated electric field, but instead measures the frequency of the generated electric field based on a connection to the electric field generator itself. In various embodiments, the electric field generator is connected between the antenna and the detector. In further embodiments, the detector is solely connected to any antenna indirectly via the electric field generator, and thus the detector is only able to measure the frequency of the generated electric field by measuring the frequency generated by the electric field generator. In various embodiments, the detector is configured to operate without a reference oscillator by comparing the frequency generated by the electric field generator with a phase-shifted version of itself. In further embodiments, the phase shift corresponds to a 90-degree phase shift at the nominal frequency. In some embodiments, the antenna is connected to the output of the electric field generator, while in other embodiments the antenna is connected to the phase-shifted version of the output of the electric field generator.

In various embodiments and/or usage scenarios, by measuring changes (e.g., as compared to the nominal frequency) in the frequency generated by the electric field generator due to interactions with the one or more bodies in the electric field, the detector detects changes in the coupling capacitance of the one or more bodies caused by movement of internal portions (e.g., organs) of the one or more bodies. Measurements of a BPCD using a differential quadrature demodulator have shown that capacitance changes as small as one femtofarad are detectable.

A detector to measure the amplitude of the electric field is any type of detector that either directly measures an amplitude of a signal, that measures the relative amplitude of a signal as compared to a reference (such as the nominal amplitude), and/or that indirectly measures the amplitude such as by measuring the gain applied by an automatic gain control circuit that maintains the measured amplitude of the electric field at or near (e.g., within a few percent of, or within a determined range of) a determined amplitude (e.g., at or near the nominal amplitude). In a first example, an analog-to-digital converter is usable to directly measure the amplitude of the electric field. In a second example, the electric field is first evaluated, such as with a sample-and-hold circuit or with a peak detector circuit, and the evaluated result is then processed by an analog-to-digital converter. The series of values produced by the analog-to-digital converter is then further processable, such as by a digital signal processor. In various embodiments, the analog-to-digital converter is an 8-bit, 12-bit, a 16-bit, a 20-bit, a 24-bit analog-to-digital converter, or any other suitable analog-to-digital converter. In a third example, such as illustrated in FIG. 1, a switch (such as amplitude comparison switch 110) selects (e.g., under control of a signal processor, such as signal processor 116) between either the output of the electric field generator (e.g., electric field generator 104) as it couples to one or more bodies in the electric field and an amplitude reference (e.g., the nominal amplitude and/or another amplitude reference source such as amplitude reference source 106). The output of the switch is an input to the signal processor where an analog-to-digital converter in the signal processor is able to convert the electric field and amplitude reference signals to values for comparison. In a variation of the third example, the switch is time-based in that the signal processor, by measuring the amplitude of the electric field at a particular time (e.g., upon installation of the BPCD and/or during a quiescent period when there are no observed variations in the measurements of the electric field such as when a body is not present in the electric field), the signal processor is configured to record the amplitude measurement at the particular time as the amplitude reference. Further in the variation of the third example, in some embodiments, the signal processor is configured to periodically update the recorded amplitude reference (such as during quiescent periods when there are no observed variations in the measurements of the electric field) so as to account for any environmental changes that might affect the amplitude reference. In various embodiments, when a body is present in the electric field, the measured amplitude will be less than the amplitude reference. In some embodiments, signal processor 116 processes a difference between the measured amplitude and the amplitude reference to determine various characteristics associated with the body, such as the presence or lack of presence of the body in the electric field, a weight of the body, a weight change of the body compared to a previous weight, etc.

In a combined approach, such as illustrated in FIG. 4, a detector to measure the frequency and/or the amplitude of the electric field comprises a sample-and-hold circuit operating at a sampling rate, followed by an analog-to-digital converter (such as a 16-bit or a 24-bit analog-to-digital converter). A series of values at the sampling rate is produced, such as 5000 values per second. (While the nominal frequency is much higher than the sampling rate, the sampling rate need only be sufficiently fast to accurately capture changes in the nominal frequency due to coupling with a body in the electric field one or more of whose parameters are being computed.) The series of values is processed by a digital signal processor which is programmed to compute the (relative) frequency (e.g., using frequency domain analysis) and/or the amplitude (e.g., using peak detection) of the electric field.

The techniques described herein and in the U.S. Ser. No. 10/080,507 patent (which is hereby incorporated by reference for all purposes) provides detectors to measure the frequency and/or the amplitude. Such techniques are usable with and/or combinable with the techniques described herein.

Computation Unit

In some embodiments, a computation unit (e.g., a processor, such as a digital signal processor) computes (e.g., using signal processing techniques) from the detector measurements of the frequency and/or the amplitude of the electric field one or more parameters of the body (such as physiological parameters of a human body). For example, in some embodiments, the computation unit uses the output of one or more analog-to-digital converters producing a series of values corresponding to the measured amplitude of the electric field and/or a series of values corresponding to the measured frequency of the electric field to compute the one or more parameters of the body.

In some embodiments, the computation unit searches for periodicities (periodic behavior) in the detector measurements of the frequency and/or the amplitude that correspond to movements of the body and/or of internal portions of the body (e.g., organs of a human body). For example (though it is not nearly this simple, as explained below), movement of the lungs of a human body is observed as a relatively large frequency change with a periodicity of between 5 and 100 times per minute, and movement of the heart is observed as a relatively smaller frequency change with a periodicity of between 20 and 200 times per minute. The term periodicities (periodic behavior) as used herein includes quasiperiodicities (quasiperiodic behavior), i.e., patterns of behavior that are completely deterministic as well as those that have some degree of unpredictability. Physiological parameters, such as respiration rate and/or heart rate, may exhibit periodic behavior, but more typically exhibit quasiperiodic behavior.

In some embodiments, determining the periodicities uses time domain techniques (e.g., autocorrelation and peak-picking), frequency domain techniques (e.g., Fast Fourier Transform (FFT) or other transforms, and cepstral methods), and/or other techniques for determining periodicities in data (e.g., cosinor analysis). In various embodiments, any technique to determine periodicities is applicable.

According to various embodiments, the computation unit computes a particular one of the one or more parameters of the body as one or more of: a rate corresponding to a frequency of the corresponding periodic behavior; any statistical function, such as a minimum, a maximum, an average, an average over a certain interval, and/or a standard deviation, of the rate; data indicating time intervals and/or durations during which the rate was computed; data indicating time intervals and/or durations during which the rate was not computed; a series of data indicative of the corresponding periodic behavior over time (e.g., that could be used to graph the corresponding periodic behavior and/or functions thereof); and any combination of the foregoing.

In some embodiments, the computation unit computes a particular one of the one or more parameters of the body as a time-average over a specified interval. That is, an average rate is determined by counting occurrences of a respective periodic behavior (corresponding to the particular parameter) during the specified interval. In further embodiments, the time-average is a rolling average. For example, in various embodiments and/or usage scenarios, a resting heart rate is computed using a five-minute rolling average. In further embodiments where more than one parameter of the body is being computed, each of the parameters of the body is computed as a time-average using a respective specified interval. In various embodiments and/or usage scenarios, such as for calibration and/or to generate data for an approval process, the respective specified interval is selected to match an averaging interval used by a reference (e.g., a reference device or a trained observer) so that computed statistics are more comparable to those produced by the reference.

In some embodiments, the computation unit computes a particular one of the one or more parameters of the body as a computation of a "mass" of the body (e.g., a relative measure of volume and/or weight, not necessarily a weight in, for example, pounds) and/or a change of mass of the body using, for example, the measured amplitude and/or changes in the measured amplitude of the electric field. In further embodiments, the computation of the mass comprises a computation of a body mass index (BMI) and/or a relative (e.g., a change) in BMI. In further embodiments, the computation of a change in mass (and/or BMI) is measured over a duration of two or more days using nighttime resting computations of the (relative) body mass and/or predetermined (e.g., set during initialization) calibration values.

In some embodiments where more than one parameter of the body is being computed, the computation unit computes each of the parameters of the body separately. In other embodiments, a first one of the parameters, such as a dominant one of the parameters, is computed first, and knowledge of the first parameter is used to compute one or more subsequent parameters, thereby enabling a more accurate computation of the one or more subsequent parameters.

In various embodiments, the computation unit is able to distinguish a type and/or a state of a body in the electrical field based on changes in the measured frequency and/or the measured amplitude. In a first example, a human or an animal body has a larger dissipative factor than a more structurally rigid and/or metallic object such as a suitcase. Both a suitcase and a human body may cause a similar overall change in the measured frequency, but the human body will cause a greater change in the measured amplitude due to the higher dissipative factor. Accordingly, a type of a body entering and/or present in the electric field is determinable. In a second example, lack of detection of periodic behavior in the measured frequency despite presence of a body with a relatively larger dissipative factor is indicative of an organic but non-living body, such as a cadaver. In a third example, cessation of detection of periodic behavior in the measured frequency while the body is still determined as being in the electric field is evidence of a severe medical problem (e.g., cardiac arrest).

In some embodiments, such as illustrated in FIG. 12, the computation unit stores and/or communicates (such as over a network) the computed one or more parameters of the body. For example, in various embodiments, the computation unit is connected to a network communication device (such as a wireless network access device or a cellular network access device) and communicates the computed one or more parameters of the body over a network to a server or any other device. The network communication device optionally and/or selectively communicates the one or more parameters of the body in any manner, such as by communicating a single measurement, communicating a collection of measurements, communicating a pre-processed (e.g., statistically reduced) version of one or more measurements, communicating any of the preceding periodically, communicating any of the preceding at any other interval (e.g., an interval that is not periodic), and/or communicating any of the preceding in response to a request (e.g., a request received from the network). The server or other device maintains, such as in a database, the computed one or more parameters of the body over an extended period of time (e.g., days, weeks, months, or years) to enable observation of trends in changes of the one or more parameters. Further, the server or other device maintains such data for a plurality of bodies, e.g., for a number of patients in a patient population being monitored.

In various embodiments, the computation unit comprises one or more processors (such as embedded processors, microprocessors, multi-core processors, signal processors, digital signal processors, graphics processors, field-programmable gate arrays, application-specific integrated circuits, etc.). In a first example, in some embodiments, there is a respective computation unit for each one of a plurality of detectors, while in other embodiments, a single computation unit serves the plurality of detectors. In a second example, the computation unit comprises two or more processors to divide work, such as a first one of the two or more processors to serve one or more detectors (e.g., to process measurements from an analog front-end), and a second one of the two or more processors to provide higher-level functions such as communication with a network. In a third example, a first portion of the computation unit comprising one or more processors is co-located with an analog front-end (to process measurements from the analog front-end such as to determine periodic and/or non-periodic behaviors in the measured frequency and/or amplitude) and communicates the measurements (or a pre-processed version thereof) over a network with a second portion of the computation unit comprising one or more processors that performs higher-level computations on the measurements (or the pre-processed version thereof), such as computations to determine a rate of movement of internal components, a physiological parameter, etc. Continuing the third example, in some embodiments the second portion of the computation unit is physically and/or logically close to the first portion of the computation unit (e.g., in a same building and/or on a same local-area network), while in other embodiments, the second portion of the computation unit is remote from the first portion of the computation unit (e.g. connected over the internet, such as when a cloud server comprises the second portion of the computation unit).

Tuner

In some embodiments, such as illustrated and described with respect to tuner 820 of FIG. 8 and/or tuning circuitry 1120 of FIG. 11, a tuner is used to adjust the nominal frequency of the electric field generator so that, for example, a center of the observed frequency measured by the detector stays at or near (e.g., within a few percent of) the nominal frequency. For example, a stationary human body lying on its back has a different effect on the electric field than a stationary human body lying on its side. In various embodiments, maintaining the center of the observed frequency measured by the detector at or near the nominal frequency enables circuitry measuring the frequency (and/or a change in the frequency) of the electric field to be operated in a region where its response is more predictable and/or more precise (e.g., more linear). Other techniques described herein describe some embodiments of such a tuner. Such techniques are usable with and/or combinable with the techniques described in this section.

In various embodiments, the tuner is configured to adjust the nominal frequency of the electric field generator so that a frequency-related output of the detector (e.g., the output of quadrature demodulator 108 as illustrated in FIG. 1) is maintained at a constant voltage (e.g., a constant peak voltage, a constant average voltage, or a voltage with a nominal value of zero).

In some embodiments, the center of the measured frequency of the electric field is determined dynamically. For example, instead of tuning the electric field to change the center of the observed frequency, voltage input to an analog-to-digital converter is level-shifted in a compensatory way, or the computation unit is able to adjust its interpretation of the detector measurement of the frequency (e.g., by dynamically determining a center point of frequency changes).

In some embodiments, a tuner is used to adjust the nominal frequency of the electric field generator so that, for example, a computation of a parameter of a body (e.g., a rate of movement of an organ of a human body) achieves a higher accuracy by improving the quality measure (e.g., the signal-to-noise ratio) of the periodic behavior in the measured frequency and/or measured amplitude. For example, depending on a particular characteristic of the body (e.g., the body mass index of a human body), or a particular (dynamic) position of the body (e.g., a human body that has rolled over from its back to its side), adjusting the nominal frequency of the electric field generator is able to produce measurements of the frequency and/or the amplitude of the electric field with a higher quality measure for the effects of the parameter of the body. In various embodiments, the quality measure for the effects of the parameter of the body is determined by a manner in which the parameter of the body causes a change in the frequency of the electric field. For example, in some embodiments, the quality measure is relative to an amount of the change in the frequency of the electric field due to the effects of the parameter of the body. Continuing the example, in further embodiments, tuning of the nominal frequency to achieve a greater degree of change in the measured frequency due to the effects of the parameter of the body improves the quality measure.

In various embodiments, the nominal frequency of the electric field generator is adjusted periodically to determine if a different (e.g., a higher and/or a lower) frequency produces a more reliable computation of the parameter of the body. For example, using "servo" techniques, the frequency is adjusted every one minute (or every five minutes, or any other suitable period) to "servo" in on a more optimal frequency. If the frequency is lowered (raised) and the quality measure (e.g., the signal-to-noise ratio) improves, the frequency is lowered (raised) further. Conversely if the frequency is lowered (raised) and the quality measure worsens, the frequency is raised (lowered). In further embodiments, an amount of the raising and/or lowering is proportional to the quality measure. For example, a higher quality measure would use smaller amounts of raising and/or lowering than a lower quality measure.

In some embodiments, one or more other signal quality measures are used instead of and/or in addition to the signal-to-noise ratio to control and/or to optimize the adjusting of the nominal frequency so as to improve the one or more other signal quality measures (and/or the signal-to-noise ratio). In a first example, internal autocorrelation ratios (e.g., from an autocorrelator determining periodic behavior in the measured frequency) are used to control and/or to optimize the adjusting of the nominal frequency. In a second example, internal data of any other technique used to determine periodic behavior and/or evaluate signal quality is usable in a similar fashion, for example frequency content, spectral purity, and/or change or lack of change in measured amplitude over a time interval.

In some embodiments, the computation unit uses the measurement of the frequency of the electric field to control the tuner (and adjust the frequency of the electric field). In various embodiments, analog circuitry is used to adjust the tuner. In other embodiments, other types of circuitry are used to adjust the tuner, such as digital circuitry, or circuitry with both analog and digital components.

In various embodiments, the nominal frequency of the electric field generator is adjustable over a range, such as from 20 MHz to 26 MHz. In further embodiments, the adjustment of the nominal frequency is controlled by the settings of one or more (for example, two, three or five)

digital control bits. In yet further embodiments, the computation unit is enabled to adjust the nominal frequency by setting the one or more digital control bits. In some embodiments, the digital control bits control a variable device (e.g., a variable resistor, a variable capacitor, or a variable inductor) that is part of the electric field generator.

In some embodiments, a time constant of adjustments to the nominal frequency of the electric field generator is selected to be long compared to changes in the frequency of the electric field due to the effects of the parameter of the body. For example, when measuring changes in physiological parameters of the human body, the time constant of adjustments is tens of seconds (e.g., 25 seconds). In further embodiments, the time constant is determined, at least in part, by a time period over which the physiological parameters are averaged.

In various embodiments a time constant of adjustments to the nominal frequency of the electric field generator varies dynamically. For example, during an acquisition phase (such as when initially powered on), the nominal frequency is configured to be changed rapidly, as compared to a tracking phase where the nominal frequency is configured to be changed more slowly while the physiological parameters are being computed.

Automatic Gain Control

In some embodiments, a measured amplitude of the electric field corresponds to proximity (e.g., a distance) of a body interacting with the electric field to the antenna radiating the electric field. The dissipative component of the interaction increases with decreasing distance. If the body is too close, the electric field is potentially dampened to the point where oscillation stops. If the body is too far, the interactions are weaker (e.g., independent of frequency, the quality measure is decreased due to distance). In some embodiments, the amplitude of the electric field is adjusted in response to a quality measure (e.g., a signal to noise ratio) being above a determined or specified upper value, such as where the signal to noise ratio is sufficiently high and reducing the nominal amplitude would not result in an insufficient quality measure. In various embodiments, the amplitude of the electric field is adjusted in response to the quality measure of a determined periodic behavior being below a determined or specified limit, resulting in an insufficient quality measure. For example, an automatic gain control (AGC) circuit is used to adjust (e.g., continuously) the amplitude of the electric field, such as to maintain the measured amplitude of the electric field at or near (e.g., within a few percent of, or within a determined range of) a determined amplitude (e.g., at or near the nominal amplitude). In various embodiments, adjusting the amplitude of the electric field compensates for changes in dissipative loading effects of the body, such as from body movement and/or body orientation change with respect to an antenna radiating the electric field. In further embodiments, the AGC circuit is part of a tuner that optionally and/or selectively is also able to adjust the frequency of the electric field. In a first example, if the measured amplitude of the electric field is decreased too much (indicating the body is too close) such that the measured amplitude of the electric field is below a determined lower threshold, the AGC increases the nominal amplitude. In a second example if the measured amplitude of the electric field shows too small a decrease (indicating the body is too far, is moving away from the antenna radiating the electric field, is in the process of leaving the reactive near-field region of the electric field, or has left the reactive near-field region of the electric field) such that the measured amplitude of the electric field is above a determined upper threshold, the nominal amplitude is reset to a default value (used when there is no body within sufficient proximity to the antenna of the BPCD).

In some embodiments, an amplitude adjustment is performed to improve a subsequent measurement of the frequency of the electric field. For example, an electric field is generated at a nominal amplitude using an electric field generator. The electric field is radiated through an antenna, and an amplitude of the electric field is measured as it interacts with a body in the near-field region of the electric field, in accordance with techniques disclosed herein. The nominal amplitude is adjusted according to the measured amplitude (e.g., by increasing or decreasing the amplitude to as described herein), and a modified electric field is subsequently generated using the electric field generator at a nominal frequency and the adjusted nominal amplitude. The modified electric field generated at the adjusted nominal amplitude is radiated through the antenna, and measurements are performed in accordance with the disclosed techniques (e.g., to determine one or more periodic behaviors in the measured frequency and/or to compute a respective rate of movement of an internal component of a body).

In some embodiments, measurement of the amplitude of the electric field is used, at least in part, to determine and/or adjust the nominal frequency of the electric field. In various embodiments, such adjustments of the nominal frequency are used to improve a subsequent determination of a periodic behavior based on the adjusted nominal frequency and corresponding to a movement of a component of the body following the adjustment. For example, in usage scenarios where different components of the body affect the interaction of the body with the electric field differently according to distance of the body from the antenna, changing the nominal frequency in response to the distance from the antenna (as determined by measurement of the amplitude of the electric field) improves the quality measure for a parameter of the body that is being computed.

In some embodiments, the computation unit uses the measurement of the amplitude of the electric field to control the electric field generator (and adjust the amplitude of the electric field). In various embodiments, analog circuitry is used to adjust the amplitude of the electric field. In other embodiments, other types of circuitry are used to adjust the amplitude of the electric field, such as digital circuitry, or circuitry with both analog and digital components.

In some embodiments, the nominal amplitude of the electric field is 1.0 Volts RMS, and the AGC circuit is configured to adjust the measured amplitude of the electric field from 0.5 Volts to 2.75 Volts RMS. In various embodiments, the AGC circuit is configured to adjust the nominal amplitude in response to the measured amplitude being outside of a determined range, such that the measured amplitude is maintained within a specified range (e.g., within 0.75 to 1.5 Volts RMS). In further embodiments, the AGC circuit is configured to not increase the amplitude of the electric field beyond a determined value, even if the measured amplitude is not within the specified range, if the power emitted by the electric field (e.g., a total radiated power level) exceeds a specified power limit (e.g., a determined power level).

According to various embodiments, "load detection" (i.e., determining an absolute and/or relative amount of dissipative matter, such as a body, subject to the electric field) uses one or more of: a measurement of the amplitude of the electric field; a comparison of a measurement of the amplitude of the electric field vs. the nominal amplitude of the electric field; a measurement of an AGC control signal used to regulate the nominal amplitude of the electric field; and any combination of the foregoing. In various embodiments, load detection is able to distinguish between a human body and an object such as a suitcase. In further embodiments, lack of variation in load detection for an extended period of time is indicative of a comatose or deceased human body.

In some embodiments, a time constant of adjustments to the amplitude of the electric field is selected to be longer compared to changes in the measured amplitude of the electric field due to the effects of the body interacting with the electric field (e.g., the time constant is longer than an expected duration of one or more non-periodic behaviors in the measured amplitude corresponding to movement of the body, such as rolling over in bed). For example, when measuring changes in physiological parameters of the human body, the time constant of adjustments is tens of seconds (e.g., 25 seconds). In another example, the time constant is at least ten times longer than an expected duration of non-periodic behaviors in the measured amplitude corresponding to movement of the body. In further embodiments, the time constant is determined, at least in part, by a time period over which the physiological parameters are averaged.

Differential Circuitry

In some embodiments, at least a portion of the circuitry in a BPCD (e.g., the electric field generator, the antenna, and/or the detector) comprises differential circuitry. Using differential circuitry in the electric field generator, the antenna, and/or the detector for the frequency measurement advantageously improves the quality measure (e.g., the signal-to-noise ratio) of the effects of the parameters of the body on the frequency of the electric field. That is, in some implementations, a BPCD with differential circuitry achieves significant rejection of common mode electrical fields in the environment (e.g., 60 Hz power noise and/or loading interference from other bodies passing by the BPCD), and is thus more sensitive to small changes in the electric field due to the effects of a body in the electric field, such as due to movement of internal organs of a human body interacting with the electric field. In a first example, a two-wire antenna is driven by a differential oscillator (as part of or all of a differential electric field generator), and a detector measuring the frequency of the electric field uses a differential frequency demodulator to obtain a higher quality measure for the effects of the parameters of the body on the frequency of the electric field. In a second example, the detector measuring the frequency of the electric field uses a differential sample-and-hold circuit followed by an analog-to-digital converter with a differential input. Laboratory results demonstrate that a particular differential circuit implementation achieved a 50 dB higher signal-to-noise ratio than a similar single-ended implementation.

FIG. 11 illustrates an example of selected details of an embodiment of a portion of a system for detecting and analyzing changes in a body according to certain embodiments. FIG. 11 illustrates a differential analog front-end that is usable as part of a BPCD, and includes a differential antenna 1102, a differential electric field generator 1104 (e.g., a differential oscillator such as a differential tank oscillator, a voltage-controlled differential oscillator, or a differential resonator), a differential detector 1108 (e.g., a differential quadrature demodulator and a differential low-pass filter, or a wideband analog-to-digital converter with differential input), and optional tuning circuitry 1120 (e.g., analog tuning circuitry receiving feedback from differential detector 1108 and/or digital tuning circuitry, such as a digital-to-analog converter receiving an input 1130 from a signal processor).

In some embodiments, the differential oscillator oscillates at a nominal frequency. Differential electric field generator 1104 generates an electric field at the nominal frequency which is radiated via differential antenna 1102. In some embodiments, the nominally frequency is statically and/or dynamically adjustable, such as by optional tuning circuitry 1120. In various embodiments, differential detector 1108 measures a frequency of the electric field as it interacts with a body in a reactive-near-field region of the electric field.

Optional tuning circuitry 1120 outputs a tuning signal used to control the nominal frequency and/or the nominal amplitude generated by the differential electric field generator. For example, the optional tuning circuitry outputs a voltage level used to control a voltage-controlled differential oscillator. In some embodiments, the optional tuning circuitry is an analog auto-tuning circuit. In other embodiments, the optional tuning circuitry is a digital-to-analog converter (DAC), and a signal processor provides a digital input to the DAC to tune the nominal frequency generated by the differential electric field generator. That is, software executing on the signal processor determines whether, when, and how much to adjust the nominal frequency and/or the nominal amplitude.

In some embodiments, the output 1140 from the differential analog front-end is a waveform representing changes in the frequency of the electric field, and is processed with a differential analog-to-digital converter and then with a digital signal processor. In various embodiments, the output of differential detector 1108 is single-ended and the analog-to-digital converter has a single-ended (instead of a differential) input. In other embodiments where differential detector 1108 is a wideband analog-to-digital converter, the output from the differential analog front-end is a sequence of values representing the waveform of the electric field.

Blanking

In some embodiments and/or usage scenarios, the computation of a parameter of a body by the computation unit uses techniques to identify a portion of the measurements of the frequency and/or the amplitude of the electric field (generated by an electric field generator) that has an inadequate quality measure (such as an inadequate signal-to-noise ratio) and/or corresponds to one or more non-periodic behaviors, and then prevent that portion of the measurements from being used in the computation of the parameter of the body (i.e., to "blank" out that portion of the measurements obtained during a measuring period comprising a succession of time points). For example, when determining one or more periodic behaviors, the computation unit determines the one or more periodic behaviors based on one or more time points from multiple time points during a measuring period that do not include one or more other time points corresponding to one or more non-periodic behaviors. In various embodiments, one or more quality measures (such as internal autocorrelation ratios or other internal data of techniques for determining periodic behavior, frequency content, spectral purity, change and/or lack of change in measured amplitude over a time interval, etc.) are used instead of and/or in addition to the signal-to-noise ratio. For example, in a case where the body is a human body, a portion of the measurements of the frequency and/or the amplitude of the electric field that does not correspond to an expected nighttime resting behavior of the human body (e.g., a relatively stationary body) is not used in computing rates of movement corresponding to periodic behaviors such as nighttime resting rates of movement of internal organs of the human body. In one example, when computing a nighttime resting heart rate, the computation unit identifies one or more portions of the measured frequency that are not indicative of a movement of one or more organs (e.g., the heart) and/or exhibit a frequency change greater than a threshold. In various examples, when such portions are identified, the computation unit does not use the identified portions of the measured frequency in computing the nighttime resting heart rate.

In various embodiments, the portion of the measurements of the frequency and/or the amplitude of the electric field that have an inadequate quality measure is used for other purposes, such as to tune the nominal frequency of the electric field generator, to adjust the nominal amplitude of the electric field generator, and/or to identify a period of excessive nighttime movement (such as for analysis of sleep stages). In various embodiments, the body leaving the reactive near-field region of the electric field is determined, such as by the quality measure dropping suddenly and/or by the amplitude increasing suddenly (or otherwise increasing beyond a determined threshold), and the portion of the measurements of the frequency and/or the amplitude of the electric field that correspond to a lack of (significant) presence of the body is blanked. In one example, such body presence detection is used to determine when a patient has left a bed.

In a first example, if the measurement of the amplitude of the electric field is below a lower threshold (the measured amplitude is too small indicating too much coupling to and suppression of the oscillations of the electric field generator) and/or if the measurement of the amplitude of the electric field is above an upper threshold (the measured amplitude is too large indicating insufficient coupling of the body to the electric field generator), the corresponding measurements of the frequency and/or of the amplitude are blanked. In a second example, if the measurement of the frequency of the electric field does not exhibit an expected magnitude of change (e.g., an expected magnitude of change representative of movement of the lungs), and/or if the measurement of the frequency of the electric field exhibits too great a magnitude of change (possibly indicative of movement of the body as a whole vs. movement of an organ of the body), the corresponding measurements of the frequency and/or of the amplitude are blanked. In a third example, if an expected periodic behavior indicative of the effect of an organ of the body on the electric field is not found, the corresponding measurements of the frequency and/or of the amplitude are blanked. Continuing the third example, if the expected periodic behavior is not found, one or more remedial measures are optionally and/or selectively taken, such as adjusting the frequency and/or the amplitude of the generated electric field to improve a quality measure, running diagnostics, and/or logging an event corresponding to a period of missing data. In a fourth example, a second body (e.g., a suitcase or a knapsack) or a pet (e.g., a Chihuahua or a Dobermann) lands on a bed where the interactions of a sleeping human body with an electric field are being measured. The addition of the second body affects the frequency and/or the amplitude of the electric field. At least a portion of the measurements where the second body sufficiently adversely affects the quality measure of the measurements of the frequency and/or the amplitude are blanked. After the initial change in the frequency and/or the amplitude of the electric field due to the addition of the second body, if the measurements of the frequency and/or the amplitude again have a sufficient quality measure, the blanking ceases, even though the second body may still be affecting the electric field. E.g., a pet joining its owner in bed is nominally only a transient disturbance, even if the pet remains on the bed.

Dual Sleeper

One use case of note is computing one or more physiological parameters of a patient on a bed with a partner (e.g., a spouse). In some usage scenarios, one or more respective physiological parameters of each of the patient and the partner are computed (i.e., the partner is also a patient). In various embodiments, the techniques described herein, such as using two or more antennas with spatial and/or frequency diversity, are advantageously used to handle such "dual sleeper" cases.

Server

FIG. 12 illustrates an example of a system comprising a Body Parameter Computing Device (BPCD) in accordance with various embodiments disclosed herein and a server. FIG. 12 illustrates a human body 1210 and a BPCD 1250. The BPCD comprises an electric field generator and antenna 1251 to radiate an electric field that interacts (1220) with the human body 1210. The BPCD further comprises a detector 1253 to measure the electric field as it varies in response to coupling between the human body 1210 and the electric field generator and antenna 1251. The BPCD further comprises a processor 1255 (e.g., a signal processor) connected to the detector 1253 and also to a Network Interface Card (NIC) 1257. Processor 1255 computes, using measurements from detector 1253, one or more physiological parameters of the human body 1210. Processor 1255 comprises memory 1260 (which includes computer-readable storage media), such as a volatile (e.g., Random Access Memory and/or Dynamic Random Access Memory) memory and/or a non-volatile (e.g., flash storage and/or disk storage) memory to store programs and/or instructions executed by processor 1255, results of computations of processor 1255, communications between processor 1255 and server 1280, and/or any other short-term or long-term data used by and/or produced by processor 1255 and/or other components of BPCD 1250. Although memory 1260 is illustrated as a part of processor 1255, memory 1260 is separate from, and connected to, processor 1255 in various embodiments. NIC 1257 enables processor 1255 to communicate with server 1280. Server 1280 comprises a processor 1285 (receiving data from NIC 1257, such as via a network interface not illustrated in FIG. 12) connected to a database 1287. According to various embodiments, NIC 1257 provides network connectivity (such as to server 1280) via one or more of: Ethernet; 802.11 (WiFi); cellular (e.g., 4G, LTE, or 5G); and/or any other type of wired or wireless network connection.

In various embodiments, processor 1255 is configured to communicate the one or more physiological parameters of the human body 1210 to server 1280 to be stored in database 1287. In further embodiments, the communication of the one or more physiological parameters comprises values of the one or more physiological parameters as well as information indicating times and/or time periods associated with the one or more physiological parameters. For example, one of the one or more physiological parameters is a nighttime resting heart rate, and processor 1255 communicates the nighttime resting heart rate to server 1280 at least once per day so that server 1280 is able to save historic data regarding the nighttime resting heart rate in database 1287.

Storing the one or more physiological parameters in database 1287 enables server 1280 (or other processors and/or servers in communication with server 1280) to perform analysis, such as trend analysis, on historic data stored in database 1287. In various embodiments, the analysis is used in the detection and/or prediction of the onset and/or the occurrence of conditions (such as a COPD exacerbation), symptoms (such as edema), and/or diseases (such as CHF, based on detecting symptoms such as edema and/or shortness of breath). In some embodiments, server 1280 is local to (e.g., within a same premises as) BPCD 1250. In other embodiments, server 1280 is remote from BPCD 1250 (e.g., is accessed via a network such as the Internet).

Device Hub

FIG. 16 illustrates an example of a system comprising a Body Parameter Computing Device (BPCD) acting as a hub for one or more other devices, such as other body-monitoring devices. FIG. 16 illustrates a human body 1610 and a BPCD 1650. The BPCD comprises an electric field generator and antenna 1651 to radiate an electric field that interacts (1620) with the human body 1610. The BPCD further comprises a detector 1653 to measure the electric field as it varies in response to coupling between the human body 1610 and the electric field generator and antenna 1651. The BPCD further comprises a processor 1655 (e.g., a signal processor) connected to the detector 1653 and also to a Network Interface Card (NIC) 1657 and to external connections 1659. Processor 1655 computes, using measurements from detector 1653, one or more physiological parameters of the human body 1610. Processor 1655 comprises memory 1660, such as a volatile (e.g., Random Access Memory and/or Dynamic Random Access Memory) memory and/or a non-volatile (e.g., flash storage and/or disk storage) memory to store programs executed by processor 1655, results of computations of processor 1655, communications between processor 1655 and cloud 1680 (representing an external network providing connectivity to external computers and/or devices, such as to server 1280 as illustrated in FIG. 12), communications (such as via processor 1655) between devices 1671, 1672, . . . , 1679 and cloud 1680, and/or any other short-term or long-term data used by and/or produced by processor 1655 and/or other components of BPCD 1650. Cloud 1680 represents connectivity to external computers and/or devices, such as any computer and/or device accessible via a network. According to various embodiments, the external computers and/or devices accessible via cloud 1680 are one or more of: local to (e.g., within a same premises as) BPCD 1650; remote from BPCD 1650 (e.g., accessed via a network such as the Internet); and any combination of the foregoing.

In some embodiments, BPCD 1650 is configured to connect to one or more external devices via external connections 1659. External connections 1659 represent one or more wired and/or wireless connections providing connectivity to one or more external (to BPCD 1650) devices 1671, 1672, . . . , 1679. According to various embodiments, the wired and/or wireless connections are of one or more types, such as RS-232, RS-422, IEEE 1394 (FireWire), Universal Serial Bus (USB), Ethernet, ZigBee, 802.11 (WiFi), cellular (e.g., 4G, LTE, or 5G) and any other type of wired and/or wireless connection. In further embodiments, NIC 1657 is one of external connections 1659 and connectivity of BPCD 1650 to cloud 1680 is optionally and/or selectively shared with connectivity to one or more of devices 1671, 1672, . . . , 1679. Devices 1671, 1672, . . . , 1679 are not necessarily co-located (e.g., within a same premises) as BPCD 1650. For example, in some usage scenarios, one of devices 1671, 1672, . . . , 1679 is a wearable device in communication with BPCD 1650 (via external connections 1659) over a network such as the Internet.

According to various embodiments, devices 1671, 1672, . . . , 1679 comprise one or more of: a weight scale (such as for patient weight measurement); a blood pressure monitoring device (such as a blood pressure cuff); a nebulizer with respiratory analysis capability; a pulse oximeter; a wearable monitoring device, such as a smartwatch; any other medical and/or diagnostic device; and/or any other device having and/or requiring cloud connectivity.

In some embodiments, by connecting devices 1671, 1672, . . . , 1679 to BPCD 1650, the one or more devices are enabled to have cloud connectivity via BPCD 1650. In further embodiments, the one or more devices are enabled to have cloud connectivity to a same server (e.g., server 1280 as illustrated in FIG. 12) to which BPCD 1650 is connected, thus providing a common repository for data collected from BPCD 1650 and the one or more devices. In further embodiments, the one or more devices are enabled to be monitored and/or controlled by the server.

In various embodiments, by connecting devices 1671, 1672, . . . , 1679 to BPCD 1650, BPCD 1650 is able to use (e.g., to analyze) data provided by devices 1671, 1672, . . . , 1679 as part of and/or in addition to the computing of the one or more physiological parameters of the human body 1610. In further embodiments, the one or more devices are enabled to be monitored and/or controlled by BPCD 1650.

While FIG. 16 illustrates BPCD 1650 acting as a hub for one or more other devices, other embodiments are contemplated where another device, such as one of devices 1671, 1672, . . . , 1679, is a device hub for BPCD 1650. In such embodiments, BPCD 1650 uses NIC 1657 to communicate to a server via the device acting as the device hub for BPCD 1650. In other embodiments, one of devices 1671, 1672, . . . , 1679, is a device hub for one or more other devices 1671, 1672, . . . , 1679. In such embodiments, the one or more other devices 1671, 1672, . . . , 1679 use any suitable network connectivity interface to communicate to a server via the device acting as the device hub for the one or more other devices 1671, 1672, . . . , 1679.

Computation of Physiological Parameters of a Human Body

Using as an example computing physiological parameters of the human body, the signal processing performed by the computation unit is complex because the detector measurement of the frequency of the electric field is a complex superposition of the response of multiple organs, other tissues, and liquids. To determine respiration rate and/or heart rate, the observed frequency changes are the result of the movement of not just the organs (the lungs and/or the heart) themselves, but of the rest of the body in response to the movement of those organs, as well as any background "noise" (e.g., due to borborygmus).

With the respiration rate as a first example, two of the major contributors to the observed frequency changes due to respiration are movement of the lung tissue itself (expanding when inhaling, contracting when exhaling) and movement of the chest (also expanding and contracting, roughly in phase with the lung tissue. There are other factors, too, such as movement of the diaphragm (powering the lung movement), and movement of other organs in the body in response to the chest cavity movement. How much each of these contributes to the "signal" (the change in observed frequency) produced by respiration is a combination of multiple factors:

The nominal frequency of the electric field and how deeply the signal is able to penetrate into the body. Very high (GHz) frequencies generally only penetrate "skin deep", while lower frequencies (20 MHz) may penetrate multiple centimeters.

The permittivity and/or dissipation factor of each of the organs, other tissues, and liquids affected by respiration. Each of the organs, other tissues, and liquids has a different permittivity, and these permittivities are frequency-dependent to different degrees. Further, some effects due to a single organ may increase permittivity, and other effects due to the same organ may decrease permittivity.

The relative time(s) at which the effects occur.

The type, design and location of one or more antennas used to radiate the electric field.

In the case of the respiration rate, expansion of the lungs when inhaling decreases permittivity of the lungs themselves, but the expansion of the chest cavity and the skin has an opposite effect and increases effective permittivity (e.g., due to increasing contact with and/or closeness to the antenna). (For example, due to inhaling, a larger portion of the body becomes closer to the antenna.) Since some of the multiple effects change permittivity in opposing directions, the observed changes in the measured frequency of the electric field due to movement of the lungs may vary widely depending on body position or other factors. For example, effects of the chest cavity movement may dominate when the human body is prone or supine in relation to the antenna vs. when the human body is on its side.

Because the responses of the various organs, other tissues, and liquids change with frequency, in some embodiments, the nominal frequency of the electric field generator is changed dynamically to find a frequency at which the observed signal (i.e., the observed changes in the detector measurement of the frequency of the electric field) from one or more organs is most readily captured (i.e., a frequency having a better signal-to-noise ratio).

As a second example, computation of the heart rate is affected by the same factors as the computation of the respiration rate, and is further complicated by being a comparatively much weaker signal. That is, when observing the "whole body" (or a substantial portion of the body, such as the torso) interacting with the electric field, the observed signal from the lungs is more than an order of magnitude larger than the observed signal from the heart. The observed signal from the heart is created from multiple sources, including: the heart muscle itself, the pulse wave in the blood vessels from a heartbeat, the expansion (and subsequent contraction) of the arteries due to the heartbeat, movement of the chest cavity and skin due to the heartbeat, etc. Further, many of these sources are phase shifted by a significant amount, e.g., due to the rate at which the pulse wave propagates through the arteries.

In a variation of these examples, some of the factors affecting computation of the respiration rate and/or of the heart rate are mitigated by positioning the antenna adjacent to a different part of the human body and/or by using two differently-positioned antennas and switching between them based on a determined position of the human body (e.g., by selecting one of the antennas with a higher quality measure). An antenna positioned for a human body lying down on a bed may be less effective when the human body is sitting up in the bed as compared to an antenna optimized for a sitting position, such as by being positioned to measure the effects of the femoral artery on the electric field. In some embodiments and/or usage scenarios, such as measuring driver alertness, an antenna in a seat-back would be responsive to upper-body movement (e.g., steering), potentially creating excessive periods of blanking, whereas an antenna in a seat-bottom and optimized for a sitting position experiences less of the effects of the upper-body movement. In various embodiments and/or usage scenarios, two or more antennas are used in particular environments, such as hospital beds, where a position of the human body may be changed. For example, a hospital bed has a first antenna optimized for situations where the human body is lying down in the hospital bed, and a second antenna optimized for situations where the human body is sitting up in the hospital bed (such as when a head of the hospital bed is raised). Continuing the example, an antenna positioned to be near the buttocks of a human body in a sitting position is able to be sensitive to both heart rate and respiration rate via blood flow near the skin for heart rate, and via expansion and/or movement of the buttocks in response to respiration.

The computation unit is able to determine the respiration rate and/or the heart rate by determining periodic behavior with certain characteristics in the detector measurement of the frequency of the electric field. For example, the respiration rate has periodicities in an expected range, and (if the effects of the respiration rate on the electric field have a sufficient quality measure) an expected range of magnitudes in changes in the detector measurement of the frequency of the electric field. Similarly, the heart rate has periodicities in a different (overlapping) expected range and a second expected range of magnitudes in changes in the detector measurement of the frequency of the electric field.

In some embodiments, the computation unit computes, in addition to and/or instead of a rate, a corresponding waveform. In a first example, the computation unit produces data providing the shape of the respiratory waveform (e.g., indicating how sharp or shallow breathing is, or indicating missed breaths). In a second example, the computation unit produces data providing the shape of the heartbeat (e.g., showing the systolic and diastolic regions, similar to a Wiggers diagram).

In some embodiments, results of the computation of one or more physiological parameters of one or more human bodies are tracked over a period of time, such as over a period of minutes, hours, days, weeks, months, and/or years, such as to detect trends indicating changes in health. In various embodiments, results of the computation unit (e.g., resting respiration rate and/or waveforms, resting heart rate and/or waveforms, etc.), are communicated to and stored on a remotely-located device such as a server. Software running on the server is able to analyze the results and determine trends and/or present the results in various ways for human consideration. In a first example, a change in the nighttime resting heart rate of a particular one of the human bodies over a period of days may be indicative of the onset of a COPD exacerbation. In a second example, a change in body mass, particularly in the limbs, of a particular one of the human bodies over a period of days may be indicative of edema. In a third example, a change in a number of times a patient gets out of bed at night is evidence of a urological problem, such as a urinary tract infection. In a fourth example, a relative amount of blood flow to a specific part of the body is computed (e.g., by determining a magnitude of a pulse wave), and a change in the relative amount of blood flow over time is determined. The change in the relative amount of blood flow is, for example, indicative of healing processes (restoring proper blood flow), or certain disease complications (that restrict blood flow to extremities). In a fifth example, computation of nighttime heart rate, nighttime respiration rate, and/or nighttime movement is used to determine sleep stages. Body movement and/or changes in body movement have been correlated to sleep stages and/or changes in sleep stages.

Remote Patient Monitoring with High Compliance

An example application of a BPCD enables Remote Patient Monitoring (RPM) with high (patient) compliance.

Achieving high compliance in daily (e.g., nighttime, every night) monitoring is important for various applications, such as monitoring the pulse and/or respiration rates of patients suffering from chronic diseases, such as COPD or CHF. It is also important for less severe diseases where remote monitoring is used and where high (e.g., at least 16 days per month) compliance is a requirement for various medical reimbursement codes.

Figure 13:
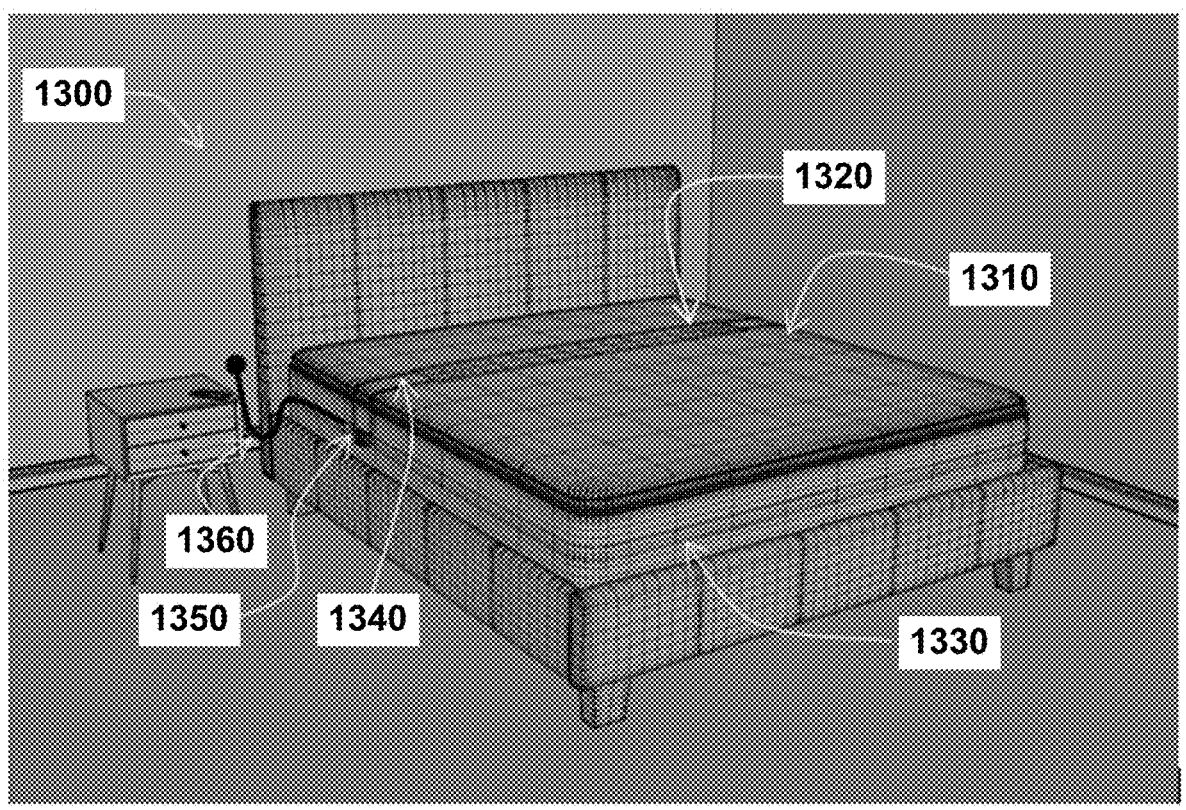
FIG. 13 is an overview diagram of a sensor and strap system attached to a bed mattress according to certain embodiments of the present disclosure.
Figure 14:
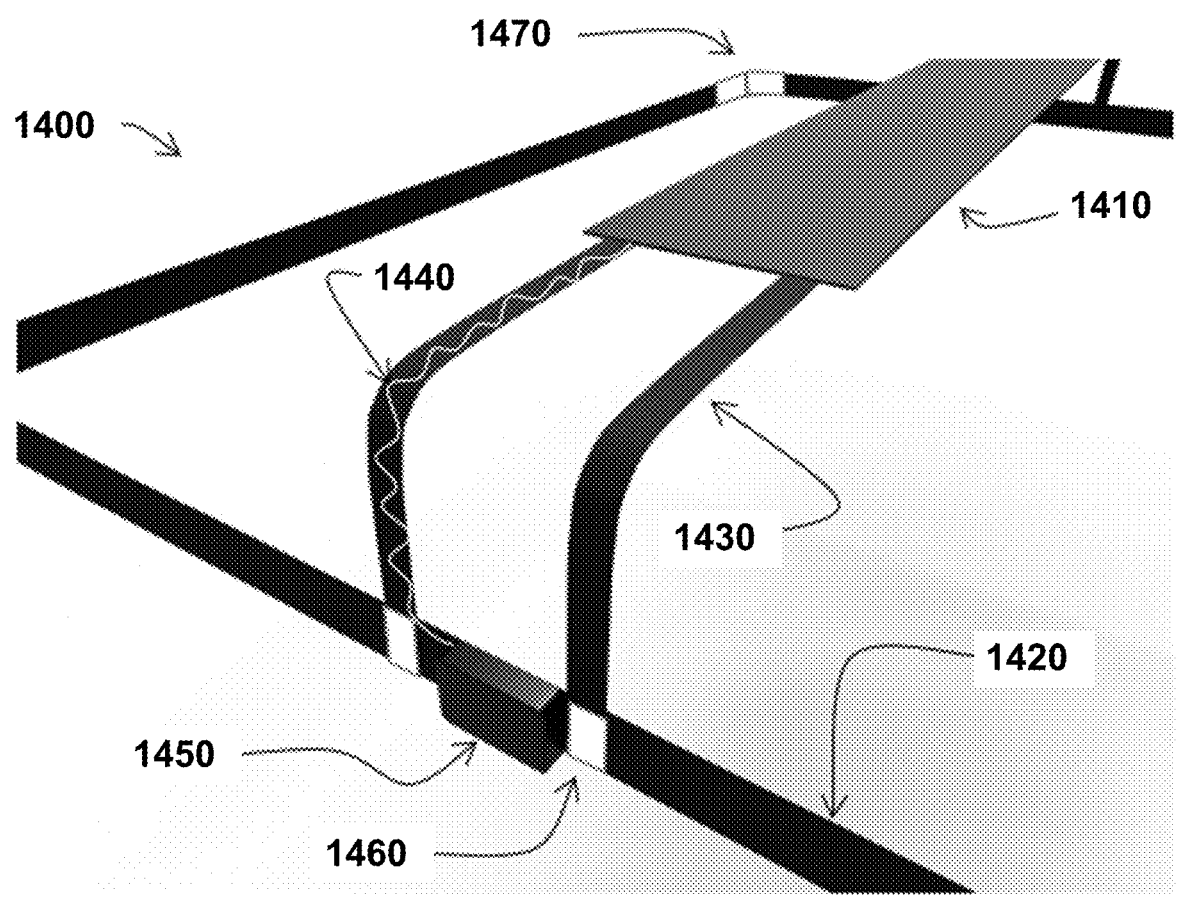
FIG. 14 is a diagram depicting a sensor, top straps, and circumferential straps and their attachments according to certain embodiments of the present disclosure.
Figure 15:
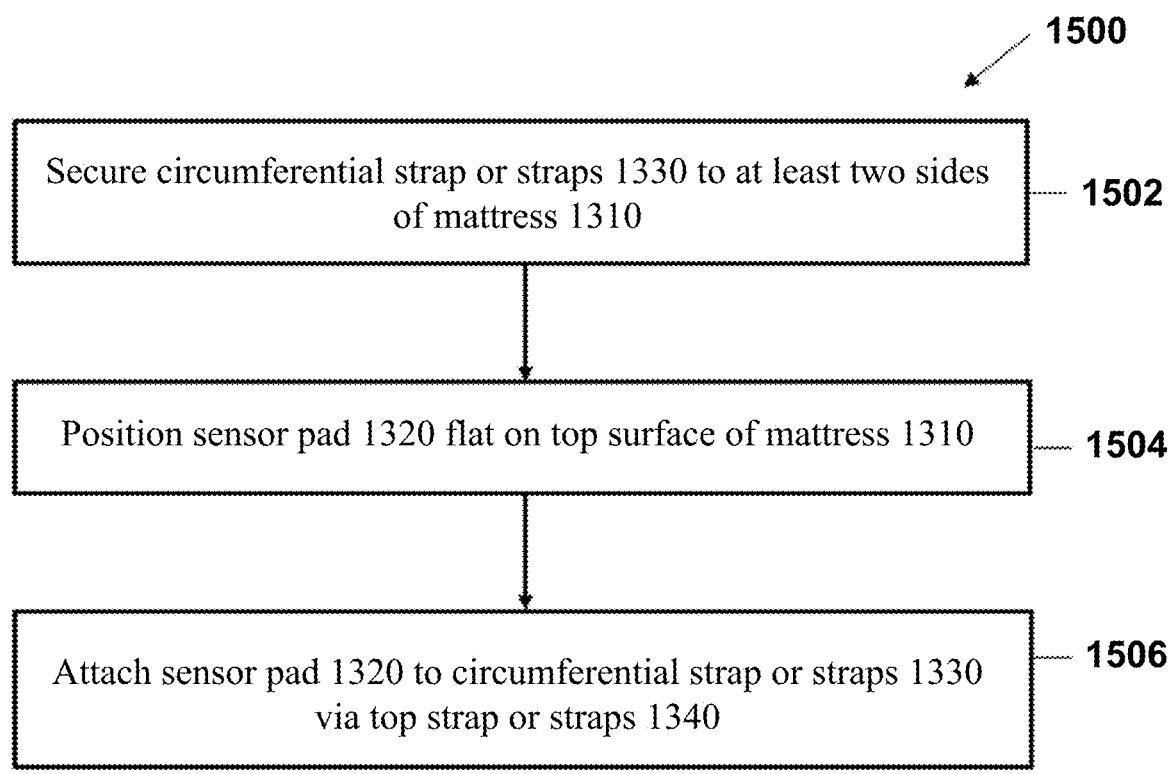
FIG. 15 illustrates a process for attaching and securing a sensor strap system according to certain embodiments of the present disclosure.

In some embodiments, an external sensor (e.g., an antenna in a flexible housing) of a BPCD is attached to and/or is part of a piece of furniture, such as a bed. For example, as illustrated in FIGS. 13 and 14 (described further below), the external sensor is in the form of a sensor strap configured to be secured to an object (e.g., a mattress, cushion, chair, conveyance, or other type of furniture). In various embodiments, the BPCD is powered from a wall socket (optionally with a battery and/or other power back-up in the event of a power outage). Because of the non-contact nature of the BPCD (where body parameters are computed through measurements of interactions of a body with an electric field generated by the BPCD), obtaining a patient's body parameters is possible without the patient deviating from his or her ordinary behaviors once the BPCD is placed in an appropriate location and connected to a power source. In contrast, other devices (e.g., wearables) have compliance issues such as requiring the patient to attach (e.g., wear) the device, and to keep the device charged. Even a weight scale requires patient interaction (e.g., standing on the scale to take a measurement) as compared to the BPCD where the only patient requirement is, for example, something done regardless (e.g., sleeping in bed). In this regard, in some embodiments and/or usage scenarios, the BPCD is said to be passive (in that, once installed, it requires no direct patient or clinician activity such as positioning, charging and/or wearing a device) and non-invasive (in that it requires minimal or no changes to the patient's lifestyle).

In various embodiments, the external sensor of the BPCD is attached (as a one-time operation) to a piece of furniture (e.g., a bed) where the patient spends time (e.g., sleeping), and the BPCD is connected to a power source (e.g., a wall socket). Thereafter, when the patient uses the piece of furniture (e.g., rests or sleeps in the bed), the BPCD is configured to compute one or more body parameters of the patient without any further required actions by the patient. In general terms, the BPCD is able to perform monitoring of a patient in a manner that is non-intrusive to the patient's lifestyle.

In an example of overnight monitoring, such as for monitoring nighttime resting pulse and/or respiration rates, patient compliance is achieved when the patient sleeps in a bed where the external sensor (antenna) of the BPCD is installed and operational. In some embodiments, depending on the type and/or positioning of one or more antennas of the BPCD, the patient may need to sleep on a particular side of a large (e.g., queen-size of king-size) bed for compliance. In other embodiments, a use of multiple antennas enables the BPCD to enable patient compliance with fewer or no restrictions on patient positioning within the bed.

Example Embodiments

What follows is a collection of example embodiments, including at least some explicitly enumerated as 'ECs' (Example Combinations), providing additional description of a variety of embodiment types in accordance with the concepts described in the present disclosure; these examples are not meant to be mutually exclusive, exhaustive, or restrictive; and the present disclosure is not limited to these example embodiments but rather encompasses numerous possible modifications and variations within the scope of the issued claims and their equivalents. Further, it is noted that each Example Combination described below is meant to be illustrative, and each Example Combination may be combined with any other Example Combination or any other techniques disclosed herein, even if not expressly indicated as such.

EC1) A method comprising: generating, with an electric field generator, an electric field at a nominal frequency; radiating the electric field through an antenna whose length is less than one half of a wavelength of oscillations at the nominal frequency; measuring a frequency of the electric field as it interacts with a human body in the reactive near-field region of the electric field; determining respective periodic behaviors in the measured frequency corresponding to movements of two or more internal organs of the human body; and computing respective rates of movement of the two or more internal organs based on the determined respective periodic behaviors in the measured frequency.

EC2) The method of EC1, wherein each of the respective periodic behaviors in the measured frequency is a superposition of respective multiple sources due to interactions of the two or more internal organs with other components of the human body.

EC3) The method of EC1, wherein the determining uses a time-domain technique to determine the respective periodic behaviors in the measured frequency.

EC4) The method of EC3, wherein the time-domain technique comprises an autocorrelation technique.

EC5) The method of EC1, wherein the determining uses a frequency-domain technique to determine the respective periodic behaviors in the measured frequency.

EC6) The method of EC5, wherein the frequency-domain technique comprises a transform technique.

EC7) The method of EC6, wherein the transform technique comprises a Fast Fourier Transform (FFT) technique.

EC8) The method of EC1, wherein a frequency of a particular one of the determined respective periodic behaviors in the measured frequency is between 10 Hz and 200 Hz.

EC9) The method of EC8, wherein the nominal frequency is between 10 MHz and 100 MHz.

EC10) The method of EC8, wherein the antenna is a two-wire antenna.

EC11) The method of EC1, wherein the electric field generator comprises a differential oscillator.

EC12) The method of EC11, wherein the differential oscillator is an inductor-capacitor tank oscillator.

EC13) The method of EC1, wherein the measuring is via a differential frequency demodulator.

EC14) The method of EC13, wherein the electric field generator comprises a differential oscillator.

EC15) The method of EC13, further comprising dynamically adjusting the nominal frequency to maintain the measured frequency within a linear range of the differential frequency demodulator.

EC16) The method of EC1, further comprising dynamically adjusting the nominal frequency in response to movement of the human body.

EC17) The method of EC16, wherein the movement of the human body comprises the human body rolling over.

EC18) The method of EC16, wherein the movement of the human body comprises the human body changing from a supine position to a sitting position.

EC19) The method of EC1, wherein the respective periodic behaviors comprise respective quasiperiodic behaviors.

EC20) The method of EC1, wherein one of the respective rates of the movement comprises a heart rate.

EC21) The method of EC1, wherein the respective rates of the movement of the two or more internal organs comprise a heart rate and a respiration rate.

EC22) The method of EC21, wherein the human body is on a bed;
wherein the antenna is underneath at least a covering of the bed; and wherein the heart rate is a nighttime resting heart rate and the respiration rate is a nighttime resting respiration rate.

EC23) The method of EC22, further comprising not using one or more portions of the measured frequency in the determining the respective periodic behaviors in the measured frequency, the one or more portions of the measured frequency corresponding to respective periods of time in which the measured frequency is not indicative of nighttime resting behavior of the human body.

EC24) The method of EC23, wherein one of the respective periods of time is due to excessive movement of the human body.

EC25) The method of EC23, wherein one of the respective periods of time is due to the electric field interacting with a second body other than the human body.

EC26) The method of EC1, wherein an electrical length of the antenna is at least six inches.

EC27) The method of EC1, wherein an electrical length of the antenna is at least twelve inches.

EC28) The method of EC1, wherein the measuring is via a circuit coupled to the electric field generator.

EC29) The method of EC28, wherein the measuring measures the frequency of the generated electric field as it changes due to interactions with the human body in the reactive near-field region of the electric field.

EC30) The method of EC1, wherein the measuring the frequency of the electric field measures the frequency of the electric field generator as the frequency changes due to the interactions with the human body.

EC31) The method of EC1, wherein the measuring the frequency of the electric field measures changes in the frequency of the electric field generator as the frequency changes due to the interactions with the human body.

EC32) The method of EC1, wherein the measuring the frequency of the electric field measures the frequency of the electric field generator compared to the nominal frequency as the frequency changes due to the interactions with the human body.

EC33) The method of EC1, wherein the antenna is a differential 2c3 antenna.

EC34) The method of EC1, wherein the antenna is an interdigitated antenna.

EC35) The method of EC1, wherein the antenna is a differential antenna.

EC50) A method comprising: generating, with an electric field generator, an electric field at a nominal frequency; measuring, at a succession of time points, a frequency of the electric field, the frequency of the electric field changing over time due to interactions with a human body subject to the electric field; determining respective periodic behaviors in the measured frequency indicative of movement of each of one or more internal organs of the human body; computing a respective rate according to the respective periodic behaviors of each of the one or more internal organs of the human body; ascertaining that a portion of the measured frequency between a first and a second one of the succession of time points does not correspond to a physiological process of at least one of the one or more internal organs; and blanking, in response to the ascertaining, the portion of the measured frequency so that the portion of the measured frequency is not used in the computing.

EC51) The method of EC50, further comprising radiating the electric field via an antenna; and wherein the human body is within the reactive near-field region of the radiated electric field.

EC52) The method of EC50, wherein, during a first subset of the succession of time points, the human body is within a reactive near-field region of the electric field.

EC53) The method of EC52, wherein, during a second subset of the succession of time points, the human body is not within the reactive near-field region of the electric field.

EC54) The method of any of EC52 or EC53, wherein the respective periodic behaviors are due to coupling of the one or more internal organs of the human body to a source of the electric field.

EC55) The method of any of EC52 through EC54, wherein the nominal frequency is between 10 MHz and 100 MHz.

EC56) The method of any of EC52 through EC55, wherein electric field radiates from one or more wires and the human body is not in contact with the one or more wires.

EC57) The method of EC56, wherein, during the first subset of the succession of time points, the human body is within three feet of the one or more wires.

EC58) The method of any of EC52 through EC56, wherein the second subset of the succession of time points comprises the ones of the succession of time points between the first and the second one of the succession of time points.

EC59) The method of any of EC52 through EC56, wherein, between the first and the second one of the succession of time points, a second body other than the human body is within the reactive near-field region of the electric field.

EC60) The method of EC50, wherein the one or more internal organs comprise a femoral artery.

EC61) The method of EC50, wherein the one or more internal organs comprise a heart and lungs.

EC62) The method of EC61, wherein the computing computes a resting heart rate and a resting respiration rate.

EC63) The method of EC62, wherein the human body is on a bed; and wherein the resting heart rate and the resting respiration rate are a nighttime resting heart rate and a nighttime resting respiration rate.

EC64) The method of EC50, wherein the ascertaining is according to a change in the measured frequency being greater than a threshold.

EC65) The method of EC50, wherein the ascertaining is according to the measured frequency being outside of a threshold range from the nominal frequency.

EC66) The method of EC50, wherein the succession of time points is a first succession of time points; and further comprising measuring, at a second succession of time points, an amplitude of the electric field.

EC67) The method of EC66, wherein the ascertaining is according to the measured amplitude being greater than a threshold.

EC68) The method of EC66, wherein the ascertaining is according to the measured amplitude being less than a threshold.

EC69) The method of EC66, further comprising determining, based on the measured amplitude, at which of the second succession of time points the human body is within close proximity to a radiator of the electric field.

EC70) The method of EC50, wherein the portion of the measured frequency that does not correspond to the physiological process of the one or more internal organs corresponds to a movement of the human body.

EC71) The method of EC70, wherein the movement of the human body is a movement of a limb of the human body.

EC72) The method of EC70, wherein the movement of the human body is a movement of a torso of the human body due to the human body rolling over.

EC73) The method of EC70, further comprising dynamically adjusting the nominal frequency in response to the movement of the human body.

EC74) The method of EC70, further comprising computing sleep stages of the human body using, at least in part, information of the movement of the human body.

EC75) The method of EC50, wherein the determining respective periodic behaviors in the measured frequency uses time-domain techniques.

EC76) The method of EC50, wherein the determining respective periodic behaviors in the measured frequency uses frequency-domain techniques.

EC77) The method of EC50, wherein the measuring the frequency of the electric field measures the frequency of the electric field generator as the frequency changes due to the interactions with the human body.

EC78) The method of EC50, wherein the measuring the frequency of the electric field measures changes in the frequency of the electric field generator as the frequency changes due to the interactions with the human body.

EC100) A system comprising: an electric field generator configured to radiate via an antenna an electric field at a nominal frequency; a detector configured to measure a frequency of the electric field as the electric field interacts with a body in the reactive near-field region of the electric field; and a computation unit configured to (a) determine respective periodic behaviors in the measured frequency indicative of movement of each of two or more internal components of the body, and (b) compute a respective parameter of each of the two or more internal components of the body according to the respective periodic behaviors in the measured frequency.

EC101) The system of EC100, further comprising the antenna.

EC102) A system comprising: an antenna radiating an antenna an electric field at a nominal frequency; a detector configured to measure a frequency of the electric field as the electric field interacts with a body in the reactive near-field region of the electric field; and a computation unit configured to (a) determine respective periodic behaviors in the measured frequency indicative of movement of each of two or more internal components of the body, and (b) compute a respective parameter of each of the two or more internal components of the body according to the respective periodic behaviors in the measured frequency.

EC103) The system of EC102, further comprising an electric field generator configured to radiate the electric field via the antenna.

EC104) The system of any of EC100 through EC103, wherein the respective parameter of each of the two or more internal components of the body comprises a respective rate of the movement of each of the two or more internal components of the body.

EC105) The system of EC104, wherein the body is a human body; and wherein the respective rate of the movement of one of the two or more internal components of the body is a heart rate.

EC106) The system of EC105, wherein the heart rate is a nighttime resting heart rate.

EC107) The system of EC104, wherein the body is a human body; and wherein the respective rate of the movement of one of the two or more internal components of the body is a respiration rate, and the respective rate of the movement of another one of the two or more internal components of the body is a heart rate.

EC108) The system of any of EC100 through EC103, wherein the respective parameter of at least one of the two or more internal components of the body comprises a respective waveform of the movement of the at least one of the two or more internal components of the body.

EC109) The system of EC108, wherein the respective waveform of the movement of the at least one of the two or more internal components of the body is a respiratory waveform.

EC110) The system of any of EC100 through EC103, wherein the body is a human body and the two or more internal components of the body are two or more internal organs of the human body.

EC111) The system of EC110, wherein at least one of the two or more internal organs of the human body is a heart of the human body.

EC112) The system of EC110, wherein the two or more internal organs of the human body comprise a heart of the human body and lungs of the human body.

EC113) The system of any of EC100 through EC103, wherein the nominal frequency is between 10 MHz and 100 MHz.

EC114) The system of any of EC100 through EC103, wherein the antenna is a two-wire antenna.

EC115) The system of any of EC100, EC101 or EC103, wherein the electric field generator comprises a differential oscillator.

EC116) The system of EC115, wherein the differential oscillator is a differential tank oscillator.

EC117) The system of any of EC100 through EC103, wherein the detector comprises a quadrature demodulator.

EC118) The system of EC117, wherein the quadrature demodulator is a differential quadrature demodulator.

EC119) The system of any of EC100 through EC103, wherein the detector comprises a sample-and-hold circuit and an analog-to-digital converter.

EC120) The system of EC119, wherein the sample-and-hold circuit is a differential sample-and-hold circuit.

EC121) The system of any of EC100 through EC103, wherein the detector comprises a wideband analog-to-digital converter.

EC122) The system of any of EC100 through EC103, wherein the computation unit comprises a signal processor.

EC123) The system of EC122, wherein the signal processor is a digital signal processor.

EC124) The system of any of EC100 through EC103, further comprising an analog-to-digital converter between the detector and the computation unit.

EC125) The system of any of EC100, EC101, or EC103, wherein the electric field generator and the detector each comprises respective differential circuits.

EC126) The system of EC100 through EC103, further comprising a tuner configured to dynamically adjust the nominal frequency in response to movement of the body.

EC127) The system of any of EC100 through EC103, wherein the detector is configured to measure the frequency of the electric field generator as the frequency changes due to the interactions with the body.

EC128) The system of any of EC100 through EC103, wherein the detector is configured to measure changes in the frequency of the electric field generator as the frequency changes due to the interactions with the body.

EC129) The system of any of EC100, wherein the detector is configured to measure the frequency of the electric field generator compared to the nominal frequency as the frequency changes due to the interactions with the human body.

EC130) The system of any of EC100 through EC103, wherein the antenna is a differential 2c3 antenna.

EC131) The system of any of EC100 through EC103, wherein the antenna is an interdigitated antenna.

EC132) The system of any of EC100 through EC103, wherein the antenna is a differential antenna.

EC150) A system comprising: one or more electric field generators operating at respective nominal frequencies; one or more antennas connected to the one or more electric field generators and configured to radiate respective electric fields; one or more detectors configured to measure respective frequencies of the respective electric fields as each of the respective electric fields interacts with two or more bodies in the reactive near-field region of the respective electric field; and a computation unit configured to (a) determine a respective periodic behavior in at least one of the measured respective frequencies indicative of movement of at least one internal component of a particular one of the two or more bodies, and (b) compute a respective rate of the movement of the at least one internal component of the particular body according to the respective periodic behavior in the at least one of the measured respective frequencies.

EC151) The system of EC150, wherein each of the one or more antennas is connected to a respective one of the one or more electric field generators.

EC152) The system of EC150, wherein at least two of the one or more antennas are connected to a same one of the one or more electric field generators.

EC153) The system of EC152, wherein the at least two of the one or more antennas are connected to the same one of the one or more electric field generators via a switch.

EC154) The system of EC153, wherein the at least two of the one or more antennas are used in a time-division-multiplexed manner.

EC155) The system of any of EC150 through EC154, wherein each of the one or more electric field generators is connected to a respective one of the one or more detectors.

EC156) The system of any of EC150 through EC154, wherein at least two of the one or more electric field generators are connected to a same one of the one or more detectors.

EC157) The system of any of EC150 through EC154, wherein the at least two of the one or more electric field generators are connected to the same one of the one or more detectors via a switch.

EC158) The system of EC156, wherein all of the one or more electric field generators are connected to the same one of the one or more detectors via a switch.

EC159) The system of any of EC150 through EC158, wherein the particular body is a human body.

EC160) The system of EC159, wherein the human body is a first human body; and wherein another one of the two or more bodies is a second human body different from the first human body.

EC161) The system of EC159, wherein another one of the two or more bodies is a living body other than a human body.

EC162) The system of EC159, wherein another one of the two or more bodies is an inanimate body.

EC163) The system of any of EC160 through EC162 wherein the computation unit is further configured to compute the respective rate of the movement of the at least one internal component of the particular body despite interactions of the another one of the bodies with the respective electric fields.

EC164) The system of EC163, wherein the computation unit is further configured to not use a portion of the measured respective frequencies of the respective electric fields in which the interactions of the another one of the bodies with the respective electric fields cause the computation unit to fail to determine the respective periodic behavior in the at least one of the measured respective frequencies.

EC165) The system of EC163, wherein the respective nominal frequency of a first one of the one or more electric field generators is different from the respective nominal frequency of a second one of the one or more electric field generators.

EC166) The system of EC165, wherein the respective nominal frequency of the first one of the one or more electric field generators and the respective nominal frequency of the second one of the one or more electric field generators are each between 10 MHz and 100 MHz.

EC167) The system of EC165, wherein a difference between the respective nominal frequency of the first one of the one or more electric field generators and the respective nominal frequency of the second one of the one or more electric field generators is larger than an expected change in the at least one of the measured respective frequencies due to the movement of the at least one internal component of the particular body.

EC168) The system of any of EC160 through EC162, further comprising a tuner configured to dynamically adjust the respective nominal frequency of at least one of the electric field generators in response to movement of the another one of the bodies.

EC169) The system of any of EC150 through EC158, wherein at least one of the one or more detectors comprises a frequency demodulator.

EC170) The system of EC169, wherein the frequency demodulator is a differential quadrature demodulator.

EC171) The system of any of EC150 through EC158, wherein the detector comprises a differential sample-and-hold circuit and an analog-to-digital converter.

EC172) The system of any of EC150 through EC158, further comprising a tuner configured to dynamically adjust at least one of the respective nominal frequencies in response to movement of the particular body.

EC173) The system of any of EC150 through EC158, wherein the one or more electric field generators are two or more electric field generators; and wherein the computation unit is further configured to (a) determine a respective periodic behavior in each of two or more of the measured respective frequencies; and (b) compute the respective rate of the movement of the at least one internal component of the particular body according to the respective periodic behaviors in each of the two or more of the measured respective frequencies.

EC174) The system of any of EC150 through EC158, wherein the one or more electric field generators are two or more electric field generators; wherein the at least one of the measured respective frequencies is a first one of the measured respective frequencies; and wherein the computation unit is further configured to compute the respective rate of the movement of the at least one internal component of the particular body according to the respective periodic behavior in the first one of the measured respective frequencies and according to a second one of the measured respective frequencies different from the first one of the measured respective frequencies.

EC175) The system of any of EC150 through EC158, wherein the one or more electric field generators are two or more electric field generators; and wherein the computation unit is further configured to determine an effect of a second of the two or more bodies other than the particular body on the at least one of the measured respective frequencies, and to compute the respective rate of the movement of the at least one internal component of the particular body according to the determined effect of the second body on the at least one of the measured respective frequencies.

EC176) The system of EC175, wherein the at least one of the measured respective frequencies is a first one of the measured respective frequencies; and wherein the computation unit is further configured to determine the effect of the second body on the first measured respective frequency according to an effect of the second body on a second one of the measured respective frequencies different from the first one of the measured respective frequencies.

EC200) A system comprising: an electric field generator comprising a differential oscillator configured to oscillate at a nominal frequency, and connected to an antenna configured to radiate an electric field; a differential detector configured to measure a frequency of the electric field as it interacts with a body in the reactive near-field region of the electric field; and a computation unit configured to (a) determine respective periodic behaviors in the measured frequency indicative of movement of one or more internal components of the body, and (b) compute a respective rate of the movement of each of the one or more internal components of the body according to the respective periodic behaviors in the measured frequency.

EC201) The system of EC200, further comprising the antenna.

EC202) The system of EC201, wherein the antenna is a two-wire antenna.

EC203) The system of any of EC200 through EC202, wherein the differential oscillator comprises a differential tank oscillator.

EC204) The system of any of EC200 through EC202, wherein the differential oscillator comprises a differential resonator.

EC205) The system of any of EC200 through EC204, wherein the differential detector comprises a differential quadrature demodulator.

EC206) The system of any of EC200 through EC204, wherein the differential detector comprises a differential sample-and-hold circuit and an analog-to-digital converter.

EC207) The system of EC200 through EC204, wherein the differential detector comprises a differential wideband analog-to-digital converter.

EC208) The system of EC200 through EC207, wherein the body is a human body.

EC209) The system of EC208, wherein the one of the one or more internal components of the body comprise a heart of the human body.

EC210) The system of EC208, wherein the one or more internal components of the body comprise a femoral artery of the human body.

EC211) The system of EC208, wherein the one or more internal components of the body comprise a heart of the human body and lungs of the human body.

EC212) The system of EC208, wherein one of the respective rates is a heart rate.

EC213) The system of EC208, wherein the respective rates comprise a heart rate and a respiration rate.

EC214) The system of any of EC212 or EC213, wherein the heart rate is a nighttime resting heart rate.

EC215) The system of EC214, wherein the computation unit is further configured, in computation of the nighttime resting heart rate, to not use portions of the measured frequency that are not indicative of the respective periodic behaviors in the measured frequency indicative of movement of the heart.

EC216) The system of EC214, wherein the computation unit is further configured, in computation of the nighttime resting heart rate, to not use a portion of the measured frequency that exhibits a frequency change greater than a determined threshold.

EC217) The system of any of EC200 through EC216, wherein the antenna is a differential antenna.

EC250) A system comprising: an electric field generator configured to radiate an electric field at a nominal frequency; a detector configured to measure a frequency of the electric field as the electric field interacts with a body in the reactive near-field region of the electric field; a computation unit configured to (a) determine respective periodic behaviors in the measured frequency indicative of movement of each of one or more internal components of the body, and (b) compute a respective rate of the movement of each of the one or more internal components of the body according to the respective periodic behaviors in the measured frequency; and a tuner connected to the electric field generator and configured to adjust the nominal frequency.

EC251) The system of EC250, further comprising an antenna connected to the electric field generator; and wherein the antenna is configured to radiate the electric field.

EC252) The system of EC251, wherein the antenna is a two-wire antenna.

EC253) The system of EC250, wherein the tuner is configured to adjust the nominal frequency according to a measured amplitude of the electric field.

EC254) The system of EC250, wherein the tuner is configured to adjust the nominal frequency according to the measured frequency.

EC255) The system of EC254, wherein the tuner is configured to adjust the nominal frequency when the measured frequency diverges from the nominal frequency by more than a determined threshold.

EC256) The system of any of EC254 or EC255, wherein the tuner comprises an analog tuning circuit responsive to the measured frequency.

EC257) The system of any of EC250, or EC253 through EC256, wherein the detector comprises a frequency demodulator.

EC258) The system of EC257, wherein the frequency demodulator is a quadrature demodulator.

EC259) The system of EC258, wherein the tuner is configured to adjust the nominal frequency to maintain the measured frequency within a linear range of the frequency demodulator.

EC260) The system of any of EC250, or EC253 through EC256, wherein a signal processor comprises the tuner.

EC261) The system of EC260, wherein the signal processor is a digital signal processor.

EC262) The system of EC261, wherein the signal processor further comprises the computation unit.

EC263) The system of any of EC260 through EC262, wherein the detector comprises a frequency demodulator.

EC264) The system of any of EC260 through EC262, wherein the detector comprises a sample-and-hold circuit and an analog-to-digital converter.

EC265) The system of any of EC250, or EC253 through EC264, wherein the electric field generator comprises a differential oscillator.

EC266) The system of EC265, wherein the detector comprises differential circuitry.

EC267) The system of EC266, wherein the detector comprises a differential frequency demodulator.

EC268) The system of any of EC250, or EC253 through EC256, or EC260 through EC267, wherein the body is a human body.

EC269) The system of EC268, wherein the one or more internal components of the body comprise a femoral artery of the human body.

EC270) The system of EC269, wherein the computation unit is configured to compute a heart rate of the human body according to the respective periodic behaviors in the measured frequency indicative of movement of the femoral artery.

EC271) The system of EC268, wherein the one or more internal components of the body comprise a heart of the human body.

EC272) The system of EC268, wherein the one or more internal components of the body comprise a heart of the human body and lungs of the human body.

EC273) The system of any of EC271 or EC272, wherein the respective rate of the movement of the heart of the human body is a nighttime resting heart rate.

EC274) The system of EC273, further comprising an antenna connected to the electric field generator; and wherein the antenna is configured to radiate the electric field EC275) The system of EC274, wherein the antenna is a two-wire antenna.

EC276) The system of EC274, wherein a sensor strap positioned on a bed comprises the antenna; and wherein the human body is on the bed at least some of the time.

EC277) The system of EC274, wherein the human body is not in direct contact with the antenna.

EC278) The system of any of EC273 through EC277, wherein the computation unit is further configured to compute the nighttime resting heart rate by blanking a portion of the measured frequency not corresponding to the respective periodic behaviors in the measured frequency indicative of movement of the heart of the human body.

EC279) The system of EC250, wherein the tuner is configured to adjust the nominal frequency so as to maintain an output of the detector at a constant voltage.

EC280) The system of EC279, wherein the output of the detector is an output of a frequency demodulator of the detector.

EC281) The system of EC279, wherein the constant voltage is a constant peak voltage.

EC282) The system of EC250, wherein the tuner is configured to adjust the nominal frequency with a time constant that is longer than the respective periodic behaviors in the measured frequency indicative of movement of each of one or more internal components of the body.

EC283) The system of EC282, wherein the time constant is at least ten times longer than an expected value of the respective periodic behaviors in the measured frequency indicative of movement of each of one or more internal components of the body.

EC300) A method comprising: generating, with an electric field generator, an electric field at a nominal frequency; radiating the electric field through an antenna; measuring a frequency of the electric field as it interacts with a body in the reactive near-field region of the electric field; determining respective periodic behaviors in the measured frequency corresponding to movements of one or more internal components of the body; computing respective rates of movement of the one or more internal components of the body based on the determined respective periodic behaviors in the measured frequency; and adjusting the nominal frequency to improve the determining of the respective periodic behaviors in the measured frequency.

EC301) The method of EC300, wherein the respective periodic behaviors comprise respective quasiperiodic behaviors.

EC302) The method of any of EC300 or EC301, wherein the determining the respective periodic behaviors in the measured frequency uses time-domain techniques.

EC303) The method of any of EC300 or EC301, wherein the determining the respective periodic behaviors in the measured frequency uses frequency-domain techniques.

EC304) The method of any of EC300 through EC303, wherein the adjusting the nominal frequency is according to the measured frequency.

EC305) The method of any of EC300 through EC303, further comprising adjusting the nominal frequency when the measured frequency diverges from the nominal frequency by more than a determined threshold.

EC306) The method of any of EC300 through EC305, wherein the adjusting the nominal frequency is via analog tuning circuit responsive to the measured frequency.

EC307) The method of any of EC300 through EC305, wherein the adjusting the nominal frequency is via a signal processor.

EC308) The method of any of EC300 through EC307, wherein the adjusting the nominal frequency is in response to the determining not finding at least one of the respective periodic behaviors in the measured frequency.

EC309) The method of any of EC300 through EC308, wherein the measuring the frequency is via a frequency demodulator; and wherein the adjusting the nominal frequency maintains the measured frequency within a linear range of the frequency demodulator.

EC310) The method of any of EC300 through EC309, wherein the adjusting the nominal frequency uses servo techniques to improve a quality measure of at least one of the respective periodic behaviors in the measured frequency.

EC311) The method of EC310, wherein the quality measure comprises a signal-to-noise ratio.

EC312) The method of any of EC300 through EC310, wherein the body is a human body.

EC313) The method of EC312, wherein the one or more internal components of the body comprise a femoral artery of the human body.

EC314) The method of EC313, further comprising computing a heart rate of the human body according to the respective periodic behaviors in the measured frequency indicative of movement of the femoral artery.

EC315) The method of EC312, wherein the one or more internal components of the body comprise a heart of the human body and lungs of the human body.

EC316) The method of EC315, wherein the respective rate of the movement of the heart of the human body is a nighttime resting heart rate; and wherein the respective rate of the movement of the lungs of the human body is a nighttime resting respiration rate.

EC350) A method comprising: generating, with an electric field generator, an electric field at a nominal frequency and a nominal amplitude; radiating the electric field through an antenna; measuring a frequency and an amplitude of the electric field as it interacts with a body in the reactive near-field region of the electric field; determining respective periodic behaviors in the measured frequency corresponding to movements of one or more internal components of the body; computing respective rates of movement of the one or more internal components based on the determined respective periodic behaviors in the measured frequency; and adjusting the nominal amplitude according to the measured amplitude.

EC351) The method of EC350, wherein the adjusting the nominal amplitude is in response to the measured amplitude going below a determined lower threshold.

EC352) The method of EC350, wherein the adjusting the nominal amplitude is in response to the measured amplitude going above a determined upper threshold.

EC353) The method of EC350, wherein the adjusting the nominal amplitude is in response to the measured amplitude being outside of a determined range.

EC354) The method of EC350, wherein the adjusting the nominal amplitude maintains the measured amplitude of the electric field at or near a determined amplitude.

EC355) The method of EC354, wherein the determined amplitude is the nominal amplitude.

EC356) The method of EC350, wherein the adjusting the nominal amplitude is in response to an insufficient quality measure of at least one of the respective periodic behaviors in the measured frequency.

EC357) The method of EC356, wherein the quality measure comprises a signal-to-noise ratio.

EC358) The method of any of EC350 through EC357, further comprising, adjusting the nominal frequency to improve the determining of the respective periodic behaviors in the measured frequency.

EC359) The method of any of EC350 through EC358, wherein the body is a human body.

EC360) The method of EC359, further comprising determining, based on the measured amplitude, whether the human body is within close proximity to the antenna.

EC361) The method of any of EC359 or EC360 with any of the limitations of EC313 through EC316.

EC362) The method of EC350, wherein the adjusting the nominal amplitude is configured to not increase the nominal amplitude beyond a determined point where a total radiated power level would exceed a determined level.

EC363) The method of EC350, wherein the adjusting the nominal amplitude is configured to adjust the nominal amplitude with a time constant that is longer than the respective periodic behaviors in the measured frequency corresponding to movements of one or more internal components of the body.

EC364) The method of EC363, wherein the time constant is at least ten times longer than an expected value of the respective periodic behaviors in the measured frequency corresponding to movements of one or more internal components of the body.

EC400) A system comprising: an electric field generator configured to radiate an electric field at a nominal frequency; a detector configured to measure a frequency of the electric field as the electric field interacts with a human body in the reactive near-field region of the electric field; and a computation unit configured to (a) determine respective periodic behaviors in the measured frequency indicative of movement of each of one or more internal organs of the human body, and (b) compute a respective rate of the movement of each of the one or more internal organs of the human body according to the respective periodic behaviors in the measured frequency; and wherein the respective rate of the movement of each of the one or more internal organs of the human body is a nighttime resting rate computed over a duration in which there are periods where the human body moves both when asleep, and when not asleep but in the reactive near-field region of the electric field.

EC401) The method of EC400, wherein the duration is at least three hours.

EC402) The method of any of EC400 or EC401, wherein over the duration the human body changes position from supine to resting on its side.

EC403) The method of any of EC400 or EC401, wherein over the duration the human body wakes up and temporarily changes from a reclining posture to a sitting posture.

EC404) The method of any of EC400 or EC401, wherein there is at least one period of the duration in which the human body is not in the reactive near-field region of the electric field.

EC405) The method of any of EC400 through EC404, wherein one of the one or more internal organs is a heart of the human body; and wherein the respective rate of the movement of the heart is a nighttime resting heart rate.

EC406) The method of any of EC400 through EC404, wherein a first one of the one or more internal organs is a heart of the human body; wherein a second one of the one or more internal organs is lungs of the human body; wherein the respective rate of the movement of the heart is a nighttime resting heart rate; and wherein the respective rate of the movement of the lungs is a nighttime resting respiration rate.

EC407) The method of any of EC400 through EC406, wherein the electric field is radiated through an antenna.

EC408) The method of EC407, wherein the antenna is a two-wire antenna.

EC409) The method of EC407, wherein a sensor strap positioned on a bed comprises the antenna; and wherein the human body is on the bed during at least part of the duration.

EC410) The method of any of EC400 through EC409, further comprising communicating the nighttime resting rate of each of the one or more internal organs of the human body to a server.

EC411) The method of EC410, further comprising storing, on the server and over each of a succession of days, the nighttime resting rate of each of the one or more internal organs of the human body.

EC412) The method of EC411, wherein the succession of days is at least three days.

EC413) The method of EC411, wherein the succession of days is at least seven days.

EC414) The method of EC411, wherein the succession of days is at least ten days.

EC415) The method of any of EC411 through EC414, further comprising predicting, using the nighttime resting rates stored on the server, an onset of a disease condition of the human body.

EC450) A method of predicting a condition of a human body, comprising: generating, with an electric field generator, an electric field at a nominal frequency; measuring, at each of a succession of time points during a measuring period, a frequency of the electric field, the frequency of the electric field changing over time due to interactions with multiple internal organs of a human body subject to the electric field; determining respective periodic behaviors in the measured frequency indicative of movement of each of one or more of the internal organs of the human body; computing, for each of the one or more of the internal organs of the human body and using each of multiple computation points during the measuring period, a respective rate of the movement of each of the one or more of the internal organs of the human body according to the respective periodic behaviors in the measured frequency; and using the respective rate of the movement of each of the one or more of the internal organs of the human body computed using the multiple computation points to predict a condition of the human body.

EC451) The method of EC450, further comprising radiating the electric field through an antenna; and wherein the respective periodic behaviors are determined during periods in which the human body is within the reactive near-field region of the electric field.

EC452) The method of EC451, wherein the human body is not within the reactive near-field region of the electric field during at least a portion of the measuring period.

EC453) The method of EC451, wherein the human body changes position during the measuring period.

EC454) The method of any of EC451 through EC453, wherein the antenna is positioned on a bed; and wherein the human body is not in direct contact with the antenna during the measuring period.

EC455) The method of any of EC451 through EC453, wherein a sensor strap positioned on a bed comprises the antenna; and wherein the human body is on the bed during at least a portion of the measuring period.

EC456) The method of any of EC450 through EC455, further comprising blanking measurements made at one or more of the succession of time points where a quality measure of the measured frequency for at least one of the respective periodic behaviors is insufficient.

EC457) The method of any of EC450 through EC455, further comprising: measuring, at each of the succession of time points during the measuring period, an amplitude of the electric field.

EC458) The method of EC457, further comprising blanking measurements made at one or more of the succession of time points where the measured amplitude is outside of a determined range.

EC459) The method of EC457, further comprising determining, based on the measured amplitude, at which of the succession of time points the human body is within close proximity to a radiator of the electric field.

EC460) The method of EC459, further comprising determining, based on the measured amplitude, at each of the succession of time points, a measure of how close the human body is to the radiator of the electric field.

EC461) The method of any of EC450 through EC460, wherein the measuring period comprises multiple days; wherein the respective rates are nighttime resting rates; and wherein the condition of the human body is onset of a disease condition.

EC462) The method of EC461, wherein the one or more of the internal organs of the human body include the heart of the human body, and wherein the onset of the disease condition is onset of a Chronic Obstructive Pulmonary Disease (COPD) exacerbation.

EC463) The method of EC461, wherein the one or more of the internal organs of the human body include the heart of the human body, and wherein the onset of the disease condition is worsening of Congestive Heart Failure (CHF) symptoms.

EC464) The method of any of EC461 through EC463, wherein the one or more of the internal organs of the human body include lungs of the human body.

EC465) The method of any of EC450 through EC460, wherein the measuring period comprises multiple hours; wherein the respective rates of the one or more of the internal organs comprise a respiration rate; and wherein the condition of the human body is a sleep stage of the human body.

EC466) The method of EC465, further comprising determining movement of the human body; and further using the movement of the human body to detect the sleep stage of the human body.

EC500) The system of any of EC100 through EC126, EC150 through EC176, EC200 through EC216, EC250 through EC278, or EC400 through EC409, further comprising a network connection to a server.

EC501) The system of EC500, wherein the network connection is a wireless connection.

EC502) The system of EC501, wherein the wireless connection is a cellular connection.

EC503) The system of EC502, wherein the cellular connection is a 5G connection.

EC504) The system of EC501, wherein the wireless connection is an 802.11 connection.

EC505) The system of EC500, wherein the network connection is a wired connection.

EC506) The system of EC505, wherein the wired connection is an Ethernet connection.

EC507) The system of EC500, wherein the computation unit is configured to communicate with the server via the network connection.

EC508) The system of EC507, wherein data determined and/or computed by the computation unit is configured to be communicated to the server.

EC509) The system of EC508, wherein the communication is periodic.

EC510) The system of EC509, where the periodic communication is hourly during a monitoring duration.

EC511) The system of EC509, wherein the periodic communication is daily during a monitoring duration.

EC512) The system of EC508, wherein the server is configured to store the data determined and/or computed by the computation unit.

EC513) The system of EC512, wherein the server is configured to retrieve the stored data determined and/or computed by the computation unit for analysis.

EC514) The system of EC513, wherein the analysis comprises trend analysis.

EC515) The system of EC514, wherein the trend analysis is over a duration of three or more days.

EC516) The system of EC514, wherein the trend analysis is over a duration of at least one month.

EC517) The system of EC514, wherein the trend analysis is over a duration of at least one year.

EC518) The system of EC514, wherein the trend analysis is across a population of monitored patients.

EC519) The system of EC514, wherein the trend analysis is for a single, monitored patient.

EC520) The system of any of EC500 through EC519, further comprising one or more external connections enabling connectivity to one or more devices.

EC521) The system of EC520, wherein the network connection is one of the one or more external connections.

EC522) The system of EC520, wherein at least one of the one or more external connections is a wireless connection.

EC523) The system of EC522, wherein all of the one or more external connections are wireless connections.

EC524) The system of EC522, wherein the at least one of the one or more external connections is an 802.11 connection.

EC525) The system of EC522, wherein the at least one of the one or more external connections is a cellular connection.

EC526) The system of EC525, wherein the cellular connection is a 5G connection.

EC527) The system of EC520, wherein at least one of the one or more external connections is a wired connection.

EC528) The system of EC527, wherein all of the one or more external connections are wired connections.

EC529) The system of EC527, wherein the at least one of the one or more external connections is a USB connection.

EC530) The system of EC527, wherein the at least one of the one or more external connections is an Ethernet connection.

EC531) The system of EC520, wherein the one or more devices comprise a blood pressure monitoring device.

EC532) The system of EC520, wherein the one or more devices comprise a pulse oximeter device.

EC533) The system of EC520, wherein the one or more devices comprise a weight scale.

EC534) The system of EC520, wherein the one or more devices comprise a nebulizer device having respiratory monitoring capability.

EC535) The system of EC520, wherein the one or more devices comprise a wearable device.

EC536) The system of EC520, wherein the one or more devices are enabled to communicate with the server via the network connection.

EC537) The system of EC536, wherein the computation unit is configured to enable the one or more devices to communicate with the server via the network connection.

EC538) The system of EC536, wherein data provided from the one or more devices is configured to be communicated to the server.

EC539) The system of EC537, wherein the server is configured to store the data provided from the one or more devices.

EC540) The system of EC536, wherein the server is enabled to control at least one of the one or more devices.

EC541) The system of EC520, wherein the computation unit is enabled to control at least one of the one or more devices.

EC550) A method of monitoring one or more physiological parameters of a human body with high compliance, the method comprising: generating, with an electric field generator, an electric field; radiating the electric field through an antenna, the antenna attached to a piece of furniture and not in contact with a human body; measuring a frequency of the electric field as it interacts with the human body in the reactive near-field region of the electric field; determining respective periodic behaviors in the measured frequency corresponding to movements of one or more internal organs of the human body; and computing respective rates of movement of the one or more internal organs based on the determined respective periodic behaviors in the measured frequency.

EC551) The method of EC550, wherein the piece of furniture is a bed.

EC552) The method of EC551, wherein the antenna is between a mattress of the bed and a sheet on the bed.

EC553) The method of EC551, wherein the antenna is embedded in a mattress of the bed.

EC554) The method of EC550, wherein the piece of furniture is a chair.

EC555) The method of EC550, wherein the piece of furniture is a seat of a car.

EC556) The method of EC550, wherein the antenna is an electrically-short antenna.

EC557) The method of EC556, wherein an electrical length of the antenna is at least six inches.

EC558) The method of EC556, wherein the antenna is a dipole antenna.

EC559) The method of EC550, wherein each of the respective periodic behaviors in the measured frequency is a superposition of respective multiple sources due to interactions of the one or more internal organs with other components of the human body.

EC560) The method of EC550, wherein the electric field generator comprises a differential oscillator.

EC561) The method of EC560, wherein the differential oscillator is an inductor-capacitor tank oscillator.

EC562) The method of EC550, wherein the measuring is via a differential frequency demodulator.

EC563) The method of EC550, wherein the respective rates of the movement of the one or more internal organs comprise a heart rate and a respiration rate.

EC564) The method of EC563, wherein the human body is on a bed; wherein the antenna is underneath at least a covering of the bed; and wherein the heart rate is a nighttime resting heart rate and the respiration rate is a nighttime resting respiration rate.

EC565) The method of EC564, further comprising not using one or more portions of the measured frequency in the determining the respective periodic behaviors in the measured frequency, the one or more portions of the measured frequency corresponding to respective periods of time in which the measured frequency is not indicative of nighttime resting behavior of the human body.

EC566) The method of EC565, wherein one of the respective periods of time is due to excessive movement of the human body.

EC567) The method of EC565, wherein one of the respective periods of time is due to the electric field interacting with a second body other than the human body.

EC568) The method of EC550, further comprising attaching the antenna to the piece of furniture; and wherein no further human interaction, subsequent to the attaching, is required to enable the computing to occur over a succession of days.

EC569) The method of EC550, wherein a sensor strap comprises the antenna.

EC570) The method of EC569, further comprising securing the sensor strap to the piece of furniture, thereby attaching the antenna to the piece of furniture.

EC600) A method of monitoring one or more physiological parameters of a human body with high compliance, the method comprising: attaching, to a piece of furniture, an antenna; measuring a frequency of an electric field radiated by the antenna as it interacts with a human body in the reactive near-field region of the electric field; computing one or more parameters of the human body based at least in part on the measuring; monitoring the one or more parameters of the human body over a succession of days; and wherein no further human interaction, subsequent to the attaching, is required to enable the monitoring.

EC601) The method of EC600, further comprising determining respective periodic behaviors in the measured frequency corresponding to movements of one or more internal organs of the human body; and wherein the computing is according to the determining.

EC602) The method of EC601, wherein each of the respective periodic behaviors in the measured frequency is a superposition of respective multiple sources due to interactions of the one or more internal organs with other components of the human body.

EC603) The method of EC600, wherein the succession of days is at least 16 days in a month.

EC604) The method of EC600, wherein the succession of days is at least 80% of any consecutive span of five or more days.

EC605) The method of EC600, wherein the succession of days is at least 90% of any consecutive span of ten or more days.

EC606) The method of EC550, further comprising generating the electric field with a differential oscillator.

EC607) The method of EC600, wherein the measuring is via a differential frequency demodulator.

EC608) The method of EC600, wherein the one or more parameters of the human body comprise a heart rate and a respiration rate.

EC609) The method of EC608, wherein the heart rate is a nighttime resting heart rate and the respiration rate is a nighttime resting respiration rate.

EC610) The method of EC600, wherein the piece of furniture is a bed.

EC611) The method of EC610, wherein the attaching comprises placing the antenna between a mattress of the bed and a sheet covering the bed.

EC612) The method of EC610, wherein the attaching comprises building the antenna into a mattress of the bed.

EC613) The method of EC600, wherein a sensor strap comprises the antenna.

EC614) The method of EC613, wherein the attaching the antenna to the piece of furniture comprises securing the sensor strap to the piece of furniture.

EC700) A method of predicting a condition of a human body, comprising: generating, with an electric field generator, an electric field at a nominal frequency; measuring, at multiple time points during a measuring period, one or more properties of the electric field, the one or more properties of the electric field changing over time due to interactions with a human body subject to the electric field; determining, from the measured one or more properties, one or more periodic behaviors and one or more non-periodic behaviors; computing, from at least one of the one or more periodic behaviors and at least one of the one or more non-periodic behaviors, one or more physiological parameters of the human body; and detecting, from the one or more physiological parameters, one or more symptoms of a condition of the human body.

EC701) The method of EC700, wherein the measuring the one or more properties of the electric field measures the one or more properties of the electric field generator as the one or more properties change due to the interactions with the human body.

EC702) The method of EC700, wherein the measuring the one or more properties of the electric field measures changes in the one or more properties of the electric field generator as the one or more properties change due to the interactions with the human body.

EC703) The method of EC700, wherein the one or more properties comprise one or more of a phase, a frequency, and an amplitude.

EC704) The method of EC700, wherein the one or more periodic behaviors comprise respiration of the human body.

EC705) The method of EC700, wherein the one or more periodic behaviors comprise a heartbeat of the human body.

EC706) The method of EC700, wherein the one or more non-periodic behaviors comprise apnea.

EC707) The method of EC700, wherein the one or more non-periodic behaviors comprise coughing.

EC708) The method of EC700, wherein the one or more non-periodic behaviors comprise movement of the human body.

EC709) The method of EC700, wherein the determining the one or more non-periodic behaviors comprises determining when the human body is not interacting with the electric field sufficiently to enable the determining of at least one of the one or more periodic behaviors.

EC710) The method of EC700, wherein the determining the one or more periodic behaviors comprises not determining the one or more periodic behaviors during at least one of the one or more non-periodic behaviors.

EC711) The method of EC700, wherein the one or more physiological parameters comprise a frequency of coughing.

EC712) The method of EC700, wherein the one or more physiological parameters comprise a frequency of movement at night.

EC713) The method of EC700, wherein the one or more physiological parameters comprise a nighttime resting volume of respiration.

EC714) The method of EC700, wherein the one or more physiological parameters comprise a nighttime resting heart rate.

EC715) The method of EC700, wherein the one or more physiological parameters comprise a nighttime resting respiration rate.

EC716) The method of EC700, wherein the one or more physiological parameters comprise a respiration waveform.

EC717) The method of EC700, wherein the one or more symptoms of the condition comprise a frequency of coughing increasing over a period of days.

EC718) The method of EC700, wherein the one or more symptoms of the condition comprise nighttime restlessness increasing over a period of days.

EC719) The method of EC700, wherein the one or more symptoms of the condition comprise a nighttime resting volume of respiration decreasing over a period of days.

EC720) The method of EC700, wherein the one or more symptoms of the condition comprise heart rate variability changing over a period of days.

EC721) The method of EC700, further comprising: from the one or more symptoms of the condition, predicting the condition of the human body.

EC722) The method of EC721, wherein the condition is onset of a Chronic Obstructive Pulmonary Disease (COPD) exacerbation.

EC723) The method of EC721, wherein the condition is worsening of Congestive Heart Failure (CHF) symptoms.

EC724) The method of EC721, wherein the condition is sleep apnea.

EC750) A method comprising: using a non-contact, nighttime monitoring device and over a succession of days, computing a nighttime resting heart rate, a nighttime resting respiration rate, and one or more other physiological parameters of a human body; detecting a change over the succession of days in the nighttime resting heart rate or the nighttime resting respiration rate and in at least one of the one or more other physiological parameters of the human body; and based on the detected changes, predicting a condition of the human body.

EC751) The method of EC750, wherein the condition of the human body is onset of a disease.

EC752) The method of EC751, where the onset of the disease is the onset of a Chronic Obstructive Pulmonary Disease (COPD) exacerbation.

EC753) The method of EC751, where the onset of the disease is the onset of Congestive Heart Failure (CHF).

EC754) The method of EC750, further comprising: based on the detected changes, detecting one or more symptoms of the condition of the human body; and wherein the predicting the condition of the human body is based on the one or more symptoms.

EC755) The method of EC754, wherein the one or more symptoms of the disease comprise one or more symptoms of a Chronic Obstructive Pulmonary Disease (COPD) exacerbation.

EC756) The method of EC755, wherein the one or more symptoms of the COPD exacerbation comprise an increase in nighttime resting heart rate.

EC757) The method of EC756, wherein the increase in nighttime resting heart rate is an increase of at least two standard deviations.

EC758) The method of EC755, wherein the one or more symptoms of the COPD exacerbation comprise a change in a respiratory waveform.

EC759) The method of EC758, wherein the change in the respiratory waveform comprises faster inhalation.

EC760) The method of EC758, wherein the change in the respiratory waveform comprises slower exhalation.

EC761) The method of EC758, wherein the change in the respiratory waveform comprises decreased volume of respiration.

EC762) The method of EC758, wherein the change in the respiratory waveform comprises decreased amplitude of the respiratory waveform.

EC763) The method of EC755, wherein the one or more symptoms of the COPD exacerbation comprise a change in nighttime resting respiration rate.

EC764) The method of EC755, wherein the one or more symptoms of the COPD exacerbation comprise a change in an amount of REM sleep.

EC765) The method of EC754, wherein the one or more symptoms of the disease comprise one or more symptoms of Congestive Heart Failure (CHF).

EC766) The method of EC765, wherein the one or more symptoms of Congestive Heart Failure (CHF) comprise shortness of breath.

EC767) The method of EC765, wherein the one or more symptoms of Congestive Heart Failure (CHF) comprise edema.

EC800) A system comprising: an antenna; a detector; an electric field generator connected to the antenna and to the detector and configured to generate an electric field at a nominal frequency; a computation unit; wherein the antenna is configured to radiate the electric field; wherein the detector is configured to measure a frequency generated by the electric field generator as the frequency changes due to interactions with a body in the reactive near-field region of the electric field; wherein the computation unit is configured to (a) determine respective periodic behaviors in the measured frequency indicative of movement of one or more internal components of the body, and (b) compute a respective parameter of each of the one or more internal components of the body according to the respective periodic behaviors in the measured frequency.

EC801) The system of EC800, wherein the electric field generator is connected between the antenna and the detector.

EC802) The system of EC800, wherein the detector is configured to measure the frequency generated by the electric field generator by comparing the frequency generated by the electric field generator with a phase shift of the frequency generated by the electric field generator.

EC803) The system of EC802, wherein the phase shift is a 90 degree phase shift at the nominal frequency.

EC804) The system of any of EC800 through EC803, wherein the nominal frequency is between 10 MHz and 100 MHz.

EC805) The system of EC804, wherein the nominal frequency is 28 MHz.

EC806) The system of any of EC800 through EC803, wherein the antenna is a two-wire antenna.

EC807) The system of any of EC800 through EC803, wherein the electric field generator comprises a differential oscillator.

EC808) The system of EC807, wherein the differential oscillator is a differential tank oscillator.

EC809) The system of any of EC800 through EC803, wherein the detector comprises a quadrature demodulator.

EC810) The system of EC808, wherein the quadrature demodulator is a differential quadrature demodulator.

EC811) The system of any of EC800 through EC801, wherein the detector comprises a sample-and-hold circuit and an analog-to-digital converter.

EC812) The system of EC811, wherein the sample-and-hold circuit is a differential sample-and-hold circuit.

EC813) The system of any of EC800 through EC801, wherein the detector comprises a wideband analog-to-digital converter.

EC900) A sensor strap system for attaching a sensor to a bed, comprising: a strap comprising a sensor capable of detecting physical or physiological activities or conditions of a target subject; two brackets positioned under a mattress of a bed on opposite sides of the bed; and wherein the strap is placed on a top surface of a bed and extends over the opposite sides of the bed where it is affixed to each of the two brackets.

EC901) The sensor strap system of EC900, wherein each of the two brackets is an L-shaped bracket that is positioned at least partially under the mattress and at least partially up a respective side of the mattress where each L-shaped bracket is affixed to a respective side of the strap.

EC902) The sensor strap system of EC900, wherein the strap is arranged orthogonal to a direction in which a sleeping body is expected to occupy the bed.

EC903) The sensor strap system of EC902, wherein the strap is arranged so that the sensor is positioned in an expected position between the shoulders and hips of a torso of the sleeping body.

EC904) The sensor strap system of EC900, wherein the sensor is a near-field-coupling-optimized antenna.

Further Examples

What follows are further examples of a system comprising a BPCD. Such examples relate generally to the technical field of monitoring systems, and more particularly, to a monitoring system that detects physical changes without physical contact.

Additional Background

The performance of a variety of monitoring systems may be affected by where a sensor or its parts are placed relative to a target (e.g., a human such as an adult, teen, child, or baby) that is being monitored. For example, certain monitoring systems may require a sensor to be in physical contact with a target and may further require a part (e.g., a power or data cable) to be connected from a sensor to a monitoring device. There may be other circumstances in which the sensor might be used to detect changes in occupancy of a vehicle seat. In this case the sensor might also sense vital signs—e.g., pulse and/or respiration—of a seat occupant without direct physical contact.

Known monitoring systems require a sensor to be directly in contact with a target. For example, a traditional electrocardiogram (ECG) uses external electrodes to detect a patient's ECG signal. The external electrodes are located on the ends of cables and must be physically placed on a patient and near the patient's heart. This often necessitates the use of conductive materials that may be inconvenient to hook up and use, especially for long-term monitoring of a relatively active patient. These devices have significant limitations. For example, the patient must be physically connected to the device. If the patient wants to leave his or her bed, the device needs to be detached from, and then re-attached to the patient on his/her return, often by a highly trained staff member. The inconvenience and the delays associated with setting up such monitoring systems are also not well-suited for monitoring more active targets, for example, a baby in a crib or a person driving a vehicle. Although there are monitoring systems incorporated into devices such as wristbands and armbands they still typically need to be directly in contact with the target, and often provide inaccurate information and limited functionality.

Accordingly, there is a need for a monitoring system that does not require a sensor to be directly in contact with a target. There is also a need for a monitoring system that can assist in the management of a target's health, fitness, sleep and diet by monitoring physiological changes in a person's body. There is further a need for a monitoring system suitable for long-term use that can sense changes in a target and provide timely and appropriate diagnostic, prognostic and prescriptive information.

Summary of Further Examples

Embodiments include systems and methods that allow detection of physical changes within a body without physical contact with, or attachment to, the body. A body is a mass of matter distinct from other masses. Non-limiting examples of a body include, for example, a human's body, an animal's body, a container, a car, a house, etc. These changes might be physiological events such as cardiac function in an animal or changes in the properties of a bulk material such as grain in a silo. These changes could be dimensional changes such as those caused by the function of organs in an animal, or changes in the composition of the material such as water content in lumber.

A key feature of the measurement technique used in this instrument is that the measurement may be done over an extended volume such that the changes of multiple phenomena may be observed simultaneously. For example, sensing two separate but related physiological parameters (e.g., pulse and respiration) may be accomplished concurrently. The region sensed by this instrument may be changed by sensor element design within the instrument. A further extension of bulk sensing capability is the opportunity to use sophisticated computer signature recognition software, such as wavelet-based approaches, to separate individual features from the composite waveform.

This application relates to U.S. Pat. No. 9,549,682, filed on Oct. 30, 2014, which is explicitly incorporated by reference herein in its entirety. This application also relates to U.S. Pat. No. 9,035,778, filed on Mar. 15, 2013, which is explicitly incorporated by reference herein in its entirety.

Disclosed subject matter includes, in one aspect, a system for detecting and analyzing changes in a body. The system includes an electric field generator configured to produce an electric field. The system includes an external sensor device, coupled to the electric field generator, configured to detect physical changes in the electric field, where the physical changes affect amplitude and frequency of the electric field. The system includes a quadrature demodulator, coupled to the electric field generator, configured to detect changes of the frequency of the output of the electric field generator and produce a detected response that includes a low frequency component and a high frequency component. The system includes a low pass filter, coupled to the quadrature demodulator, configured to filter out the high frequency component of the detected response to generate a filtered response. The system includes an amplitude reference source configured to provide an amplitude reference. The system includes an amplitude comparison switch, coupled to the amplitude reference source and the electric field generator, configured to compare the amplitude reference and the amplitude of the electric field to generate an amplitude comparison. The system includes a signal processor, coupled to the low pass filter and the amplitude comparison switch, configured to analyze the filtered response and the amplitude comparison response.

Disclosed subject matter includes, in another aspect, a method for detecting and analyzing changes in a body. The method includes establishing an electric field around a desired area of detection with an electric field generator. The method includes monitoring frequency of the electrical field with a quadrature demodulator. The method includes detecting changes in the frequency of the electric field with the quadrature demodulator. The method includes monitoring amplitude of the electric field. The method includes detecting changes in the amplitude of the electric field with an amplitude reference source.

Disclosed subject matter includes, in yet another aspect, a non-transitory computer readable medium having executable instructions operable to cause an apparatus to establish an electric field around a desired area of detection with an electric field generator. The instructions are further operable to cause the apparatus to monitor frequency of the electrical field with a quadrature demodulator. The instructions are further operable to cause the apparatus to detect changes in the frequency of the electric field with the quadrature demodulator. The instructions are further operable to cause the apparatus to monitor amplitude of the electric field. The instructions are further operable to cause the apparatus to detect changes in the amplitude of the electric field with an amplitude reference source.

Disclosed subject matter further includes, in yet another aspect, a system for detecting and analyzing changes in a body. The system includes an electric field generator, an external sensor device, a quadrature demodulator, and a controller. The electric field generator is configured to generate an electric field that associates with a body. The external sensor device sends information to the electric field generator and is configured to detect a physical change in the body in the electric field, where the physical change causes a frequency change of the electric field. The quadrature demodulator receives the electric field from the electric field generator and is configured to detect the frequency change of the electric field generated by the electric field generator and to produce a detected response. The controller is coupled to the electric field generator and is configured to output a frequency control signal to the electric field generator and to modify the frequency of the electric field by adjusting the frequency control signal.

Disclosed subject matter includes, in yet another aspect, a method for detecting and analyzing changes in a body. The method includes generating an electric field that associates a body with an electric field generator. The method includes detecting a physical change in the body in the electric field with an external sensor device, where the physical change causes a frequency change of the electric field. The method includes monitoring and detecting changes in the frequency of the electric field and producing a detected response with a quadrature demodulator. The method includes receiving, by a controller, the detected response. The method includes outputting a frequency control signal to modify the frequency of the electric field associated with the body. The method includes modifying, by the electric field generator, the electric field associated with the body based on the frequency control signal.

Disclosed subject matter includes, in yet another aspect, a non-transitory computer readable medium having executable instructions operable to cause an apparatus to detect and analyze a change in a body. The instructions are further operable to cause the apparatus to generate an electric field that associates with a body. The instructions are further operable to cause the apparatus to detect a physical change in the body in the electric field, where the physical change causes a frequency change of the electric field. The instructions are further operable to cause the apparatus to monitor and detect changes in the frequency of the electric field and produce a detected response. The instructions are further operable to cause the apparatus to receive the detected response. The instructions are further operable to cause the apparatus to output a frequency control signal to modify the frequency of the electric field associated with the body. The instructions are further operable to cause the apparatus to modify the electric field associated with the body based on the frequency control signal.

Before explaining example embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

These and other capabilities of embodiments of the disclosed subject matter will be more fully understood after a review of the following figures, detailed description, and claims.

It is to be understood that both the foregoing general description and the following detailed description are explanatory only and are not restrictive of the claimed subject matter.

Detailed Description of Further Examples

The manner in which materials behave in an alternating current ("AC") circuit usually is described in terms of the amount of energy stored in the material and the amount of energy dissipated in the material on a per cycle basis. Energy storage occurs in both electric and magnetic fields created by the current. Dissipation occurs in transformation, in the material, of electrical energy into thermal energy, i.e., heat. These properties can vary over a wide range depending on the material. In many materials the properties are predominantly one type.

Dissipation in some materials may be attributed to the magnetic field properties of a material and in other cases to the electric field properties. In more general cases, both of these mechanisms are present. Because of this, there is a convention in which the magnetic field storage properties and any related dissipation are combined in a vector sum and called permeability. Similarly, the vector sum of the electric field storage properties and associated dissipation is called permittivity. These vector sums are expressed as complex values in which the dissipation is the real component and field storage properties are the imaginary component. In the present disclosure, the aggregated change in properties of a body are detected and quantified by measuring changes in the body's electromagnetic properties.

Although the approach described here works by sensing changes in the electromagnetic properties, i.e. changes in both electric and magnetic properties, in some applications the significant changes occur in only one set of properties. For purposes of further discussion, the instrument in embodiments described herein detects changes in permittivity. Detection of any other suitable property or combination of properties that are appreciated by a person skilled in the art is also within the spirit and limit of the disclosed subject matter. The dissipative component of permittivity often is expressed as the loss tangent of the material, while the storage term is called capacitance. Measuring these properties is accomplished by sensing the change of phase and amplitude of an electric field generated by the instrument and caused by the aggregated properties of a body within the field.

FIG. 1 illustrates a system 100 for detecting and analyzing changes in a body according to certain embodiments of the present disclosure. The system 100 includes an external sensor device 102, an electric field generator 104, an amplitude reference source 106, a quadrature demodulator 108, an amplitude comparison switch 110, a low pass filter 114, a signal processor 116, and a display 118. The components included in the system 100 can be further broken down into more than one component and/or combined together in any suitable arrangement. Further, one or more components can be rearranged, changed, added, and/or removed. In some embodiments, one or more components of the system 100 can be made by an application specific integrated circuit (ASIC).

The electric field generator 104 creates an electric field that illuminates the desired area of detection. The frequency and amplitude of this electric field is determined by the characteristics of the body being observed. In some embodiments, a frequency-determining component of the electric field generator 104—a resonant circuit than can comprised of a combination of inductive, capacitive, and resistive elements—is connected to an external device that creates the electric field providing the desired coverage of the body of material being studied. In some embodiments, the electric field generator 104 can be an oscillator, such as an inductor-capacitor (LC) tank oscillator.

The external sensor device 102 may be made from a wide variety of materials; the only requirement of these materials is that they are electrical conductors. The external sensor device 102 can be constructed in many different mechanical configurations to provide appropriate coverage of the desired region. For example, in some embodiments, the external sensor device 102 can be a plurality of metallic plates. In some embodiments, the shape and/or the orientation of the external sensor device 102 can be changed as needed.

In some embodiments, the external sensor device 102 is not required to physically contact the body being studied. For example, the external sensor device 102 and the supporting electronics could be installed in the driver's seat of an over-the-highway truck to detect changes in physiological indicators of driver drowsiness and thus take actions to prevent an accident. In some embodiments, the sensing process usually is done separately in two paths: (1) in a first path the changes in the real component of the vector sum, e.g., energy dissipation, are detected; (2) in a second path the changes related to the imaginary component—a component such as a capacitance or inductance in which the phase of the current flowing in them is orthogonal to the current in the real component—are separately processed. In some embodiments, the changes in amplitude of the electric field are detected in the first path, and the changes in frequency of the electric field are detected in the second path. Generally, as known by a person skilled in the art, the changes in phase of the electric field can be obtained by analyzing the changes in frequency of the electric field. These two signals can be combined in later signal processing to re-create the changes in the complex permittivity or kept as individual signals for separate analysis. These two paths are discussed separately below.

To detect changes in the imaginary component of the complex permittivity, the output of the electric field generator 104 is connected to the quadrature demodulator 108. The quadrature demodulator 108 detects the changes of the frequency of the output of the electric field generator 104 and produce a detected response that includes a low frequency component and a high frequency component. FIG. 6 illustrates a quadrature demodulator 108 according to certain embodiments of the present disclosure. The quadrature demodulator 108 includes a mixer 602 and a resonant circuit 604. In the present disclosure, a double balanced mixer is described, but other suitable types of mixers can also be used. The components included in the quadrature demodulator 108 can be further broken down into more than one component and/or combined together in any suitable arrangement. Further, one or more components can be rearranged, changed, added, and/or removed.

An input signal to the quadrature demodulator 108 is split into two paths. One path is connected to one input port of the double balanced mixer 602, and the other path is connected to the resonant circuit 604. The output of the resonant circuit 604 is connected to the other input port of the double balanced mixer 602. In some embodiments, the resonant circuit 604 includes an inductor and a capacitor. In some embodiments, the resonant circuit 604 includes an inductor, a capacitor, and a resistor. The circuit components of the resonant circuit 604 can be connected in series, in parallel, or any other suitable configuration. The resonant circuit 604 can also be implemented by other circuit configurations that are appreciated by a person skilled in the art. In some embodiments, the resonant circuit 604 is tuned to the nominal center frequency of the electric field generator 104.

The double balanced mixer 602 multiplies the two signals together (one signal from the input and the other signal from the resonant circuit 604). The product of the two signals creates two components in the output: one proportional to the difference between the two input frequencies and another at the sum of the two input frequencies. When there is an exact 90-degree phase difference between the two signals, the demodulator output is zero. When the phase difference is less than about +/−90 degrees there will be a DC component in the output of the double balanced mixer 602.

The output signal from the quadrature demodulator 108 is fed to a low pass filter 114. The low pass filter 114 is typically an analog circuit that includes resistive, inductive and/or capacitive elements that separates the low frequency component of the quadrature demodulator 108 from the much higher frequency component generated by the quadrature demodulator 108. The cutoff frequency of the low pass filter is selected to provide low attenuation of the desired signal components while sufficiently suppressing the high frequency terms. After filtering, the signal is connected to the signal processor unit 116 described below.

Detecting changes in electric field dissipation is processed somewhat different from detecting frequency changes in electric field. In FIGS. 1 and 6, the output of the electric field generator 104 is multiplied by a phase-shifted version of itself produced by the resonant circuit 604. Unlike phase/frequency change detection, amplitude variations must be compared with the electric field generator 104 output unchanged by the material being studied. Referring again to FIG. 1, an amplitude reference signal is created by measuring the output of the electric field generator 104 in the absence of any external influence and used to set the output level of the amplitude reference source 106.

The amplitude reference source 106 is typically a time and temperature stable voltage reference that can be provided by a semiconductor component such as a diode. The output of the amplitude reference source 106 is fed to one input of the amplitude comparison switch 110. The switch 110, controlled by the signal processor 116, alternately connects the amplitude reference source 106 and electric field generator output 104 to the signal processor 116. By measuring the difference between the reference signal 106 and the electric field generator 104 output—and with sufficient calibration information—the amount of power absorbed, e.g., dissipated, by the material under study may be computed.

The amplitude comparison switch 110 functions by sampling the output of the electric field generator 104 at a rate at least twice as fast as the most rapid variation of the amplitude of the electric field generator 104 and subtracting the value of the amplitude reference source 106. The output of the amplitude comparison switch 110 is thus equal to the difference between the amplitude of the electric field generator 104 and the amplitude of the amplitude reference source 106.

The signal processor 116 takes the output of the low pass filter 114 and extracts the desired components into desired formats for further use or processing. The signal processor 116 also takes the output of the amplitude comparison switch 110 to analyze the changes in amplitude of the electric field. The signal processor 116 can be implemented by use of either analog, digital, or combined circuits.

FIG. 7 illustrates a signal processor 116 according to certain embodiments of the present disclosure. The signal processor 116 includes a sample-and-hold circuit 702, an analog-to-digital converter (ADC) 704, a digital signal processor 706, and a microcontroller 708. The components included in the signal processor 116 can be further broken down into more than one component and/or combined together in any suitable arrangement. Further, one or more components can be rearranged, changed, added, and/or removed.

The sample-and-hold circuit 702 is configured to sample a continuous-time continuous-value signal and hold the value for a specified period of time. A typical sample-andhold circuit 702 includes a capacitor, one or more switches, and one or more operational amplifiers. In some embodiments, other suitable circuit implementations can also be used.

The ADC 704 receives the output of the sample-and-hold circuit 702 and converts it into digital signals. In some embodiments, the ADC 410 can have a high resolution. Since the changes in bulk permittivity of the entire region within the electric field in many possible applications are expected to be relatively slow, e.g., less than a few hundred Hertz, in some embodiments it can be sufficient to undersample the output of the electric field generator 404 by using the sample-and-hold device 406 to make short samples that can be processed with the ADC 704 with a sample rate in the five thousand samples/sec range. An ADC with 24-bit resolution or 32-bit resolution are readily available. In some embodiments, the ADC 704 can have other suitable resolutions.

The digital signal processor 706 can be configured to process the output of the ADC 704. In some embodiments, the digital signal processor 706 can be a microprocessor.

The microcontroller 708 can be coupled to one or more components of the signal processor 116. In some embodiments, the microcontroller 708 can control the sampling rate and/or clock rate of the one or more components of the signal processor 116. In some embodiments, the microcontroller 708 can issue command signals to the one or more components of the signal processor 116. In some embodiments, the microcontroller 708 can be a generic high performance low power system on chip (SOC) product. For example, the microcontroller 708 can be an ARM based processor, such as an ARM Cortex-M4 core processor or any other suitable models.

Referring to the display 118, the display 118 can be configured to display various results generated by the signal processor 116. The display 118 can be a touch screen, an LCD screen, and/or any other suitable display screen or combination of display screens. In some embodiments, the output of the signal processor 116 can also be fed to a data logger for signal storage and/or processing.

FIG. 2 shows a generalized version of the transfer function of a quadrature demodulator 108 showing the typical relationship between the voltage output and frequency of the input signal from the electric field generator 104. The horizontal axis shows frequency of the input signal in Hertz (Hz), and the vertical axis shows demodulator output in Volts (V). The center of the horizontal axis 210 indicates the nominal resonant frequency of the resonant circuit 604. For example, if the nominal resonant frequency of the resonant circuit 604 is 80 MHz, then the center of the horizontal axis 210 is at 80 MHz. The slope of the central region 202 of the curve can be made quite linear to allow operation over an extended frequency range while offering the same sensitivity in terms of output voltage as function of phase/frequency change. The transfer function is mathematically dependent only on the frequency/phase relationship between the two inputs to the double-balanced mixer 108. This permits a wide and dynamic range in detection in the phase/frequency changes induced by material properties separate from changes in amplitude due to dissipative properties.

FIG. 2 illustrates the sensor operating as it might be employed in two different applications while using the same electric field generator 104 and the quadrature demodulator 108. In Region 1 204, the DC component—dependent on the exact value of the frequency and slope of the transfer function—might be, for example, −1.5 volts. If there are small variations in the frequency of the electric field generator 104, there will also be small variations in the quadrature demodulator output voltage. For the example here the output variations will be centered about −1.5 volts. In Region 2 206, the DC term might be, for example, around +1.0 volts. However, since the slope of the transfer function is very close to being the same in both regions, the small variations will be centered around 0 volts.

This is an important benefit to the approach taken here. If there are a wide variety of materials, each with varying electromagnetic properties within the electric field, the aggregated output of the quadrature demodulator 108 can have a mean DC level determined by the contributions of all materials within the electric field region, while still maintaining an essentially constant transfer function for small changes in material properties. The small-signal linearity allows signal components from separate constituents of the material being studied to be linearly combined. Linear combination of the various contributions in the output waveform can be readily separated in later signal processing. An example of a combined waveform showing both respiration and heart rate (pulse) signals is shown in FIG. 3.

Figure 3:
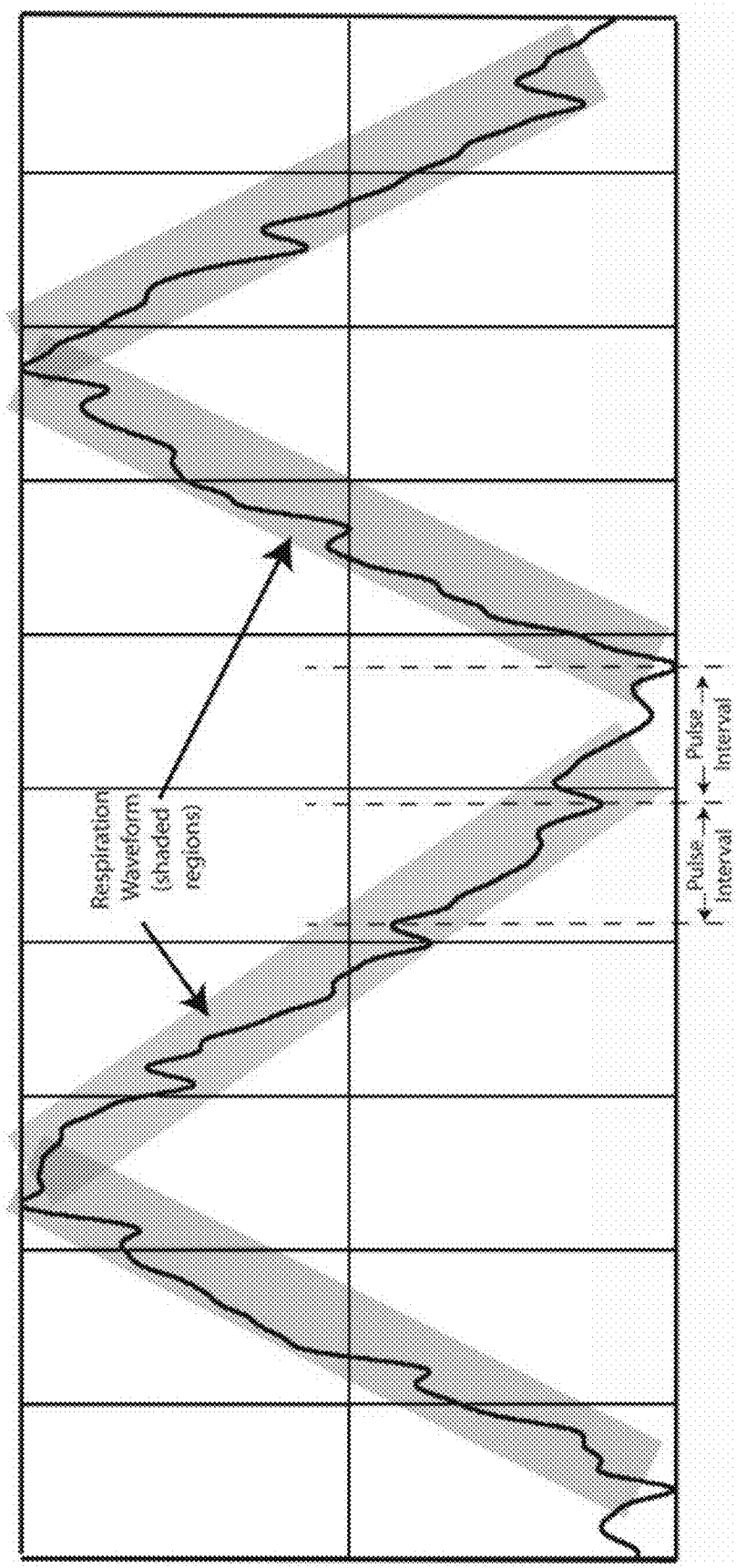
FIG. 3 illustrates an example of a waveform combining both respiration and heart rate signals according to certain embodiments.

FIG. 3 shows a signal comprised of a large, low frequency, roughly triangular waveform that might be typical of respiration by a body and a signal often seen in a heart pulse of smaller amplitude, higher frequency, and more complex waveform. In FIG. 3 the linear addition of these two waveforms is shown as the smaller amplitude, higher frequency, more complex heart pulse "riding" on the larger, slower triangular respiration component.

In addition to the largely analog design described above, a "direct-to-digital" approach is also possible. FIG. 4 illustrates a system 400 for detecting and analyzing changes in a body according to certain embodiments of the present disclosure. The system 400 includes an external sensor device 402, an electric field generator 404, a sample-and-hold device 406, a microcontroller 408, an ADC 410, a digital signal processor 416, and a display 418. The components included in the system 400 can be further broken down into more than one component and/or combined together in any suitable arrangement. Further, one or more components can be rearranged, changed, added, and/or removed. In some embodiments, the components included in FIG. 4 are similar to the corresponding components described in FIG. 1 and/or FIG. 7.

In some embodiments, the system 400 replaces most analog components described in FIG. 1 with digital or mixed-signal components. The "direct-to-digital" concept employs the ADC 410 driven by the sample-and-hold device 406. In some embodiments, the ADC 410 can have a high resolution. Since the changes in bulk permittivity of the entire region within the electric field in many possible applications are expected to be relatively slow, e.g., less than a few hundred Hertz, it can be sufficient to undersample the output of the electric field generator 404 by using the sample-and-hold device 406 to make short samples that can be processed with the ADC 410 with a sample rate in the five thousand samples/sec range. Such devices with 24-bit resolution are readily available, as are 32-bit versions at a significantly higher component price. In such a system, the signal processor 416 would take over the functions performed by the quadrature demodulator 108 described in FIG. 1. Since the features of the "direct-to-digital" instrument would be determined by the software in the signal processor 416, a single hardware set could be loaded with specialized software for different applications. The programmable characteristics of a "direct-to-digital" approach could enable economies of scale, driving down the unit cost and opening new market opportunities. In some embodiments, the ADC can be made by an application specific integrated circuit (ASIC).

Figure 5:
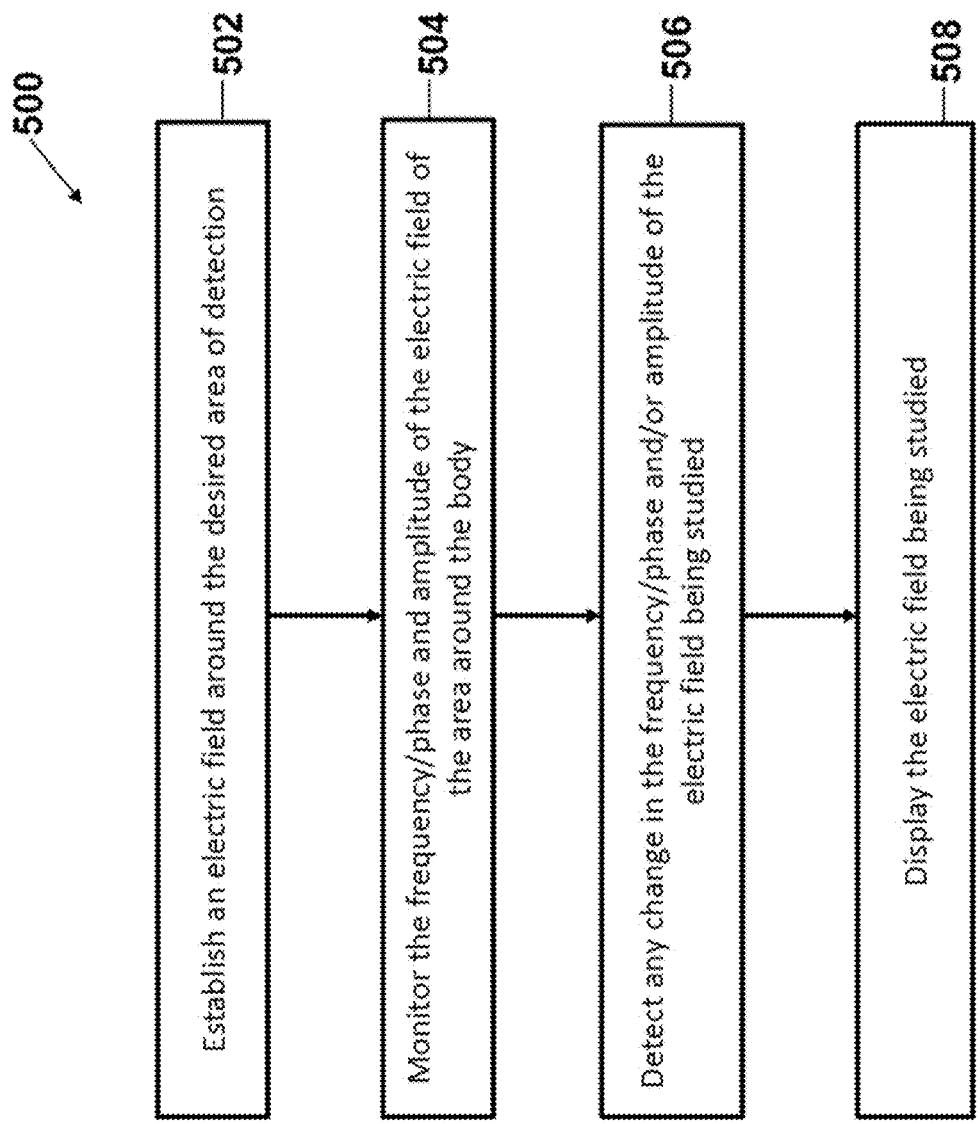
FIG. 5 illustrates an example of a process of detecting and analyzing changes in a body according to certain embodiments.

FIG. 5 is a flow chart illustrating a process 500 of detecting and analyzing changes in a body according to certain embodiments of the present disclosure. The process 500 is illustrated in connection with the system 100 shown in FIG. 1 and/or the system 400 shown in FIG. 4. In some embodiments, the process 500 can be modified by, for example, having steps rearranged, changed, added, and/or removed.

At step 502, an electric field is established around and within the desired area of detection. The desired area of detection is typically around a body that is going to be monitored. In some embodiments, the electrical field is established by using the electric field generator 104, which creates an electric field that illuminates the desired area of detection. The process 500 then proceeds to step 504.

At step 504, the frequency/phase and amplitude of the electric field of the desired area of detection are monitored. In some embodiments, the external sensor device 102 is used to monitor the area around and within the body. The external sensor device 102 is not required to physically contact the body being studied. The process 500 then proceeds to step 506.

At step 506, the electric field of the desired area of detection is processed and analyzed to detect any change. The process 500 can detect the change of the electric field in both amplitude and frequency/phase. For example, amplitude variations of the electric field can be compared with the electric field generator 104 output unchanged by the material being studied. Referring again to FIG. 1, an amplitude reference signal is created by measuring the output of the electric field generator in the absence of any external influence and used to set the output level of the amplitude reference source 106. The output of the amplitude reference source 106 is fed to one input of the amplitude comparison switch 110. The switch 110, controlled by the signal processor 116, alternately connects the amplitude reference source 106 and electric field generator output 106 to the signal processor. By measuring the difference between the reference signal and the electric field generator 104 output—and with sufficient calibration information—the amplitude comparison response of the electric field can be determined.

The change of the electric field in frequency/phase can be detected and analyzed by the quadrature demodulator configuration discussed in connection with FIG. 1 and FIG. 6. For example, in some embodiments, the output of the electric field generator 104 is connected to the quadrature demodulator that is configured to detect the changes of the frequency of the output of the electric field generator 104 and produce a detected response that includes a low frequency component and a high frequency component. The detected response is then fed to a low pass filter 114 that is configured to filter out the high frequency component of the detected response to generate a filtered response. In some embodiments, once the changes in frequency is detected, the changes in phase can be readily derived by people skilled in the art.

The filtered response and the amplitude comparison response can then be supplied to a signal processor for further analysis.

In some embodiments, the change of the electric field can be analyzed under the "direct-to-digital" approach described in the system 400 in connection with FIG. 4. The output of the electric field generator 404 can be sampled and held by the sample-and-hold device 406 and digitized by the ADC 410. The digitized output of the ADC 410 can then be analyzed by the digital signal processor 416. The process 500 then proceeds to step 508.

At step 508, the electric field can be displayed for visual inspection. In some embodiments, the changes of the electric field can also be displayed and recorded. In some embodiments, the changes of the electric field can be extracted to provide specific bodily function features such as vascular processes and conditions, respiration processes and conditions, and other body material characteristics that vary with permittivity.

In some embodiments, the system 100 or the system 400 can include a processor, which can include one or more cores and can accommodate one or more threads to run various applications and modules. The software can run on the processor capable of executing computer instructions or computer code. The processor may also be implemented in hardware using an application specific integrated circuit (ASIC), programmable logic array (PLA), field programmable gate array (FPGA), or any other integrated circuit.

The processor can be coupled with a memory device, which can be a non-transitory computer readable medium, flash memory, a magnetic disk drive, an optical drive, a PROM, a ROM, or any other memory or combination of memories.

The processor can be configured to run a module stored in the memory that is configured to cause the processor to perform various steps that are discussed in the disclosed subject matter.

In some embodiments, the electric field generator has a tuner for adjusting the signal outputting to the quadrature demodulator. In some embodiments, the tuner can be implemented in an application-specific integrated circuit (ASIC), programmable logic array (PLA), field programmable gate array (FPGA), or any other integrated circuit. In some embodiments, the tuner can be implemented as a stand-alone subunit connected within or to the electric field generator. For example, the tuner can be an integrated inductor-capacitor (LC) tank oscillator.

Referring back to FIG. 2, a typical transfer function of a quadrature demodulator 108 depicts the relationship between the voltage output and frequency of the input signal from the electric field generator 104. The horizontal axis shows the frequency of the input signal in Hertz (Hz), and the vertical axis shows the demodulator output in Volts (V). The center of the horizontal axis 210 indicates the nominal resonant frequency of a resonant circuit. The slope of the central region 202 illustrates the linear frequency range of the electric field generated by the electric field generator. It may be sometimes desirable, or even necessary, to expand the linear frequency range of slope 202 in order to allow signal components from separate constituents of a material to be linearly combined. An advantage of linearly combining the various contributions is that the output waveform can be readily separated in later signal processing for individual analysis. In contrast, a signal component not in the linear frequency range cannot be linearly combined, and thus makes it challenging to analyze its individual contribution in the output waveform.

One of the ways to expand the linear frequency range of the quadrature demodulator is by adjusting the response curve of the quadrature demodulator. Such adjustment is possible because the quadrature demodulator's output voltage is related to the change of the oscillator frequency. However, adjusting the quadrature demodulator's output could decrease the sensitivity of the system. Alternatively, since the quadrature demodulator's output is a function of the change in frequency and not the actual frequency, shifting the actual frequency itself provides another way to expand quadrature demodulator's linear frequency range without sacrificing the sensitivity. For example, FIG. 8 illustrates a system 800 for detecting and analyzing changes in a body according to certain embodiments. The system 800 is capable of adjusting the quadrature demodulator's linear frequency range by tuning the electric field generator.

Referring to FIG. 8, the system 800 includes an external sensor device 802, an electric field generator 804 with a tuner 820, an amplitude reference source 806, a controller 808 with an adjuster 818, a quadrature demodulator 810, an amplitude comparison switch 812, a low pass filter 814, and a signal processor 816 configured to output data to a display. The components included in the system 800 can be further broken down into more than one component and/or combined together in any suitable arrangement. Further, one or more components can be rearranged, changed, added, and/or removed. For example, in some embodiments, system 800 can detect and analyze physical changes in an object without the amplitude reference source 806, and amplitude comparison switch 812. In some embodiments, the system 800 establishes amplitude and/or frequency reference comparison using a specific feedback value.

In some embodiments, the electric field generator 804 is configured to generate an electric field based on the information received from the external sensor device 802 subject to adjustments made by the tuner 820. The external sensor device 802, connected to the electric field generator 804, is configured to detect physical changes in a body or an object in the electric field, and to output the sensor information to the electric field generator 804. The external sensor device 802 may be made from a wide variety of materials; the only requirement of these materials is that they are electrical conductors. To detect the imaginary component of the changes in the electric field, the output of the electric field generator 804 is connected to the quadrature demodulator 810. The quadrature demodulator 810 detects the changes of the frequency of the electric field and produces a detected response that includes a low frequency component and a high frequency component. In some embodiments, the detected response is fed to a low pass filter 814, and then send to the signal processor 816 for further analysis, similar to the process depicted in FIG. 1.

In some embodiments, the detected response from the quadrature demodulator 810 is fed to the controller 808 to establish a feedback loop for tuning the electric field generator 804. The controller 808 can include one or more hardware processors, memory components, electronic circuits, and the like. For example, the controller 808 may include an ASIC. The controller 808 can include standalone components, components integrated with other features of system 800, or a combination thereof. In some embodiments, the controller 808 includes the adjuster 818 that is coupled to the tuner 820 of the electric field generator 804 to enable the system or a user to adjust the outputting signal of the electric field generator 804.

Referring to FIG. 8, the controller 808 may output a frequency control signal, via the adjuster 818, to the tuner 820 of the electric field generator 804 based on the detected response received from the quadrature demodulator 810. For example, if the detected response shows that a signal component from a constituent of a material is outside of the linear frequency range, the controller 808 can analyze the transfer function, and output a frequency control signal to the electric field generator 804 to adjust the electric field generator 804's output signal. In some embodiments, the actual frequency of the electric field is modified via the frequency control signal. In response, the quadrature the linear frequency range of the quadrature demodulator 810 may be expanded so that all signal components are within the linear frequency range. Although the feedback loop described here is based on the detected response form the quadrature demodulator 810, responses from other components in the system 800 may also be used. For example, the feedback loop can also be established via the filtered response from the low pass filter 814, the analyzed response from the signal processor 816, or directly from the output of the electric field generator 804. In some embodiments, the feedback loop can receive signals from more than one component of the system 800.

The frequency control signal may be transmitted via any suitable communication media, including wired or wireless media. In some embodiments, the frequency control signal may include one or more analog electrical signals, digital electrical signals, electrical waveforms (e.g., pulse-width modulation waveforms), or the like.

In some embodiments, the electric field generator 804 includes components with different functions. For example, the electric field generator 804 can include an LC tank oscillator, a buffer, and a power conditioning element. In some embodiments, the LC tank oscillator is configured as a Colpitts oscillator or any other suitable oscillator; the buffer is a unity gain device that shields the LC tank oscillator from undesired interactions with the quadrature demodulator 810; and the power condition element insures a stable power value for the LC tank oscillator and the buffer. The Colpitts oscillator can be the electric field generator 804's tuner 820. In operation, the controller 808 may send a frequency control signal to adjust the values of the inductor (L) and/or capacitor (C) of the Colpitts oscillator such that the signal entering the quadrature demodulator 810 will always be within the linear limits of the quadrature demodulator 810's linear frequency range. Different types of variable inductor or capacitor may be used in the Colpitts oscillator. In some embodiments, the values of the L and C can be adjusted by combining the fixed values of L and of C with one or more of electrically sensitive inductive and/or capacitive components. Hence, by altering the electricity flowing through at least one of the electrically sensitive inductive or capacitive components, the controller 808 can effectively change the values of L or C, and thus modify the signal entering the quadrature demodulator 810. In some embodiments, the flow of electricity is controlled by manually adjusting an electric source. In some embodiments, the flow of electricity can be automatically controlled by a voltage circuit.

FIG. 9 illustrates a Colpitts oscillator 900 according to certain embodiments. The Colpitts oscillator 900 includes two main components: an amplifier 904 and a resonant tank circuit 906. Colpitts oscillators are known for their ability to output signals with a fixed frequency. According to certain embodiments, the Colpitts oscillator 900 is initialized when a small input, usually random noise, that is received by the amplifier 904. The amplifier 904 increases the magnitude of the initial small input and sends an amplified signal to the resonant tank circuit 906 which includes an inductive element 908 and a capacitive element 910. The input and output of the resonant tank circuit 910 are configured to only allow signals to pass through with a single frequency. Hence, the amplified signal can only enter and exit the resonant tank circuit 906 with a single frequency. The output of the resonant tank circuit 906 is then fed back to the input of the amplifier 904 to via feedback loop. In operation, the feedback process would continue so long as the amplifier has sufficient gain to overcome any losses in the resonant tank circuit 906. The feedback process enables the Colpitts oscillator to reliability output signals with a fixed frequency.

According to certain embodiments, the electric field generator 804 with Colpitts oscillator as its tuner can be tuned by a frequency control signal from the controller 808. Specifically, the frequency of oscillation, measured in Hertz, is defined by where $1/\sqrt{LC}$ is the inductive component measured in Henries and C is the capacitive component measured in Farads. Referring to FIG. 9, to tune the electric field generator 804, the frequency control signal would adjust the value of the inductive 908 and capacitive component 910 in the resonant tank circuit 906. In some embodiments, the inductive and capacitive components can be combined with multiple constituents. For example, the inductive component 908 may be a single device of fixed inductance while the capacitive component 910 might be implemented as two separate devices—one with a fixed value and the other a variable capacitor. As another example, the capacitive component 910 may be a single device of fixed capacitance while the inductive component 908 might be implemented as two separate devices—one with a fixed value and the other as a variable inductor. In some embodiments, the variable capacitor may be a varactor—a type of diode which changes capacitance with voltage application. However, other variable capacitors that can change the capacitance with application of voltage are also within the scope of the embodiments described herein. In some embodiments, the variable inductor may be a microelectromechanical system (MEMS) variable inductor. However, other variable inductors that can change the inductance with application of voltage are also within the scope of the embodiments described herein.

As mentioned above, in some embodiments the system 800 can automatically tune the frequency of the electric field generated via a feedback loop. For example, the controller 808 may send the frequency control signal based on a voltage received from the quadrature demodulator 810. In other embodiments, the controller 808 may send the frequency control signal based on one or more voltages received from the low pass filter 814, the signal processor 816, the electric field generator 801, and/or other components of the system 800.

In some embodiments, the controller 808 can tune the electric field generator 804 without receive any response from the quadrature demodulator 810, the low pass filter 814, the signal processor 816, or other components of the system 800. An operator may manually adjust the knobs on the controller to tune the LC tank oscillator based on his or her observation of the data from any components in system 800. Other manual adjustment techniques and mechanisms are also within the scope of the embodiments described herein.

In some embodiments, the controller 808 can sample the detected response from the quadrature demodulator 810 to determine other changes in the frequency not caused by the LC tank oscillator. In this regard, the controller 808 can hold the variable components of the LC tank oscillator constant, and act as a monitoring system for detecting other frequency changing variables. For example, the controller 808 may pick up frequency changes caused by the external sensor device 802. In some embodiments, the monitored information can be fed directly to the signal processor 816 for analysis or for outputting to an external display.

Figure 10:
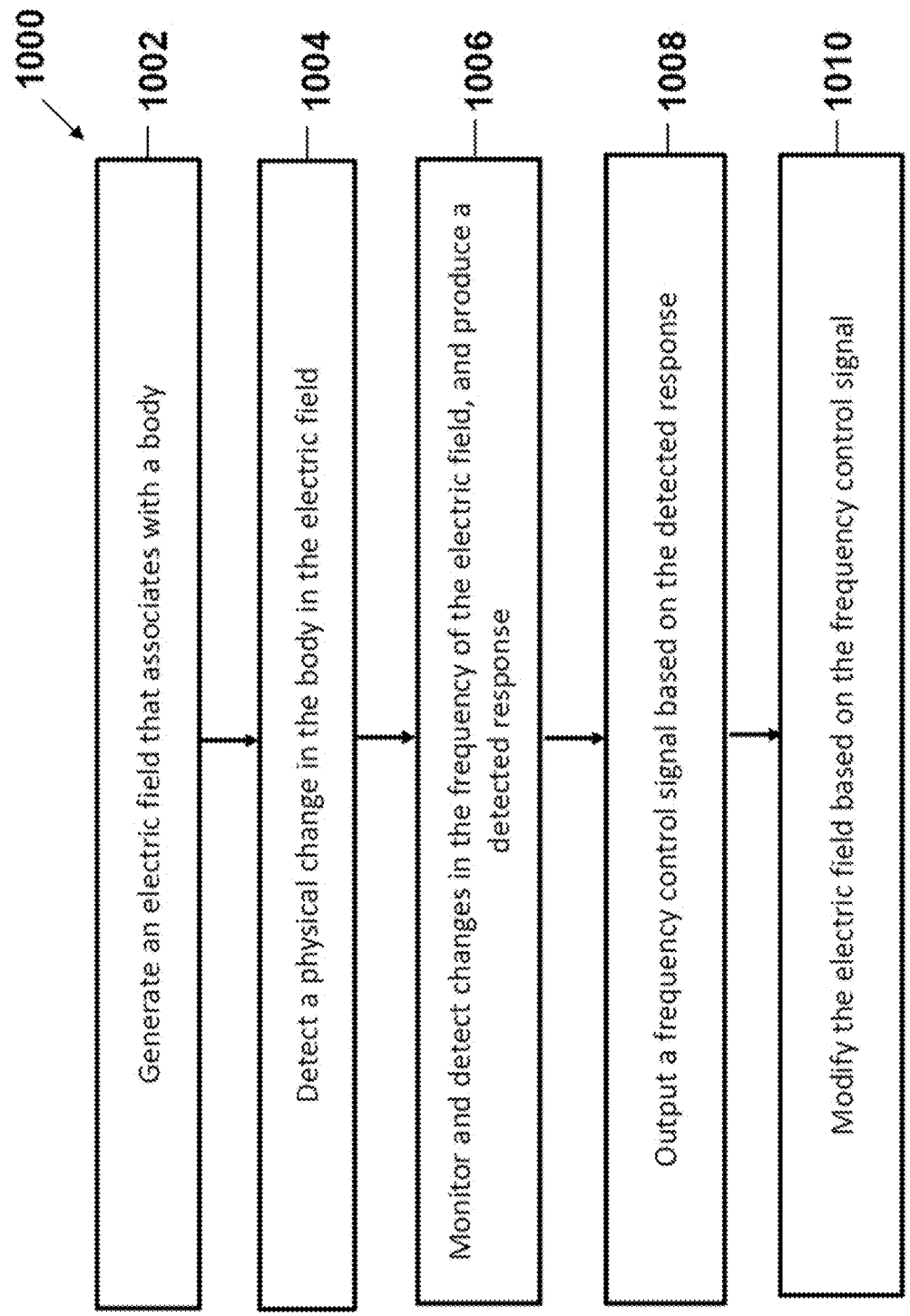
FIG. 10 illustrates an example of a process of detecting and analyzing changes in a body according to certain embodiments.

FIG. 10 is a flow chart illustrating a process 1000 of detecting and analyzing changes in a body according to certain embodiments of the present disclosure. The process 1000 is illustrated in connection with the system 800 shown in FIG. 8. In some embodiments, the process 1000 can be modified by, for example, having steps rearranged, changed, added, and/or removed.

At step 1002, an electric field associated with the body is generated. The body need not be the whole body, it can be a specific part of the body. In some embodiments, the electrical field is generated by using the electric field generator 804, which creates an electric field that illuminates a desired area of detection. The process 1000 then proceeds to step 1004.

At step 1004, a physical change in the body is detected in the electric field generated in step 1002. In some embodiments, the external sensor device 802 is used to monitor the area around and within the body. The external sensor device 802 is not required to physically contact the body being studied. The process 1000 then proceeds to step 1006.

At step 1006, changes in the frequency of the electric field is detected and monitored, and a detected response is produced. In some embodiments, the quadrature demodulator 810 is used to monitor and detect the frequency change of the electric field. Referring to FIG. 8, in some embodiments, frequency changes are reflected in the transfer function of the quadrature demodulator 810, where the transfer function shows the relationship between the voltage output and the frequency of the input signal from the electric field generator 804. In some embodiments, the detected response is subsequently send to one or more other components for further analysis or processing. In some embodiments, the detected response is sent to a component not depicted in FIG. 8. In some embodiments, the detected response is sent to the controller 808. In some embodiments, the detected response is initially sent to another component such as the low pass filter 814, before passing on to the controller 808. The process 1000 then proceeds to step 1008.

At step 1008, a frequency control signal is outputted to a component for modifying the frequency of the electric field. In some embodiments, the adjuster 818 of the controller 808 is used to output the frequency control signal. And the electric field generator 804 is used to receive the frequency control signal. Referring back to FIG. 8, although in some embodiments the output of the controller 808 is fed directly to the input of the electric field generator 804, other communication paths are also possible. For example, the frequency control signal can be routed to another component not depicted in FIG. 8 before arriving at the electric field generator 804. In some embodiments, the frequency control signal is received by the tuner 820 of the electric field generator 804. In some embodiments, the frequency control signal is received by another component or circuit within the electric field generator 804 (not shown in FIG. 8). The process 1000 then proceeds to step 1010.

At step 1010, an electric field generated by the electric field generator is modified based on the frequency control signal. In some embodiments, the electric field being modified is the electric field generated in step 1002. In some embodiments, the electric field being modified is another electric field generated after step 1002. According to certain embodiments, the tuner 820 modifies the electric field based on the frequency control signal. In some embodiments, another component or circuit within the electric field generator (not shown) can modify the electric field based on the frequency control signal. In some embodiments, another component, not necessary in the system 800, can receive the frequency control signal and modify the electric field accordingly. In some embodiments, the process 1000 ends at step 1010. In some embodiments, the system 800 repeats the process 1000 multiple times to achieve a proper adjustment.

The following applications and/or methods are non-limiting examples of applying the disclosed subject matter.

In some embodiments, changes in capacitor excitation frequency can be remotely sensed to alleviate the need for analog data reduction at the sensor.

In some embodiments, blood pressure can be measured by isolating a body region using a pressure "doughnut" and then releasing pressure and monitoring the return of blood flow as a result. Traditional means enclosing a limb to close an artery and monitor the pressure at which the artery opens up as the pressure is released. With the disclosed embodiments, a body region can be determined that excludes blood by closing capillaries (within the 'doughnut' pressure region) and monitoring the pressure at which they then open again. This simplification of application could then be applied to in-seat circumstances in hospital/clinic waiting rooms and the like.

In some embodiments, first derivatives can be used to find a recurring pattern in a combined time series signal of heartbeat and respiration such that the respiration signal can be subtracted from the combined signal to leave the heartbeat signal.

In some embodiments, the mathematical notion of Entropy (H) can be used to analyze a heartbeat signal and extract event timing information with respect to characterizing heart processes.

In some embodiments, wavelet analysis can be used to disambiguate complex time series data with highly variable frequency compositions. Signals that vary their frequency in time are resistant to effective analysis using traditional digital techniques such as fast Fourier transform (FFT). Wavelets provide the notion of short pattern correlation that can be applied to a sliding window of time series data in order to provide a second correlation time series that indicates the time at which a test pattern or "wavelet" is found within the first time series.

In some embodiments, a low resolution FFT can be used to peak search for power levels in a correlation function. This FFT power analysis is then used to set the correlation cutoff level and thus determine higher resolution correlated frequencies based on the power levels provides by the FFT. The FFT essentially filters out correlations below a particular power level so that more strongly correlated signals can remain. This provides a way of efficiently 'normalizing' the power levels relative to one another in trying to separate low frequency signals that are relatively close in frequency but widely separated in power without having to increase the resolution of the FFT with attendant significantly increased FFT window acquisition time.

In some embodiments, Kalman filters can be used to process the effect of changes in permittivity as indicated by a time series data such that the filter relates the predicted next value in a time series in maintaining a useable moving average for the purposes of normalizing a highly variable signal from a sensor with high dynamic range.

In some embodiments, measurement of the temperature of a body or substance can be obtained by measuring the permittivity of said body or substance where such permittivity may be correlated to temperature.

In some embodiments, measurement of the pressure within a body, substance, and/or liquid can be obtained by measuring the permittivity of said body, substance, and/or liquid where such permittivity may be correlated to pressure.

In some embodiments, stress levels in an individual can be determined by analyzing his or her motion, heartbeat characteristics and respiration using a remote, non-contact, biometric sensor.

In some embodiments, the quality of food in food processing and handling operations can be monitored by correlating the qualities of the food to the measured permittivity of the food item.

In some embodiments, the characteristics (e.g., turbulence, flow, density, temperature) of a fluid (e.g., paint, blood, reagents, petroleum products) can be monitored by correlating the characteristics of the fluid to the objective characteristics of the fluid.

In some embodiments, cavities and/or impurities in solid materials can be found. Such application can be used in areas such as the detection of delamination in composite materials, voids in construction materials, entrained contaminants, and/or the quality of fluid mixing.

In some embodiments, contraband enclosed within solid objects can be found.

In some embodiments, the life signs of infants in cribs, pushchairs and/or car seats can be monitored.

In some embodiments, the presence and life signs located in automobiles can be detected for the purposes of providing increased passenger safety, deploying airbags, and/or prevent baby from being left behind.

In some embodiments, the sentience of a driver can be detected by using heartbeat variability. In some embodiments, gestures such as the head-nod signature motion.

In some embodiments, the life signs in unauthorized locations (e.g., smuggling and/or trafficking) can be discovered.

In some embodiments, the quality of glass manufacture can be assessed by detecting variations in thickness, poor mixing, and/or the entrainment of impurities and/or.

In some embodiments, the nature of underground/subsurface texture and infrastructure (pipes and similar) can be assessed.

In some embodiments, the external sensor device disclosed herein can be combined with other sensors (e.g., camera, echolocation, pressure/weight/accelerometers) to provide enhanced sensor application using sensor "fusion."

In some embodiments, certain body conditions can be detected. The body conditions include conditions of the body relating to heart-lung functions, pulmonary fluid levels, blood flow and function, large and small intestine condition and process, bladder condition (full/empty) and process (rate fill/empty), edema and related fluid conditions, bone density measurement, and any other suitable condition or combination of conditions.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods, and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

A Sensor Strap

What follows is an example of a sensor strap usable, in various embodiments, as portions of a BPCD including an antenna. In some embodiments, an electronics module of the sensor strap (e.g., electronics module 1350 as illustrated in FIG. 13 or electronics module 1450 as illustrated in FIG. 14), comprises at least a portion of the BPCD, such as an analog front-end of the BPCD. In various embodiments, a sensor pad (such as sensor pad 1320 as illustrated in FIG. 13 or sensor pad 1410 as illustrated in FIG. 14) functions as part of or all of an antenna of the BPCD.

As discussed herein, a sensor strap system according to an embodiment of the present disclosure includes: a sensor capable of detecting physical or physiological activities or conditions of a target subject; a top strap extending along a top surface of a bed, the top strap configured to secure the sensor to the top surface of the bed; and a circumferential strap extending about a circumference of the bed and coupled with the top strap.

Many known monitoring systems for beds rely on a type of sensor that works at a distance through the mattress. These are placed below the mattress, against the base of the bed or between the mattress and box springs.

The present disclosure concerns a monitor for subjects in beds, in chairs, in cribs, and in any other furniture or conveyance or structure which contacts or is in proximity with the subject's back, side, front, or any other suitable external surfaces. Furthermore, some example embodiments require the sensor be located close to the subject being monitored, for example, between the subject and the mattress or cushion of the furniture.

In some embodiments, in the case of a bed, it is desirable to easily locate the sensor on the top surface of the mattress, to fix it in place regardless of the movement of the mattress or bed coverings, and to allow bed coverings to be applied to the mattress with minimal restriction.

Detailed Description of Sensor Strap Embodiments

In the following description, numerous specific details are set forth regarding the systems, methods and media of the disclosed subject matter and the environment in which such systems, methods and media may operate, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are exemplary, and that it is contemplated that there are other systems, methods and media that are within the scope of the disclosed subject matter.

Embodiments described herein include sensor strap systems and methods for attaching and securing a sensor strap system to an object (e.g., a mattress, cushion, chair, conveyance, or other type of furniture) ("Base"). According to some embodiments, a sensor of the sensor strap system is placed/positioned to contact or juxtaposition with a sensor target (such as a human or animal subject). According to some embodiments, the sensor strap system is configured to be secured to a Base effortlessly, with minimum interference with the accessories of the Base (such as sheet cover and mattress padding etc.). According to some embodiments, the sensor strap system facilitates detection of physical and/or physiological activities/conditions of a target subject. The activities and conditions include, for example, the target subject's general movement (e.g., getting into or out of the chair or mattress), and/or the target subject's physiological state such as heart and lung activity or coughing patterns etc. During the detection, the target subject may be reclined or otherwise in contact with the sensor of the sensor strap system (e.g., sensor pad, plate, sheet, or any other suitable components of the sensor strap system). In some embodiments, the sensor of the sensor strap system is a sensor pad. In some embodiments, the sensor pad is rigid. In some embodiments, the sensor pad is flexible. In some embodiments, the sensor pad is positioned to physically contact a subject (e.g., human or animal subject).

According to certain embodiments, the sensor of the sensor strap system (e.g., sensor pad or sensor plate) is secured to a body-contacting surface of an object (such as top of a mattress, or the sitting surface of a chair). However, the present disclosure is applicable to any object with a broad surface, and enough compression resistance to allow a circumferential strap to secure the sensor strap system, without causing substantial deformation to the object.

According to some embodiments, the sensor strap system has means for securing itself to a bed and means for keeping the sensor (e.g., sensor pad) flat over the top surface of the bed. In some embodiments, the means for securing the system include a set of straps configured to keep the sensor pad secured on the mattress. In some embodiments, the set of straps are configured to be easily installed and removed. In some embodiments, the sensor strap system is designed to allow easy exchange of covers, such as bed sheets, so that the covers can be replaced without disrupting sensor pad's position.

According to some embodiments, the sensor strap system has two sets of straps. The first set of straps (e.g., circumferential strap or straps) is designed to run around the circumference of a mattress. In some embodiments, the circumferential strap or straps incorporate various securing mechanisms such as buckles or other suitable tensioning mechanisms designed to help fixing the sensor strap system against the surfaces of the mattress (without the need to run straps underneath the mattress). The second set of straps (e.g., top strap or straps), according to certain embodiments, emerge from the sensor pad and are configured to connect to the circumferential strap or straps. In some embodiments, the top strap or straps extend to the sides of the mattress and connect with the circumferential strap or straps. In some embodiments, the connections of the top strap or straps to the circumferential straps may be permanent. In some embodiments, the connections are accomplished via detachable mechanisms such as clasps, buckles, or any other suitable mechanisms.

In some embodiments, the circumferential strap or straps are made of inelastic materials such as nylon webbing. Circumferential strap or straps made with inelastic material may be coupled with certain tension adjustment mechanisms to allow the strap or straps to take up slack and make the hold more secure. In some embodiments, the circumferential strap or straps are made of an elastic material that may not need tension adjustment mechanisms or buckles to keep the sensor strap system secured. In some embodiments, the circumferential strap or straps incorporate a rigid corner piece to provide a point of reference at one corner of the mattress or other base platform.

In some embodiments, the top strap or straps are made of an elastic material so that when a subject (e.g., human or animal) moves on the top of the bed, the strap or straps could flex to allow for normal elastic depression or extension. According to certain embodiments, the top strap or straps are attached to the circumferential strap or straps with permanent attachments such as stitching or permanent adhesives. In other embodiments, the top strap or straps are connected to circumferential straps via one or more adjustable mechanisms such as buckles. In some embodiments, the attachment mechanisms may be permanent such that the position of the sensor relative to the length of the bed is fixed. In other embodiments, the sensor strap system is configured to allow the sensor pad to connect/attach to different positions along the circumferential strap or straps. Such configuration allows users to adjust the position of the sensor pad along the bed.

According to some embodiments, the sensor pad has electrical connections with one or more electrical conductors. These conductors may be attached to or embedded in the elastic top straps so that they can be routed to the circumferential strap or straps. In some embodiments, the conductors are made of flexible materials that can expand and contract as the top strap or straps flex. In some embodiments, the conductors may extend due to a subject depressing the top of the mattress. In one embodiment, the extension and contraction of the conductors are accomplished via a pattern (e.g., a zig-zag pattern or any other suitable patterns) of a flexible cable. In other embodiments, the conductors may be a cable (electric cable) with a slack loop which would allow the cable to extend and retract. In other embodiments, the conductors may be incorporated into the strap or straps by means of conductive threads.

In some embodiments, once the electrical cable reaches the circumferential strap or straps, it travels along the strap or straps to an electronics module. In one embodiment, this module is attached to the circumferential strap or straps. In some embodiments, this module is attached to the top strap or straps as it travels down the side of the mattress (against one side of the mattress). In yet another embodiment the module is free-hanging.

In some embodiments, a secondary cable is used to extend from the module to power supply or other electronics. In some embodiments, the cable travels in the top strap or straps. In some embodiments, the cable passes through a part of the circumferential strap or straps. In some embodiments, the electronic cable is free-hanging in whole or in part.

The present disclosure will be better understood and objects other than those set forth above will become apparent when consideration is given to the following detailed description thereof. Such description makes reference to the annexed drawings disclosed herein.

FIG. 13 illustrates a sensor strap system 1300 installed on a mattress according to certain embodiments. Sensor strap system 1300 has a sensor pad 1320 secured to the top of mattress 1310. Sensor strap system 1300 applies to a mattress 1310 as the background or platform. As shown in FIG. 13, the circumferential strap 1330 of sensor strap system 1300 is secured to the side of mattress 1310 without passing anything underneath mattress 1310. Further, the top strap 1340 of sensor strap system 1300 extends over the sides of mattress 1310 and connects to the circumferential strap 1330. On the side of sensor strap system 100, an electronics module 1350 is attached to the top strap 1340 and connected to its external power or communication cable 1360. According to some embodiments, when no subject (e.g., human body) is exerting force on the sensor pad 1320, the top strap 1340 has minimally-loaded elasticity that keeps the sensor pad 1320 flat and in its nominal position to accomplish its sensing function. The top strap 1340 also keeps the sensor pad 1320 from folding or lifting to disturb the aesthetics of flat sheets or blankets. In some embodiments, the sensor strap system 1300 may include more than one circumferential strap and/or more than one top strap. In some embodiments, sensor strap system 1300 may include fewer components. In some embodiments, sensor strap system 1300 may include suitable additional or alternative components.

FIG. 14 illustrates a system 1400 for securing a sensor pad to the top of a mattress according to certain embodiments. As shown, system 1400 has a sensor pad 1410 secured to the circumferential strap 1420. In this embodiment, the sensor pad 1410 is connected to the circumferential strap 1420 via elastic top strap 1430 which emerges from permanent attachments to the sensor pad 1410 and extends over the edge of the mattress surface to connect to the circumferential strap 1420. In some embodiments, the top strap 1430 is attached to the circumferential strap 1420 by permanent mechanisms such as stitching, adhesive, or any other suitable mechanisms. In some embodiments, the top strap 1430 is attached to the circumferential strap 1420 by a removable/detachable mechanism such as a buckle or clasp 1460. In some embodiments, the buckle or clasp 1460 can be any other suitable mechanisms. This buckle or clasp may take up slack in the top straps 1430 to ensure that the top strap 1430 is taut and minimally stretched when there is no load (e.g., body) on the bed. In some embodiments, the location of the buckle or clasp 1460 can change along the circumferential strap 1420 to facilitate changing the location of the sensor pad 1410 on the top of the mattress. In some embodiments, a rigid corner piece 1470 is incorporated to establish a reference point in one or more corners of the mattress. According to some embodiments, the rigid corner piece 1470 facilitates positioning of the sensor pad 1410. In some embodiments, the electrical cable 1440 travels on or within the top strap 1430 to connect to an electronics module 1450. FIG. 14 depicts electronics module 1450 connected to the circumferential strap 1420 between claps 1460. In some embodiments, electronics module 1450 may be placed at another segment of the circumferential strap 1420. In some embodiments, system 1400 may include fewer components. In some embodiments, the sensor strap system 1400 may include more than one circumferential strap and/or more than one top strap. In some embodiments, system 1400 may include suitable additional or alternative components.

FIG. 3 is a flow chart illustrating a process 1500 of securing a sensor strap system to a mattress according to certain embodiments of the present disclosure. The process 1500 is illustrated in connection with the system 1300 shown in FIG. 13 as a non-limiting example. In some embodiments, the process 1500 can be modified by, for example, having steps rearranged, changed, added, and/or removed.

At step 1502, circumferential strap or straps 1330 are secured around the circumference along the sides of mattress 1310. In some embodiments, circumferential strap or straps 1330 are made of an elastic material. In some embodiments, circumferential strap or straps 1330 are made of inelastic materials. In some embodiments, an electronic module is placed on circumferential strap or straps 1330. In some embodiments, circumferential strap or straps 1330 are connected to top strap or straps 1340 via detachable mechanisms such as buckles or claps. The process 1500 then proceeds to step 1504.

At step 1504, sensor pad 1320 is placed flat on mattress 1310. In some embodiments, the desired area of detection is adjacent to, or proximate to, the torso of a body that is going to be monitored. In some embodiments, sensor pad 1320 is generally placed across the upper-middle section of mattress 1310. The process 1500 then proceeds to step 1506.

At step 1506, sensor pad 1320 is attached to circumferential strap or straps 1330 via top strap or straps 1340 that emerge from sensor pad 1320. In some embodiments, top strap or straps 1340 are made of an elastic material. In some embodiments, top strap or straps 1340 are made of inelastic materials. In some embodiments, the top strap or straps 1340 have embedded wires/cables that runs to an electronic module located on circumferential strap or straps 1330.

It is to be understood that the disclosed subject matter is not limited in its application to the details of construction and to the arrangements of the components set forth in the description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

Example Implementation Techniques

In some embodiments, various combinations of one or more portions of operations performed for and/or structure associated with the techniques described in the present disclosure (such as measuring physiological parameters of a human body) and/or systems implementing the techniques, as well as portions of a processor, microprocessor, system-on-a-chip, application-specific-integrated-circuit, hardware accelerator, or other circuitry providing at least portions of the aforementioned operations, are specified by a specification compatible with processing by a computer system. The specification is in accordance with various descriptions, such as hardware description languages, circuit descriptions, netlist descriptions, mask descriptions, or layout descriptions. Example descriptions include: Verilog, VHDL, SPICE, SPICE variants such as PSpice, IBIS, LEF, DEF, GDS-II, OASIS, or other descriptions. In various embodiments, the processing includes a combination of interpretation, compilation, simulation, and synthesis to produce, to verify, or to specify logic and/or circuitry suitable for inclusion on one or more integrated circuits. A given integrated circuit, according to various embodiments, is compatible with design and/or manufacture according to a variety of techniques. The techniques include a programmable technique (such as a field or mask-programmable gate array integrated circuit), a semi-custom technique (such as a wholly or partially cell-based integrated circuit), and a full-custom technique (such as an integrated circuit that is substantially specialized), a combination thereof, or another technique compatible with design and/or manufacture of integrated circuits.

In some embodiments, various combinations of at least portions of operations as described by a computer readable medium having a set of instructions stored tin the present disclosure, are performed by execution and/or interpretation of one or more program instructions, by interpretation and/or compiling of one or more source and/or script language statements, or by execution of binary instructions produced by compiling, translating, and/or interpreting information expressed in programming and/or scripting language statements. The statements are compatible with a standard programming or scripting language (such as assembly language, C, C++, Fortran, Pascal, Ada, Java, VBscript, and Shell). One or more of the program instructions, the language statements, or the binary instructions, are optionally stored on one or more computer readable storage medium elements. In various embodiments, some, all, or various portions of the program instructions are realized as one or more functions, routines, subroutines, in-line routines, procedures, macros, or portions thereof.

Certain choices have been made in the description merely for convenience in preparing the text and drawings, and unless there is an indication to the contrary, the choices should not be construed per se as conveying additional information regarding structure or operation of the embodiments described. Examples of the choices include: the particular organization or assignment of the designations used for the figure numbering and the particular organization or assignment of the element identifiers (the callouts or numerical designators, e.g.) used to identify and reference the features and elements of the embodiments.

Various forms of the words 'include' and 'comprise' are specifically intended to be construed as abstractions describing logical sets of open-ended scope and are not meant to convey physical containment unless described explicitly (such as followed by the word 'within').

Although the foregoing embodiments have been described in some detail for purposes of clarity of description and understanding, implementations are not limited to the details provided. There are many embodiments of the present disclosure. The disclosed embodiments are exemplary and not restrictive.

It will be understood that many variations in construction, arrangement, and use are possible consistent with the description, and are within the scope of the claims of the issued patent. For example, interconnect and function-unit bit-widths, clock speeds, and the type of technology used are variable according to various embodiments in a given component block. The names given to interconnect and logic are merely exemplary, and should not be construed as limiting the concepts described. The order and arrangement of flowchart and flow diagram process, action, and function elements are variable according to various embodiments. Also, unless specifically stated to the contrary, value ranges specified, maximum and minimum values used, or other particular specifications (such as file types; and the number of entries or stages in registers and buffers), are merely those of the described embodiments, are expected to track improvements and changes in implementation technology, and should not be construed as limitations.

Functionally equivalent techniques known in the art are employable instead of those described to implement various components, sub-systems, operations, functions, routines, subroutines, in-line routines, procedures, macros, or portions thereof. It is also understood that many functional aspects of embodiments are realizable selectively in either hardware (e.g., generally dedicated circuitry) or software (e.g., via some manner of programmed controller or processor), as a function of embodiment-dependent design constraints and technology trends of faster processing (facilitating migration of functions previously in hardware into software) and higher integration density (facilitating migration of functions previously in software into hardware).

Specific variations in various embodiments include, but are not limited to: differences in partitioning; different form factors and configurations; use of different operating systems and other system software; use of different interface standards, network protocols, or communication links; and other variations to be expected when implementing the concepts described in the present disclosure in accordance with the unique engineering and business constraints of a particular application.

The embodiments have been described with detail and environmental context well beyond that used for a minimal implementation of many aspects of the embodiments described. Those of ordinary skill in the art will recognize that some embodiments omit disclosed components or features without altering the basic cooperation among the remaining elements. It is thus understood that much of the details disclosed are not required to implement various aspects of the embodiments described. To the extent that the remaining elements are distinguishable from the prior art, components and features that are omitted are not limiting on the concepts described in the present disclosure.

All such variations in design are insubstantial changes over the teachings conveyed by the described embodiments. It is also understood that the embodiments described in the present disclosure have broad applicability to other computing and networking applications, and are not limited to the particular application or industry of the described embodiments. Embodiments are thus to be construed as including possible modifications and variations encompassed within the scope of the claims of the issued patent.

Additional Example Embodiments

A system is disclosed herein. The system includes an electric field generator comprising a differential oscillator configured to oscillate at a nominal frequency, the electric field generator connected to a differential antenna configured to radiate an electric field; a differential detector configured to measure a frequency of the generated electric field as it interacts with a body in a reactive near-field region of the electric field; and a computation unit configured to: determine, for each of one or more internal components of the body, a respective periodic behavior in the measured frequency indicative of movement of the internal component, and compute, for each of the one or more internal components of the body, a respective rate of the movement of the internal component according to the respective periodic behavior in the measured frequency.

In one embodiment of the foregoing system, the differential oscillator comprises one of a differential tank oscillator or a differential resonator.

In one embodiment of the foregoing system, the differential detector comprises a differential demodulator.

In one embodiment of the foregoing system, the differential detector comprises one of a differential quadrature demodulator, a differential wideband analog-to-digital converter, or a combination of a differential sample-and-hold circuit and an analog-to-digital converter.

In one embodiment of the foregoing system, the body is a human body.

In one embodiment of the foregoing system, the one or more internal components of the body comprise a heart of the human body.

In one embodiment of the foregoing system, the one or more internal components of the body comprise a femoral artery of the human body.

In one embodiment of the foregoing system, the one or more internal components of the body comprise a heart of the human body and lungs of the human body.

In one embodiment of the foregoing system, one of the respective rates is a heart rate.

In one embodiment of the foregoing system, the heart rate is a nighttime resting heart rate.

In one embodiment of the foregoing system, the computation unit is further configured, in computation of the nighttime resting heart rate, to not use a portion of the measured frequency that is not indicative of movement of a heart of the human body.

In one embodiment of the foregoing system, the computation unit is further configured, in computation of the nighttime resting heart rate, to not use a portion of the measured frequency that corresponds to a non-periodic behavior.

In one embodiment of the foregoing system, the differential detector is further configured to measure an amplitude of the electric field; and the computation unit is further configured to determine the non-periodic behavior according to the measured amplitude.

In one embodiment of the foregoing system, the respective rates comprise a heart rate and a respiration rate.

In one embodiment of the foregoing system, the measuring of the frequency of the generated electric field does not comprise measuring a reflection of the generated electric field.

In one embodiment of the foregoing system, a first portion of the computation unit is co-located with the differential detector, and a second portion of the computation unit is remotely located from the differential detector and connected to the first portion of the computation unit over a network; the first portion of the computation unit is configured to determine the respective periodic behavior for each of the one or more internal components of the body; and the second portion of the computation unit is configured to compute the respective rate of the movement for each of the one or more internal components of the body.

A method is disclosed herein. The method includes generating an electric field with an electric field generator comprising a differential oscillator oscillating at a nominal frequency; radiating the electric field through a differential antenna connected to the electric field generator; measuring, with a differential detector, a frequency of the generated electric field as it interacts with a body in a reactive near-field region of the electric field; determining, for each of one or more internal components of the body, a respective periodic behavior in the measured frequency indicative of movement of the internal component; and computing, for each of the one or more internal components of the body, a respective rate of the movement of the internal component according to the respective periodic behavior in the measured frequency.

In one embodiment of the foregoing method, the differential oscillator comprises one of a differential tank oscillator or a differential resonator.

In one embodiment of the foregoing method, the differential detector comprises a differential demodulator.

In one embodiment of the foregoing method, the differential detector comprises one of a differential quadrature demodulator, a differential wideband analog-to-digital converter, or a combination of a differential sample-and-hold circuit and an analog-to-digital converter.

In one embodiment of the foregoing method, the body is a human body.

In one embodiment of the foregoing method, the one or more internal components of the body comprise a heart of the human body.

In one embodiment of the foregoing method, the one or more internal components of the body comprise a femoral artery of the human body.

In one embodiment of the foregoing method, the one or more internal components of the body comprise a heart of the human body and lungs of the human body.

In one embodiment of the foregoing method, one of the respective rates is a heart rate.

In one embodiment of the foregoing method, the heart rate is a nighttime resting heart rate.

In one embodiment of the foregoing method, the computing the nighttime resting heart rate comprises not using a portion of the measured frequency that is not indicative of movement of a heart of the human body.

In one embodiment of the foregoing method, the computing the nighttime resting heart rate comprises not using a portion of the measured frequency that corresponds to a non-periodic behavior.

In one embodiment of the foregoing method, the method further includes measuring, with the differential detector, an amplitude of the electric field; and determining the non-periodic behavior according to the measured amplitude.

In one embodiment of the foregoing method, the respective rates comprise a heart rate and a respiration rate.

In one embodiment of the foregoing method, the measuring of the frequency of the generated electric field does not comprise measuring a reflection of the generated electric field.

A method is disclosed herein. The method includes generating, with an electric field generator, an electric field at a nominal amplitude; radiating the electric field through an antenna; measuring an amplitude of the generated electric field as it interacts with a body in a reactive near-field region of the electric field; adjusting the nominal amplitude according to the measured amplitude; generating, with the electric field generator, a modified electric field at a nominal frequency and the adjusted nominal amplitude; radiating the modified electric field through the antenna; measuring a frequency of the modified electric field as it interacts with the body in the reactive near-field region of the modified electric field; determining, for each of one or more internal components of the body, a respective periodic behavior in the measured frequency corresponding to movement of the internal component; and computing, for each of the one or more internal components of the body, a respective rate of the movement of the internal component based on the determined respective periodic behavior in the measured frequency.

In one embodiment of the foregoing method, the adjusting the nominal amplitude is in response to the measured amplitude being below a determined lower threshold.

In one embodiment of the foregoing method, the method further includes: measuring a second amplitude of the electric field as the body moves away from the antenna; and adjusting the adjusted nominal amplitude in response to the second measured amplitude being above a determined upper threshold.

In one embodiment of the foregoing method, the adjusting the nominal amplitude is in response to a quality measure of a behavior in a measured frequency corresponding to movement of at least one of the one or more internal components of the body being below a specified limit.

In one embodiment of the foregoing method, the quality measure comprises a signal-to-noise ratio.

In one embodiment of the foregoing method, the method further includes adjusting the nominal frequency; and determining, based on the adjusted nominal frequency, a subsequent respective periodic behavior corresponding to a movement of at least one of the one or more internal components of the body following the adjusting the nominal frequency.

In one embodiment of the foregoing method, the body is a human body.

In one embodiment of the foregoing method, the method further includes measuring a second amplitude of the electric field; and determining, based on the second measured amplitude, whether the human body is within the reactive near-field region of the electric field.

In one embodiment of the foregoing method, the one or more internal components of the body comprise a heart of the human body.

In one embodiment of the foregoing method, the method further includes computing a heart rate of the human body according to the determined respective periodic behavior in the measured frequency corresponding to movement of the heart.

In one embodiment of the foregoing method, the one or more internal components of the body comprise a heart of the human body and lungs of the human body.

In one embodiment of the foregoing method, the respective rate of the movement of the heart of the human body is a nighttime resting heart rate; and the respective rate of the movement of the lungs of the human body is a nighttime resting respiration rate.

In one embodiment of the foregoing method, the adjusting the nominal amplitude is configured to not increase the nominal amplitude beyond a determined value where a total radiated power level would exceed a determined power level.

In one embodiment of the foregoing method, the adjusting the nominal amplitude is configured to adjust the nominal amplitude with a time constant that is longer than an expected duration of a non-periodic behavior in the measured amplitude corresponding to a movement of the body.

In one embodiment of the foregoing method, the time constant is at least ten times longer than the expected duration of the non-periodic behavior in the measured amplitude corresponding to the movement of the body.

A system is disclosed herein. The system includes an electric field generator configured to generate an electric field at a nominal frequency and a nominal amplitude, the electric field generator connected to an antenna configured to radiate the electric field; a detector configured to measure a frequency and an amplitude of the generated electric field as it interacts with a body in a reactive near-field region of the electric field; a computation unit configured to: determine, for each of one or more internal components of the body, a respective periodic behavior in the measured frequency corresponding to movement of the internal component, and compute, for each of the one or more internal components, a respective rate of the movement of the internal component based on the determined respective periodic behavior in the measured frequency; and a gain control circuit configured to adjust the nominal amplitude according to the measured amplitude.

In one embodiment of the foregoing system, the gain control circuit is further configured to adjust the nominal amplitude in response to the measured amplitude being below a determined lower threshold.

In one embodiment of the foregoing system, the differential detector is further configured to measure a second amplitude of the electric field as the body moves away from the antenna, and the gain control circuit is further configured to adjust the nominal amplitude in response to the second measured amplitude being above a determined upper threshold.

In one embodiment of the foregoing system, the gain control circuit is configured to adjust the nominal amplitude in response to a quality measure of at least one of the respective periodic behaviors in the measured frequency being below a specified limit.

In one embodiment of the foregoing system, the system further includes a tuner configured to adjust the nominal frequency; and the computation unit is further configured to determine, based on the adjusted nominal frequency, a subsequent respective periodic behavior corresponding to a movement of at least one of the one or more internal components of the body following the adjustment of the nominal frequency.

In one embodiment of the foregoing system, the body is a human body.

In one embodiment of the foregoing system, the detector is further configured to measure a second amplitude of the electric field; and the computation unit is further configured to determine, based on the second measured amplitude, whether the human body is within the reactive near-field region of the electric field.

In one embodiment of the foregoing system, the one or more internal components of the body comprise a heart of the human body.

In one embodiment of the foregoing system, the computation unit is further configured to compute a heart rate of the human body according to the determined respective periodic behavior in the measured frequency corresponding to movement of the heart.

In one embodiment of the foregoing system, the one or more internal components of the body comprise a heart of the human body and lungs of the human body.

In one embodiment of the foregoing system, the respective rate of the movement of the heart of the human body is a nighttime resting heart rate; and the respective rate of the movement of the lungs of the human body is a nighttime resting respiration rate.

In one embodiment of the foregoing system, the gain control circuit is further configured to not increase the nominal amplitude beyond a determined value where a total radiated power level would exceed a determined power level.

In one embodiment of the foregoing system, the gain control circuit is further configured to adjust the nominal amplitude with a time constant that is longer than an expected duration of a non-periodic behavior in the measured amplitude corresponding to a movement of the body.

In one embodiment of the foregoing system, the electric field generator comprises a differential oscillator; and the antenna is a differential antenna.

In one embodiment of the foregoing system, a first portion of the computation unit is co-located with the detector, and a second portion of the computation unit is remotely located from the detector and connected to the first portion of the computation unit over a network; the first portion of the computation unit is configured to determine the respective periodic behavior for each of the one or more internal components of the body; and the second portion of the computation unit is configured to compute the respective rate of the movement for each of the one or more internal components of the body.

A method of predicting a condition of a human body is disclosed herein. The method includes generating, with an electric field generator, an electric field at a nominal frequency; measuring, at multiple time points during a measuring period, one or more properties of the generated electric field, the one or more properties of the electric field changing over time due to interactions with a human body in a reactive near-field region of the electric field; determining, from the measured one or more properties, one or more periodic behaviors and one or more non-periodic behaviors; computing, from at least one of the one or more periodic behaviors and at least one of the one or more non-periodic behaviors, one or more physiological parameters of the human body; and detecting, from the one or more physiological parameters, one or more symptoms of a condition of the human body.

In one embodiment of the foregoing method, the measuring the one or more properties of the electric field comprises: measuring changes in the one or more properties of the electric field as the one or more properties change due to the interactions with the human body.

In one embodiment of the foregoing method, the one or more properties comprise one or more of a phase, a frequency, and an amplitude.

In one embodiment of the foregoing method, the one or more non-periodic behaviors comprise at least one of sleep apnea or coughing.

In one embodiment of the foregoing method, the one or more non-periodic behaviors comprise movement of a limb of the human body.

In one embodiment of the foregoing method, the determining the one or more non-periodic behaviors comprises determining a disruption in at least one of the one or more periodic behaviors.

In one embodiment of the foregoing method, the determining the one or more periodic behaviors is based at least on one or more time points of the multiple time points that do not include one or more other time points of the multiple time points corresponding to the one or more non-periodic behaviors.

In one embodiment of the foregoing method, the one or more physiological parameters comprise a frequency of coughing, and the one or more symptoms of the condition comprise the frequency of coughing increasing over a period of days.

In one embodiment of the foregoing method, the one or more physiological parameters comprise a frequency of movement at night, and the one or more symptoms of the condition comprise the frequency of movement at night increasing over a period of days.

In one embodiment of the foregoing method, the one or more physiological parameters comprise a nighttime resting volume of respiration, and the one or more symptoms of the condition comprise the nighttime resting volume of respiration decreasing over a period of days.

In one embodiment of the foregoing method, the one or more physiological parameters comprise a nighttime resting heart rate and a nighttime resting respiration rate.

In one embodiment of the foregoing method, the one or more physiological parameters comprise a respiration waveform.

In one embodiment of the foregoing method, the one or more symptoms of the condition comprise heart rate variability changing over a period of days.

In one embodiment of the foregoing method, the method further includes from the one or symptoms of the condition, predicting the condition of the human body.

In one embodiment of the foregoing method, the condition is onset of a Chronic Obstructive Pulmonary Disease (COPD) exacerbation.

In one embodiment of the foregoing method, the condition is one of Congestive Heart Failure (CHF) or sleep apnea.

A system of predicting a condition of a human body is disclosed herein. The system includes an electric field generator configured to generate an electric field at a nominal frequency; a detector configured to measure, at multiple time points during a measuring period, one or more properties of the generated electric field, the one or more properties of the electric field changing over time due to interactions with a human body in a reactive near-field region of the electric field; a computation unit configured to: determine, from the measured one or more properties, one or more periodic behaviors and one or more non-periodic behaviors, compute, from at least one of the one or more periodic behaviors and at least one of the one or more non-periodic behaviors, one or more physiological parameters of the human body, and detect, from the one or more physiological parameters, one or more symptoms of a condition of the human body.

In one embodiment of the foregoing system, the one or more properties comprise one or more of a phase, a frequency, and an amplitude.

In one embodiment of the foregoing system, the one or more periodic behaviors comprise at least one of respiration of the human body or a heartbeat of the human body.

In one embodiment of the foregoing system, the one or more non-periodic behaviors comprise at least one of sleep apnea or coughing.

In one embodiment of the foregoing system, the one or more non-periodic behaviors comprise movement of a limb of the human body.

In one embodiment of the foregoing system, the computation unit is further configured to determine the one or more periodic behaviors based at least on one or more time points of the multiple time points that do not include one or more other time points of the multiple time points corresponding to the one or more non-periodic behaviors.

In one embodiment of the foregoing system, the one or more physiological parameters comprise a frequency of coughing, and the one or more symptoms of the condition comprise the frequency of coughing increasing over a period of days.

In one embodiment of the foregoing system, the one or more physiological parameters comprise a frequency of movement at night, and the one or more symptoms of the condition comprise the frequency of movement at night increasing over a period of days.

In one embodiment of the foregoing system, the one or more physiological parameters comprise a nighttime resting volume of respiration, and the one or more symptoms of the condition comprise the nighttime resting volume of respiration decreasing over a period of days.

In one embodiment of the foregoing system, the one or more physiological parameters comprise a nighttime resting heart rate and a nighttime resting respiration rate.

In one embodiment of the foregoing system, the one or more physiological parameters comprise a respiration waveform.

In one embodiment of the foregoing system, the computation unit is further configured to predict the condition of the human body from the one or symptoms of the condition.

In one embodiment of the foregoing system, the condition is onset of a Chronic Obstructive Pulmonary Disease (COPD) exacerbation.

In one embodiment of the foregoing system, the condition is one of Congestive Heart Failure (CHF) or sleep apnea.

In one embodiment of the foregoing system, a first portion of the computation unit is co-located with the detector, and a second portion of the computation unit is remotely located from the detector and connected to the first portion of the computation unit over a network; the first portion of the computation unit is configured to determine the one or more periodic behaviors and the one or more non-periodic behaviors; and the second portion of the computation unit is configured to detect, from the one or more physiological parameters, one or more symptoms of a condition of the human body.

A computer-readable medium is disclosed herein. The computer-readable medium contains instructions which when executed by a processor perform steps of: receiving measurements, at multiple time points during a measuring period, of one or more properties of an electric field, the one or more properties of the electric field changing over time due to interactions with a human body in a reactive near-field region of the electric field, wherein the electric field is generated at a nominal frequency; determining, from the measured one or more properties, one or more periodic behaviors and one or more non-periodic behaviors; computing, from at least one of the one or more periodic behaviors and at least one of the one or more non-periodic behaviors, one or more physiological parameters of the human body; and detecting, from the one or more physiological parameters, one or more symptoms of a condition of the human body.

What is claimed is:

1. A system comprising:
   an electric field generator comprising a differential oscillator configured to oscillate at a nominal frequency, the electric field generator connected to a differential antenna configured to radiate an electric field;
   a differential detector configured to measure a frequency of the generated electric field as it interacts with a body in a reactive near-field region of the electric field; and
   a computation unit configured to:
   determine, for each of one or more internal components of the body, a respective periodic behavior in the measured frequency indicative of movement of the internal component, and
   compute, for each of the one or more internal components of the body, a respective rate of the movement of the internal component according to the respective periodic behavior in the measured frequency.

2. The system of claim 1, wherein the differential oscillator comprises one of a differential tank oscillator or a differential resonator.

3. The system of claim 1, wherein the differential detector comprises a differential demodulator.

4. The system of claim 1, wherein the differential detector comprises one of a differential quadrature demodulator, a differential wideband analog-to-digital converter, or a combination of a differential sample-and-hold circuit and an analog-to-digital converter.

5. The system of claim 1, wherein the body is a human body.

6. The system of claim 5, wherein the one or more internal components of the body comprise a heart of the human body.

7. The system of claim 5, wherein the one or more internal components of the body comprise a femoral artery of the human body.

8. The system of claim 5, wherein the one or more internal components of the body comprise a heart of the human body and lungs of the human body.

9. The system of claim 5, wherein one of the respective rates is a heart rate.

10. The system of claim 9, wherein the heart rate is a nighttime resting heart rate.

11. The system of claim 10, wherein the computation unit is further configured, in computation of the nighttime resting heart rate, to not use a portion of the measured frequency that is not indicative of movement of a heart of the human body.

12. The system of claim 10, wherein the computation unit is further configured, in computation of the nighttime resting heart rate, to not use a portion of the measured frequency that corresponds to a non-periodic behavior.

13. The system of claim 12, wherein the differential detector is further configured to measure an amplitude of the electric field; and
wherein the computation unit is further configured to determine the non-periodic behavior according to the measured amplitude.

14. The system of claim 5, wherein the respective rates comprise a heart rate and a respiration rate.

15. The system of claim 1, wherein the measuring of the frequency of the generated electric field does not comprise measuring a reflection of the generated electric field.

16. The system of claim 1, wherein a first portion of the computation unit is co-located with the differential detector, and a second portion of the computation unit is remotely located from the differential detector and connected to the first portion of the computation unit over a network;
wherein the first portion of the computation unit is configured to determine the respective periodic behavior for each of the one or more internal components of the body; and
wherein the second portion of the computation unit is configured to compute the respective rate of the movement for each of the one or more internal components of the body.

17. A method comprising:
generating an electric field with an electric field generator comprising a differential oscillator oscillating at a nominal frequency;
radiating the electric field through a differential antenna connected to the electric field generator;
measuring, with a differential detector, a frequency of the generated electric field as it interacts with a body in a reactive near-field region of the electric field;
determining, for each of one or more internal components of the body, a respective periodic behavior in the measured frequency indicative of movement of the internal component; and
computing, for each of the one or more internal components of the body, a respective rate of the movement of the internal component according to the respective periodic behavior in the measured frequency.

18. The method of claim 17, wherein the differential oscillator comprises one of a differential tank oscillator or a differential resonator.

19. The method of claim 17, wherein the differential detector comprises a differential demodulator.

20. The method of claim 17, wherein the differential detector comprises one of a differential quadrature demodulator, a differential wideband analog-to-digital converter, or a combination of a differential sample-and-hold circuit and an analog-to-digital converter.

21. The method of claim 17, wherein the body is a human body.

22. The method of claim 21, wherein the one or more internal components of the body comprise a heart of the human body.

23. The method of claim 21, wherein the one or more internal components of the body comprise a femoral artery of the human body.

24. The method of claim 21, wherein the one or more internal components of the body comprise a heart of the human body and lungs of the human body.

25. The method of claim 21, wherein one of the respective rates is a heart rate.

26. The method of claim 25, wherein the heart rate is a nighttime resting heart rate.

27. The method of claim 26, wherein the computing the nighttime resting heart rate comprises not using a portion of the measured frequency that is not indicative of movement of a heart of the human body.

28. The method of claim 26, wherein the computing the nighttime resting heart rate comprises not using a portion of the measured frequency that corresponds to a non-periodic behavior.

29. The method of claim 28, further comprising:
measuring, with the differential detector, an amplitude of the electric field; and
determining the non-periodic behavior according to the measured amplitude.

30. The method of claim 21, wherein the respective rates comprise a heart rate and a respiration rate.

31. The method of claim 17, wherein the measuring of the frequency of the generated electric field does not comprise measuring a reflection of the generated electric field.

* * * * *